(12) United States Patent
Meade et al.

(10) Patent No.: US 9,962,155 B2
(45) Date of Patent: May 8, 2018

(54) APPARATUS AND METHOD FOR MINIMALLY INVASIVE SUTURING

(71) Applicant: ENDOEVOLUTION, LLC, Raynham, MA (US)

(72) Inventors: John C. Meade, Mendon, MA (US); Jerry R. Griffiths, Pembroke, MA (US); Francis J. DiFrancesco, Foxboro, MA (US); Richard Clark, Holliston, NY (US)

(73) Assignee: EndoEvolution, LLC, Raynham, MA (US)

( * ) Notice: Subject to any disclaimer, the term of this patent is extended or adjusted under 35 U.S.C. 154(b) by 0 days. days.

(21) Appl. No.: 15/671,450

(22) Filed: Aug. 8, 2017

(65) Prior Publication Data

US 2017/0360433 A1    Dec. 21, 2017

Related U.S. Application Data

(63) Continuation of application No. 15/480,561, filed on Apr. 6, 2017, now Pat. No. 9,795,376, which is a
(Continued)

(51) Int. Cl.
| | | |
|---|---|---|
| *A61B 17/04* | (2006.01) | |
| *A61B 17/062* | (2006.01) | |
| *A61B 17/06* | (2006.01) | |

(52) U.S. Cl.
CPC ...... *A61B 17/0469* (2013.01); *A61B 17/0482* (2013.01); *A61B 17/0625* (2013.01); *A61B 17/06066* (2013.01); *A61B 2017/047* (2013.01)

(58) Field of Classification Search
CPC ............ A61B 17/0469; A61B 17/0491; A61B 17/06066; A61B 17/0625;
(Continued)

(56) References Cited

U.S. PATENT DOCUMENTS

| 1,327,577 A | 1/1920 | Turner |
|---|---|---|
| 1,822,330 A | 9/1931 | Ainslie |
| (Continued) | | |

FOREIGN PATENT DOCUMENTS

| CN | 2169381 | 6/1994 |
|---|---|---|
| CN | 201082170 | 7/2008 |
| (Continued) | | |

OTHER PUBLICATIONS

Japanese Office Action dated Oct. 18, 2017, from Japanese patent application No. 2016-187970.
(Continued)

*Primary Examiner* — Gregory Anderson
(74) *Attorney, Agent, or Firm* — Crawford Maunu PLLC

(57) ABSTRACT

An apparatus and method for minimally invasive suturing is disclosed. A suturing device for minimally invasive suturing includes proximal section having a proximal end, a distal end, and a longitudinal axis therebetween, a suture head assembly extending from the distal end of the proximal section; a suturing needle having a pointed end and a blunt end, the suturing needle capable of rotating about an axis approximately perpendicular to a longitudinal axis of the proximal section, wherein the pointed end of the suturing needle is positioned within the suture head assembly prior to and after rotation of the suturing needle, and an actuator extending from the proximal end of the proximal section to actuate a reciprocating needle drive having a needle driver for engaging and rotating the suturing needle.

18 Claims, 88 Drawing Sheets

Related U.S. Application Data continuation of application No. 15/357,375, filed on Nov. 21, 2016, now Pat. No. 9,700,301, which is a continuation of application No. 15/265,650, filed on Sep. 14, 2016, now Pat. No. 9,597,071, which is a continuation of application No. 14/796,642, filed on Jul. 10, 2015, now Pat. No. 9,474,523, which is a continuation of application No. 14/472,090, filed on Aug. 28, 2014, now Pat. No. 9,451,948, which is a continuation of application No. 13/361,444, filed on Jan. 30, 2012, now Pat. No. 8,821,519, which is a continuation of application No. 12/592,174, filed on Nov. 20, 2009, now Pat. No. 8,123,764, which is a continuation-in-part of application No. 12/175,442, filed on Jul. 17, 2008, now Pat. No. 7,976,555, and a continuation-in-part of application No. PCT/US2008/006674, filed on May 23, 2008, and a continuation-in-part of application No. 11/231,135, filed on Sep. 20, 2005, now Pat. No. 7,862,572.

(60) Provisional application No. 61/200,180, filed on Nov. 25, 2008, provisional application No. 60/939,887, filed on May 24, 2007, provisional application No. 60/611,362, filed on Sep. 20, 2004.

(58) Field of Classification Search
CPC .. A61B 2017/0023; A61B 2017/00407; A61B 2017/00473; A61B 2017/06028
See application file for complete search history.

(56) References Cited

U.S. PATENT DOCUMENTS

| | | |
|---|---|---|
| 2,327,353 A | 8/1943 | Karle |
| 2,601,564 A | 6/1952 | Smith |
| 3,197,997 A | 8/1965 | Kurtz |
| 3,311,110 A | 3/1967 | Singerman et al. |
| 3,344,790 A | 10/1967 | Dorner |
| 3,762,418 A | 10/1973 | Wasson |
| 3,834,599 A | 9/1974 | Herr |
| 3,835,912 A | 9/1974 | Kristensen et al. |
| 3,910,282 A | 10/1975 | Messer et al. |
| 3,951,261 A | 4/1976 | Mandel et al. |
| 3,972,418 A | 8/1976 | Schuler et al. |
| 4,027,608 A | 6/1977 | Arbuckle |
| 4,074,732 A | 2/1978 | Wilkens |
| 4,235,177 A | 11/1980 | Arbuckle |
| 4,327,655 A | 5/1982 | Addy et al. |
| 4,331,277 A | 5/1982 | Green |
| 4,437,465 A | 3/1984 | Nomoto et al. |
| 4,509,945 A | 4/1985 | Kramann et al. |
| 4,527,564 A | 7/1985 | Eguchi et al. |
| 4,557,265 A | 12/1985 | Andersson |
| 4,621,640 A | 11/1986 | Mulhollan et al. |
| 4,841,888 A | 6/1989 | Mills et al. |
| 4,899,746 A * | 2/1990 | Brunk ............... A61B 17/0491 112/169 |
| 4,957,502 A | 9/1990 | Takase |
| 5,080,663 A | 1/1992 | Mills et al. |
| 5,089,012 A | 2/1992 | Prou |
| 5,174,300 A | 12/1992 | Bales |
| 5,201,760 A | 4/1993 | West |
| 5,210,376 A | 5/1993 | Caviar |
| 5,269,806 A | 12/1993 | Sardelis et al. |
| 5,305,281 A | 4/1994 | Lubeck |
| 5,306,281 A | 4/1994 | Beurrier |
| 5,308,353 A | 5/1994 | Beurrier |
| 5,318,566 A | 6/1994 | Miller |
| 5,318,578 A | 6/1994 | Hasson |
| 5,330,502 A | 7/1994 | Hassler |
| 5,344,061 A | 9/1994 | Crainich |
| 5,358,498 A | 10/1994 | Shave |
| 5,364,408 A | 11/1994 | Gordon |
| 5,373,101 A | 12/1994 | Barabolak |
| 5,376,101 A | 12/1994 | Green et al. |
| 5,387,221 A | 2/1995 | Bisgaard |
| 5,403,344 A | 4/1995 | Allen |
| 5,437,681 A | 8/1995 | Meade et al. |
| 5,454,819 A | 10/1995 | Knoepfler |
| 5,462,558 A | 10/1995 | Kolesa et al. |
| 5,472,081 A | 12/1995 | Kilgrow et al. |
| 5,474,568 A | 12/1995 | Scott |
| 5,478,344 A | 12/1995 | Stone et al. |
| 5,478,345 A | 12/1995 | Stone et al. |
| 5,480,409 A | 1/1996 | Riza |
| 5,503,266 A | 4/1996 | Kalbfeld et al. |
| 5,514,159 A | 5/1996 | Matula et al. |
| 5,540,705 A | 7/1996 | Meade et al. |
| 5,571,119 A | 11/1996 | Atala |
| 5,575,800 A | 11/1996 | Gordon |
| 5,578,044 A | 11/1996 | Gordon et al. |
| 5,643,295 A | 7/1997 | Yoon |
| 5,645,552 A | 7/1997 | Sherts |
| 5,665,096 A | 9/1997 | Yoon |
| 5,665,109 A | 9/1997 | Yoon |
| 5,669,490 A | 9/1997 | Colligan et al. |
| 5,675,961 A | 10/1997 | Cerwin et al. |
| 5,709,693 A | 1/1998 | Taylor |
| 5,713,910 A | 2/1998 | Gordon et al. |
| 5,715,942 A | 2/1998 | Li et al. |
| 5,741,277 A | 4/1998 | Gordon et al. |
| 5,755,729 A | 5/1998 | de la Torre et al. |
| 5,759,188 A | 6/1998 | Yoon |
| 5,766,186 A | 6/1998 | Faraz et al. |
| 5,814,069 A | 9/1998 | Schulze et al. |
| 5,814,071 A | 9/1998 | McDevitt et al. |
| 5,830,234 A | 11/1998 | Wojciechowicz et al. |
| 5,833,695 A | 11/1998 | Yoon |
| 5,860,992 A | 1/1999 | Daniel et al. |
| 5,891,160 A | 4/1999 | Williamson, IV et al. |
| 5,906,273 A | 5/1999 | Pohle et al. |
| 5,908,426 A | 6/1999 | Pierce |
| 5,908,428 A | 6/1999 | Scirica et al. |
| 5,911,727 A | 6/1999 | Taylor |
| 5,954,733 A | 9/1999 | Yoon |
| 5,968,077 A | 10/1999 | Wojciechowicz et al. |
| 5,993,466 A | 11/1999 | Yoon |
| 6,016,905 A | 1/2000 | Gemma et al. |
| 6,036,694 A | 3/2000 | Goble et al. |
| 6,048,351 A | 4/2000 | Gordon et al. |
| 6,053,908 A | 4/2000 | Crainich et al. |
| 6,056,771 A | 5/2000 | Proto |
| 6,071,289 A | 6/2000 | Stefanchik et al. |
| 6,096,051 A | 8/2000 | Kortenbach et al. |
| 6,126,666 A | 10/2000 | Trapp et al. |
| 6,135,385 A | 10/2000 | Martinez de Lahidalga |
| 6,136,010 A | 10/2000 | Modesitt et al. |
| 6,159,224 A | 12/2000 | Yoon |
| 6,261,307 B1 | 7/2001 | Yoon et al. |
| 6,270,508 B1 | 8/2001 | Klieman et al. |
| 6,322,581 B1 | 11/2001 | Fukuda et al. |
| 6,332,888 B1 | 12/2001 | Levy et al. |
| 6,346,111 B1 | 2/2002 | Gordon et al. |
| 6,443,962 B1 | 9/2002 | Gaber |
| 6,454,777 B1 | 9/2002 | Green |
| 6,454,778 B2 | 9/2002 | Kortenbach |
| 6,494,888 B1 | 12/2002 | Laufer et al. |
| 6,506,196 B1 | 1/2003 | Laufer |
| 6,558,400 B2 | 5/2003 | Deem et al. |
| 6,656,194 B1 | 12/2003 | Gannoe et al. |
| 6,663,639 B1 | 12/2003 | Laufer et al. |
| 6,719,763 B2 | 4/2004 | Chung et al. |
| 6,719,764 B1 | 4/2004 | Gellman et al. |
| 6,746,460 B2 | 6/2004 | Gannoe et al. |
| 6,755,843 B2 | 6/2004 | Chung et al. |
| 6,835,200 B2 | 12/2004 | Laufer et al. |
| 6,877,352 B1 | 4/2005 | Schlereth |
| 6,908,427 B2 | 6/2005 | Fleener et al. |
| 6,923,819 B2 | 8/2005 | Meade et al. |
| 6,955,643 B2 | 10/2005 | Gellman et al. |
| 7,004,951 B2 | 2/2006 | Gibbens, III |
| 7,033,370 B2 | 4/2006 | Gordon et al. |

(56) References Cited

U.S. PATENT DOCUMENTS

| | | |
|---|---|---|
| 7,041,111 B2 | 5/2006 | Chu |
| 7,144,401 B2 | 12/2006 | Yamamoto et al. |
| 7,166,116 B2 | 1/2007 | Lizardi et al. |
| 7,338,504 B2 | 3/2008 | Gibbens et al. |
| 7,615,060 B2 | 11/2009 | Stokes et al. |
| 7,628,796 B2 | 12/2009 | Shelton, IV et al. |
| 7,637,909 B2 | 12/2009 | Lechot et al. |
| 7,766,925 B2 | 8/2010 | Stokes et al. |
| 7,828,812 B2 | 11/2010 | Stokes et al. |
| 7,833,236 B2 | 11/2010 | Stokes et al. |
| 7,846,169 B2 | 12/2010 | Shelton, IV et al. |
| 7,862,572 B2 | 1/2011 | Meade et al. |
| 7,887,554 B2 | 2/2011 | Stokes et al. |
| 7,976,533 B2 | 7/2011 | Larsson |
| 7,976,555 B2 | 7/2011 | Meade et al. |
| 7,993,354 B1 | 8/2011 | Brecher et al. |
| 8,066,737 B2 | 11/2011 | Meade et al. |
| 8,123,764 B2 | 2/2012 | Meade et al. |
| 8,469,973 B2 | 6/2013 | Meade et al. |
| 8,500,756 B2 | 8/2013 | Papa et al. |
| 8,623,048 B2 | 1/2014 | Brecher et al. |
| 8,641,728 B2 | 2/2014 | Stokes et al. |
| 8,702,732 B2 | 4/2014 | Woodard, Jr. et al. |
| 8,906,043 B2 | 12/2014 | Woodard, Jr. et al. |
| 9,125,645 B1 | 9/2015 | Martin et al. |
| 9,173,655 B2 | 11/2015 | Martin |
| 9,220,496 B2 | 12/2015 | Martin et al. |
| 9,357,998 B2 | 6/2016 | Martin et al. |
| 9,370,354 B1 | 6/2016 | Martin et al. |
| 9,375,212 B2 | 6/2016 | Martin et al. |
| 9,398,905 B2 | 7/2016 | Martin |
| 9,427,226 B2 | 8/2016 | Martin et al. |
| 9,427,227 B2 | 8/2016 | Martin et al. |
| 9,445,807 B2 | 9/2016 | Brecher et al. |
| 9,451,948 B2 | 9/2016 | Meade et al. |
| 9,474,522 B2 | 10/2016 | Deck et al. |
| 9,474,523 B2 | 10/2016 | Meade et al. |
| 9,486,209 B2 | 11/2016 | Martin et al. |
| 9,498,207 B2 | 11/2016 | Martin et al. |
| 9,526,495 B2 | 12/2016 | Martin et al. |
| 2002/0107530 A1 | 8/2002 | Sauer et al. |
| 2002/0116011 A1 | 8/2002 | Chee Chung et al. |
| 2002/0173800 A1 | 11/2002 | Dreyfuss et al. |
| 2002/0193809 A1 | 12/2002 | Meade et al. |
| 2002/0198542 A1 | 12/2002 | Yamamoto et al. |
| 2003/0083674 A1 | 5/2003 | Gibbens |
| 2003/0105475 A1 | 6/2003 | Sancoff et al. |
| 2003/0171760 A1 | 9/2003 | Gambale |
| 2003/0181924 A1 | 9/2003 | Yamamoto et al. |
| 2003/0233104 A1 | 12/2003 | Gellman et al. |
| 2003/0233108 A1 | 12/2003 | Gellman et al. |
| 2004/0034369 A1 | 2/2004 | Sauer et al. |
| 2004/0034372 A1 | 2/2004 | Chu |
| 2004/0044354 A1 | 3/2004 | Gannoe et al. |
| 2004/0059350 A1 | 3/2004 | Gordon et al. |
| 2004/0082963 A1 | 4/2004 | Gannoe et al. |
| 2004/0088008 A1 | 5/2004 | Gannoe et al. |
| 2004/0122473 A1 | 6/2004 | Ewers et al. |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0162568 A1 | 8/2004 | Saadat et al. |
| 2004/0181243 A1 | 9/2004 | Chu et al. |
| 2004/0194790 A1 | 10/2004 | Laufer et al. |
| 2004/0210243 A1 | 10/2004 | Gannoe et al. |
| 2004/0260344 A1 | 12/2004 | Lyons et al. |
| 2005/0015101 A1 | 1/2005 | Gibbens, III et al. |
| 2005/0035007 A1 | 2/2005 | Kennedy et al. |
| 2005/0055038 A1 | 3/2005 | Kelleher et al. |
| 2005/0070931 A1 | 3/2005 | Li et al. |
| 2005/0075653 A1 | 4/2005 | Saadat et al. |
| 2005/0262984 A1 | 12/2005 | Hetcher et al. |
| 2006/0069396 A1 | 3/2006 | Meade et al. |
| 2006/0111732 A1 | 5/2006 | Gibbens et al. |
| 2006/0224184 A1 | 10/2006 | Stefanchik et al. |
| 2006/0282089 A1 | 12/2006 | Stokes et al. |
| 2006/0282090 A1 | 12/2006 | Stokes et al. |
| 2006/0282091 A1 | 12/2006 | Shelton et al. |
| 2006/0282092 A1 | 12/2006 | Stokes et al. |
| 2006/0282093 A1 | 12/2006 | Shelton et al. |
| 2006/0282094 A1 | 12/2006 | Stokes et al. |
| 2006/0282095 A1 | 12/2006 | Stokes et al. |
| 2006/0282096 A1 | 12/2006 | Papa et al. |
| 2006/0282097 A1 | 12/2006 | Ortiz et al. |
| 2006/0282098 A1 | 12/2006 | Shelton et al. |
| 2006/0282099 A1 | 12/2006 | Stokes et al. |
| 2007/0135838 A1 | 6/2007 | Meyer |
| 2008/0132919 A1 | 6/2008 | Chui et al. |
| 2008/0140091 A1 | 6/2008 | DeDeyne et al. |
| 2009/0024145 A1 | 1/2009 | Meade et al. |
| 2010/0036415 A1 | 2/2010 | Cabezas |
| 2010/0049219 A1 | 2/2010 | Cronin et al. |
| 2010/0130990 A1 | 5/2010 | Saliman |
| 2010/0152751 A1 | 6/2010 | Meade et al. |
| 2014/0171977 A1 | 6/2014 | Martin et al. |
| 2014/0171979 A1 | 6/2014 | Martin et al. |
| 2014/0172015 A1 | 6/2014 | Martin et al. |
| 2015/0133967 A1 | 5/2015 | Martin |
| 2015/0351745 A1 | 12/2015 | Mumaw et al. |
| 2015/0351746 A1 | 12/2015 | Martin et al. |
| 2015/0351749 A1 | 12/2015 | Martin et al. |
| 2015/0351756 A1 | 12/2015 | Martin et al. |
| 2016/0317148 A1 | 11/2016 | Martinez |
| 2016/0331374 A1 | 11/2016 | Martin et al. |
| 2016/0345958 A1 | 12/2016 | Martin et al. |
| 2016/0346827 A1 | 12/2016 | Martin et al. |
| 2016/0361055 A1 | 12/2016 | Martin et al. |
| 2016/0367238 A1 | 12/2016 | Deck et al. |
| 2016/0367239 A1 | 12/2016 | Mumaw et al. |
| 2016/0367240 A1 | 12/2016 | Shelton, IV et al. |
| 2016/0367243 A1 | 12/2016 | Martin et al. |

FOREIGN PATENT DOCUMENTS

| | | |
|---|---|---|
| DE | 4310315 | 10/1993 |
| EP | 0648474 | 4/1995 |
| EP | 1733685 A1 | 12/2006 |
| EP | 1839591 A1 | 10/2007 |
| EP | 2103262 | 9/2009 |
| EP | 05797831 | 2/2011 |
| EP | 10009832 | 2/2011 |
| EP | 2292157 | 3/2011 |
| EP | 2308391 | 4/2011 |
| EP | 2370002 | 10/2011 |
| EP | 1791476 | 12/2015 |
| FR | 2540377 | 8/1984 |
| GB | 18602 | 9/1908 |
| JP | 556270 | 1/1980 |
| JP | 55151956 | 11/1980 |
| JP | 07178100 | 7/1995 |
| JP | 07328021 | 12/1995 |
| JP | H11276492 | 10/1999 |
| JP | 2000139931 | 5/2000 |
| JP | 2005080761 | 3/2005 |
| JP | 2005253987 | 9/2005 |
| WO | WO9609769 | 4/1996 |
| WO | WO9609796 A2 | 4/1996 |
| WO | WO9729694 | 8/1997 |
| WO | WO9912482 | 3/1999 |
| WO | WO9940850 | 8/1999 |
| WO | WO9947050 | 9/1999 |
| WO | WO0112084 | 2/2001 |
| WO | WO02102226 | 12/2002 |
| WO | WO2003028541 | 10/2003 |
| WO | WO2004012606 | 2/2004 |
| WO | WO2004021894 | 3/2004 |
| WO | WO2004028402 | 4/2004 |
| WO | WO2004086986 | 10/2004 |
| WO | WO2006034209 | 3/2006 |
| WO | WO2007089603 | 8/2007 |

(56) References Cited

FOREIGN PATENT DOCUMENTS

| WO | WO2008147555 | 12/2008 |
|---|---|---|
| WO | WO2010062380 | 6/2010 |

OTHER PUBLICATIONS

Japanese Office Action dated Oct. 18, 2017, from Japanese patent application No. 2016-187970 (English).
International Preliminary Report on Patentability dated Jan. 13, 2008 and Written Opinion dated Jun. 13, 2008 for PCT/US05/33507.
International Preliminary Report on Patentability dated Jan. 27, 2006 and Written Opinion dated Nov. 1, 2007 for PCT/US07/02204.
International Search Report and Written Opinion dated Mar. 3, 2003 for PCT/US02/12560.
International Preliminary Examination Report dated Mar. 12, 2004 for PCT/US02/12560.
International Search Report and Written Opinion dated Jul. 5, 2010 for PCT/US09/06212.
Supplemental European Search Report dated Mar. 15, 2007 for EP140654.5.
European Search Report dated Feb. 8, 2011 for EP10009831.8.
European Search Report dated Feb. 9, 2011 for EP10009832.6.
Office Action dated Jul. 1, 2014 from Corresponding Japanese Application No. 2013-138559.
European Search Report dated Jun. 5, 2015 from corresponding European Application No. 12822057.1.
European Search Report dated Aug. 14, 2015 from corresponding European Application No. 11830008.
International Search Report issued in related PCT application No. PCT/US07/002204 dated Nov. 1, 2007.
Written Opinion issued in related PCT application No. PCT/US07/002204 dated Nov. 1, 2007.
Search Report dated May 20, 2010 from SG Application No. 200805426-4.
Extended Search Report dated Feb. 17, 2011 from corresponding European Application No. 05797831.4.
Extended Search Report dated Feb. 21, 2011 from corresponding European Application No. 10009831.8.
Extended Search Report dated Feb. 21, 2011 from corresponding European Application No. 10009832.6.
European Search Report dated Mar. 11, 2011 from corresponding European Application No. 07762862.6.
Japanese Office Action dated Oct. 18, 2011 from Corresponding Japanese Application No. 2008-552444.
International Preliminary Report on Patentability dated Feb. 11, 2014 from Corresponding PCT Application No. PCT/US12/049979.
International Search Report and Written Opinion of the International Searching Authority (ISA) dated Apr. 24, 2012 relating to PCT/US11/054334.
Examination Report issued by Hungarian IP Office on behalf of Singapore IP Office dated Feb. 8, 2012 in connection with Singapore Application No. 200907505-2.
Supplementary European Search Report dated Mar. 23, 2007 in connection with EP Application No. 02725747.6.
Supplementary European Search Report dated Oct. 6, 2009 in connection with EP Application No. 02725747.6.
Office Action with English translation in connection with Japanese Patent Application No. JP2007-532595 dated Jan. 4, 2011.
Extended Search Report in connection with EP05797831.4 dated Feb. 25, 2011.
Written Opinion dated Jan. 11, 2011 in connection with Singapore Patent Application No. 200907505-2.
International Search Report and Written Opinion dated Jan. 5, 2009 in connection with PCT/US08/006674.
International Preliminary Report on Patentability dated Nov. 24, 2009 in connection with PCT/US08/006674.
International Search Report issued in related PCT application No. PCT/US09/006212 dated Jul. 5, 2010.
International Search Report issued in related PCT application No. PCT/US05/33507 dated Jun. 13, 2008.
Extended Search Report dated Nov. 29, 2012 from corresponding European Application No. 09829467.1.
Ethicon Exhibit 1001 in IPR Case No. 2016-00071; U.S. Pat. No. 6,923,819, issued Aug. 2, 2005, 32 pages.
Ethicon Exhibit 1002 in IPR Case No. 2016-00071; Prosecution History of U.S. Appl. No. 10/127,254, filed Apr. 22, 2002, 359 pages.
Ethicon Exhibit 1003 in IPR Case No. 2016-00071; Expert Declaration of Kevin L. Houser, M.S., dated Oct. 22, 2015, 105 pages.
Ethicon Exhibit 1004 in IPR Case No. 2016-00071; U.S. Pat. No. 5,437,681, issued Aug. 1, 1995, 15 pages.
Ethicon Exhibit 1005 in IPR Case No. 2016-00071; U.S. Pat. No. 5,306,281, issued Apr. 26, 1994, 12 pages.
Ethicon Exhibit 1006 in IPR Case No. 2016-00071; U.S. Pat. No. 4,557,265, issued Dec. 10, 1985, 4 pages.
Ethicon Exhibit 1007 in IPR Case No. 2016-00071; U.S. Pat. No. 6,053,908, issued Apr. 25, 2000, 9 pages.
Ethicon Exhibit 1008 in IPR Case No. 2016-00071; U.S. Pat. No. 5,911,727, issued Jun. 15, 1999, 12 pages.
Ethicon Exhibit 1009 in IPR Case No. 2016-00071; N. Chironis, Mechanisms, Linkages, and Mechanical Control, 5th ed. 1965, 8 pages.
Ethicon Exhibit 1010 in IPR Case No. 2016-00071; "Webster's New Universal Unabridged Dictionary," 2nd Edition 1983, 4 pages.
Exhibit 2001 in IPR Case No. 2016-00071; U.S. Pat. No. 5,709,693, issued Jan. 20, 1998, 7 pages.
Petition for Inter Partes Review of U.S. Pat. No. 6,923,819, dated Oct. 22, 2015, 64 pages.
Patent Owner's Preliminary Response in IPR Case No. 2016-00071, dated Jan. 29, 2016, 49 pages.
Decision on Petition for Inter Partes Review of U.S. Pat. No. 6,923,819 in IPR Case No. 2016-00071, dated Apr. 28, 2016, 17 pages.
Non-Final Office Action in U.S. Appl. No. 15/260,094, dated Jan. 17, 2017, 14 pages.
Preliminary Amendment filed in U.S. Appl. No. 15/260,094, dated Nov. 18, 2016, 7 pages.
Examiner Kondo, Decision of Refusal issued in JP Application No. 2015-112857, dated Dec. 8, 2016, 3 pages.

* cited by examiner

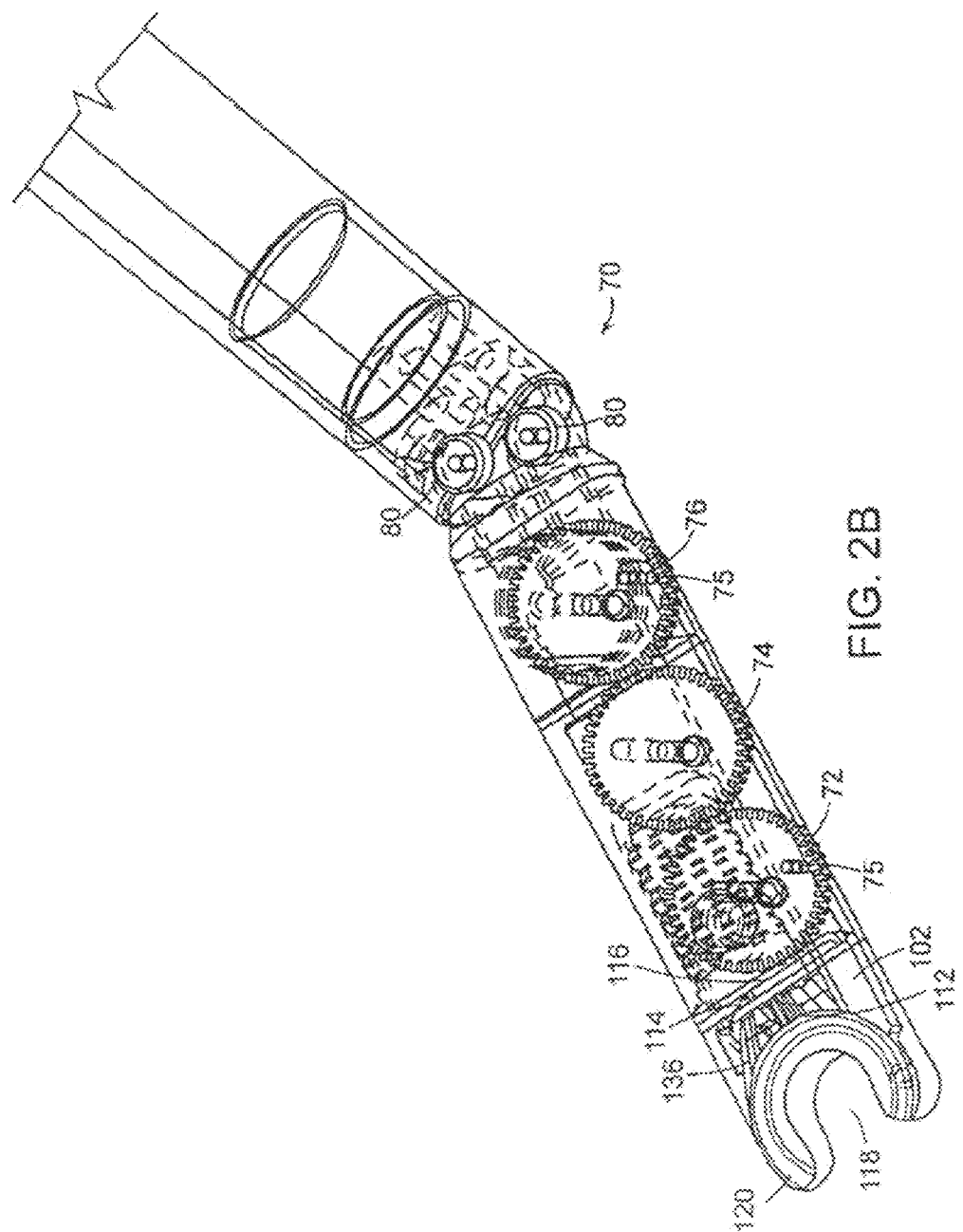

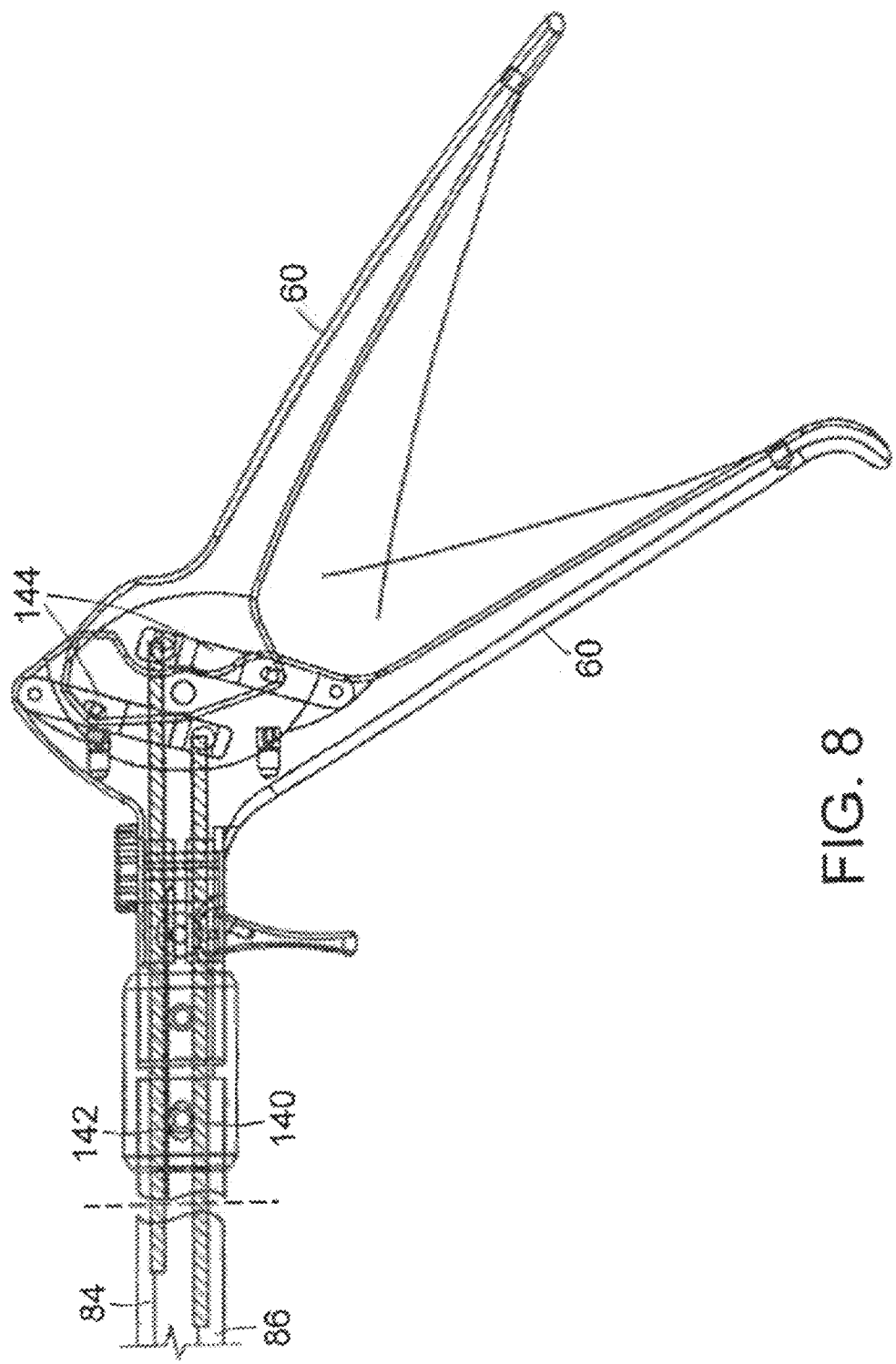

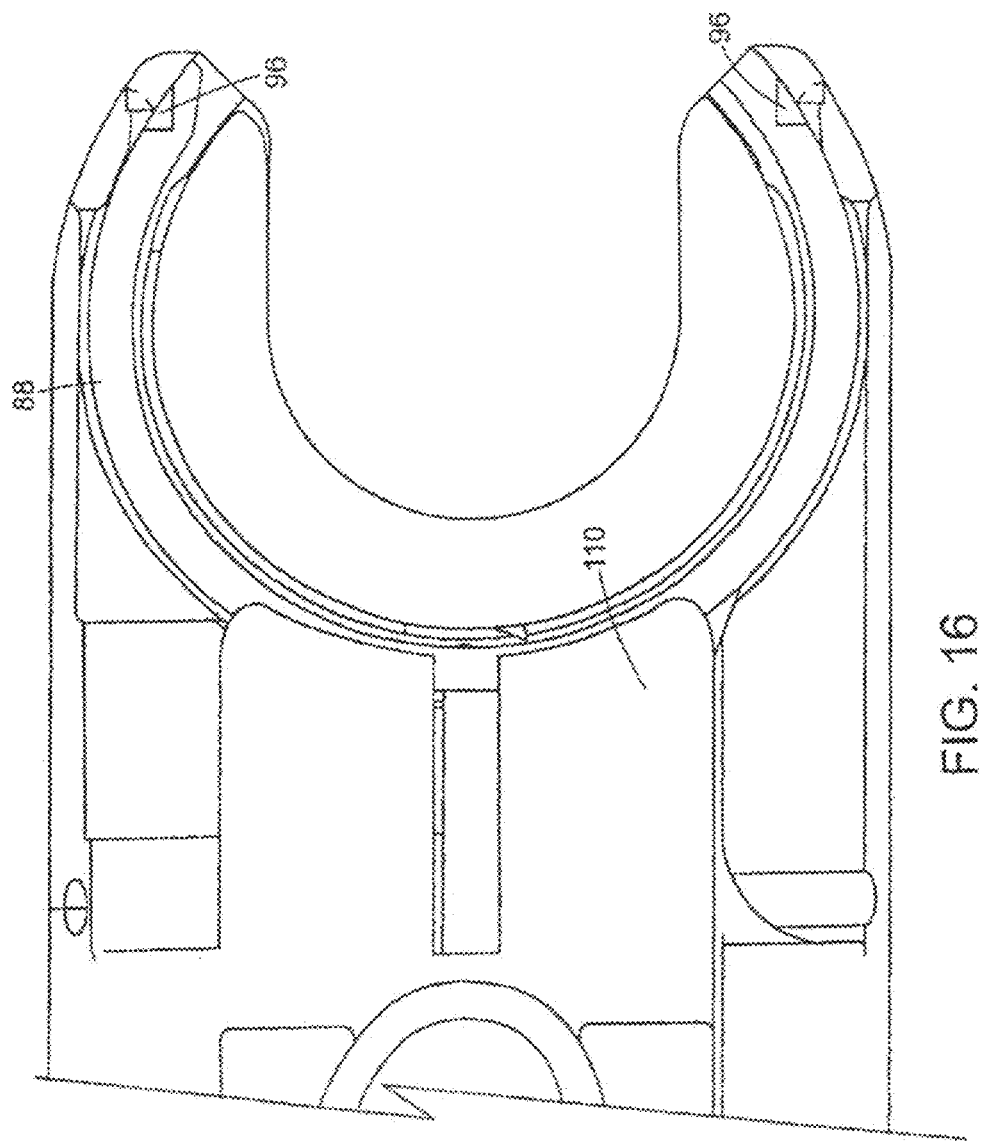

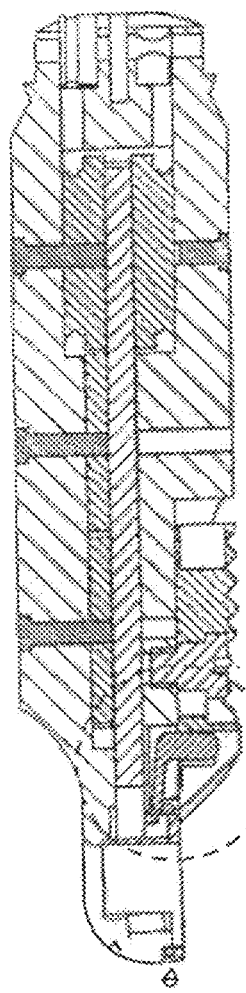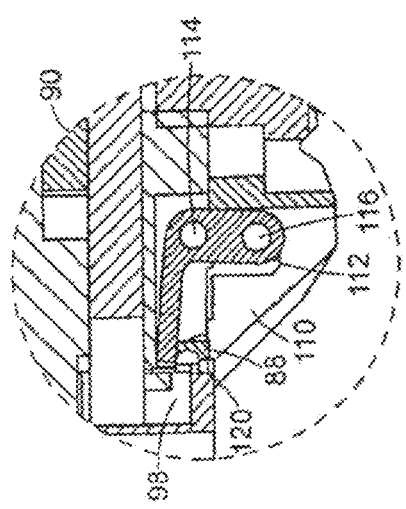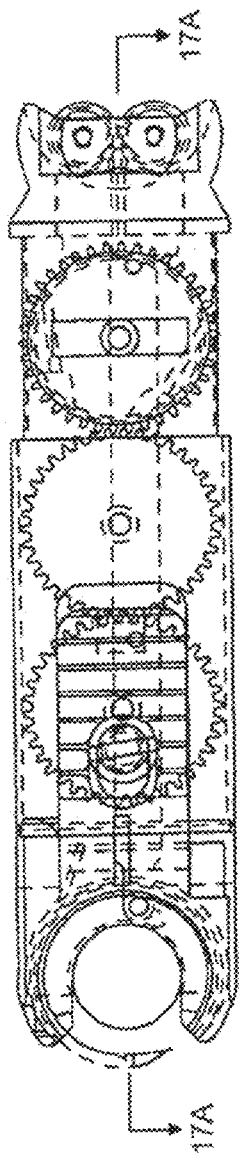

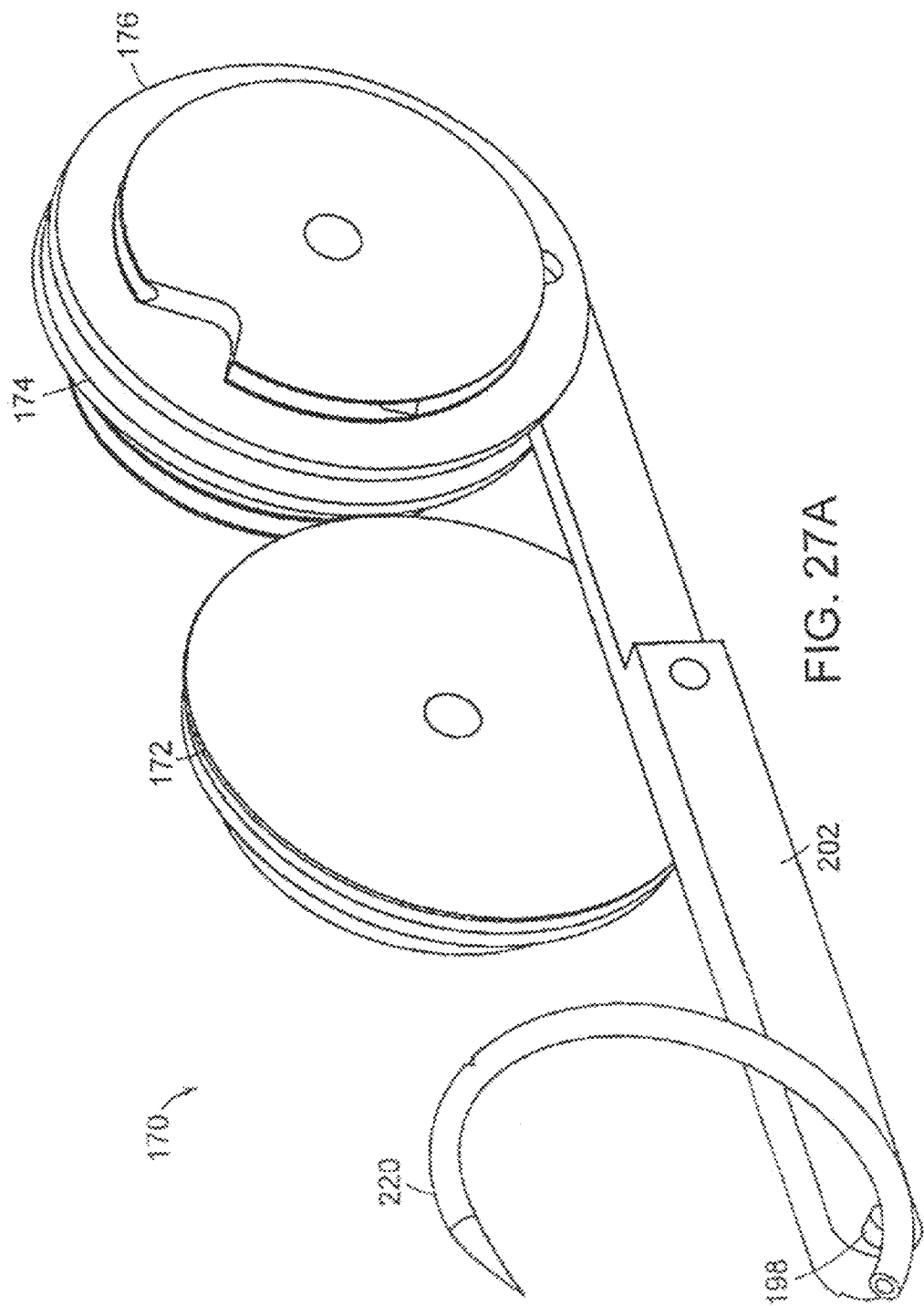

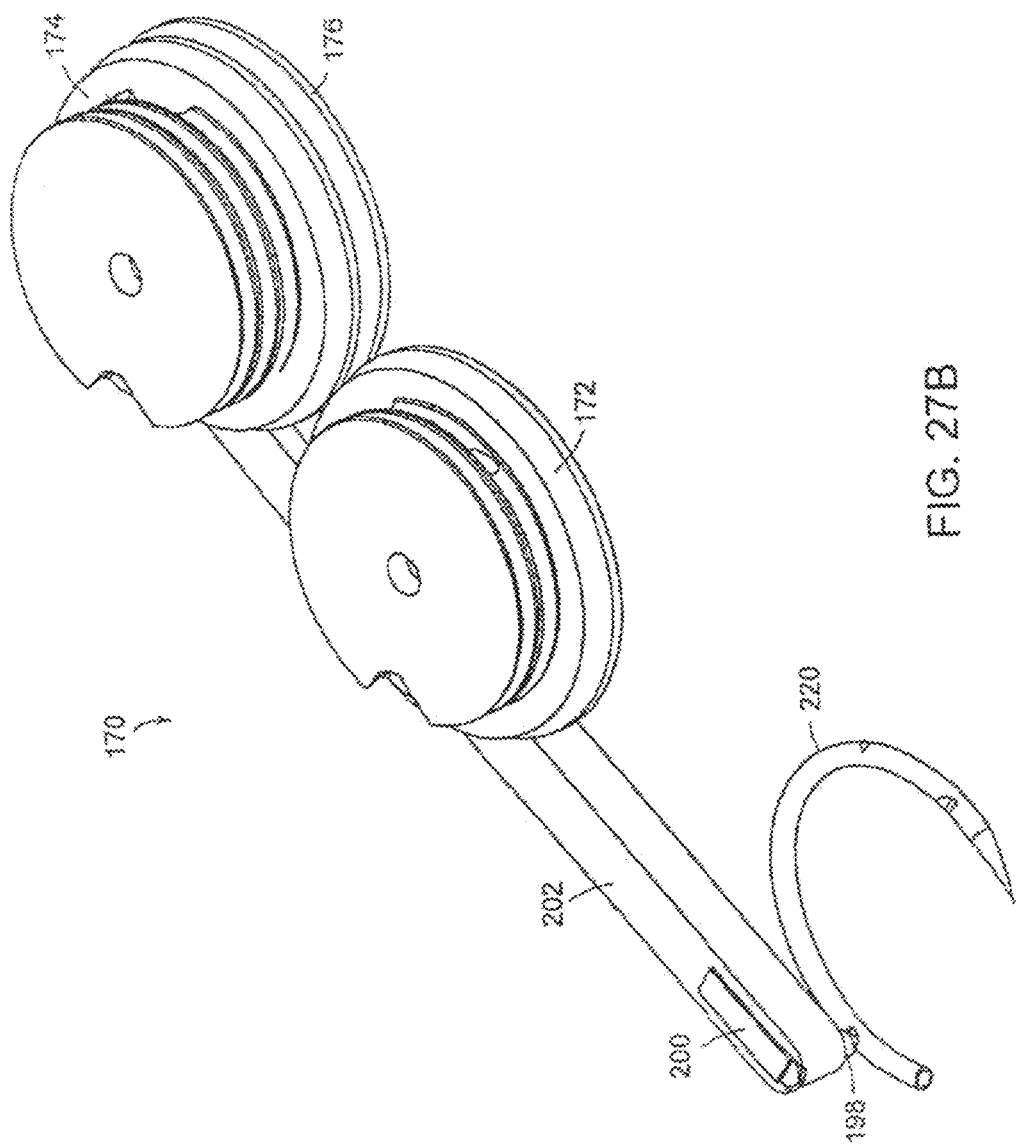

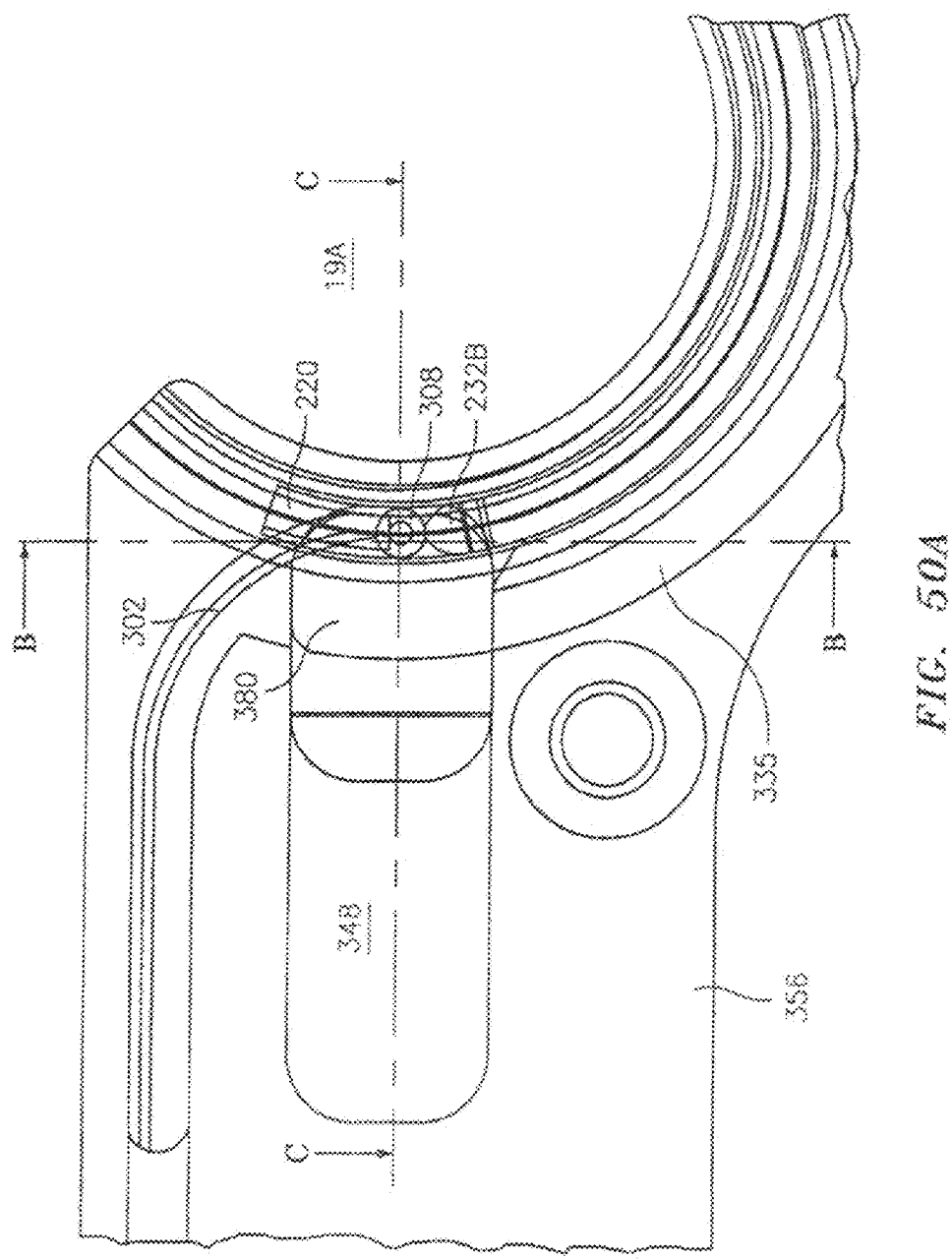

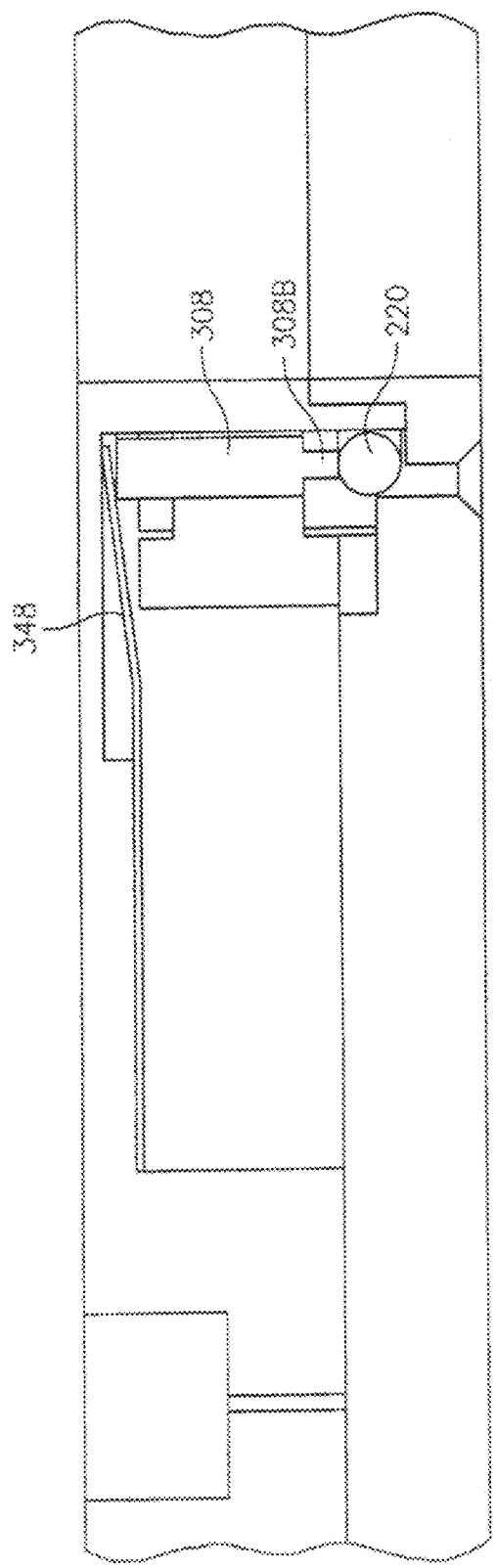

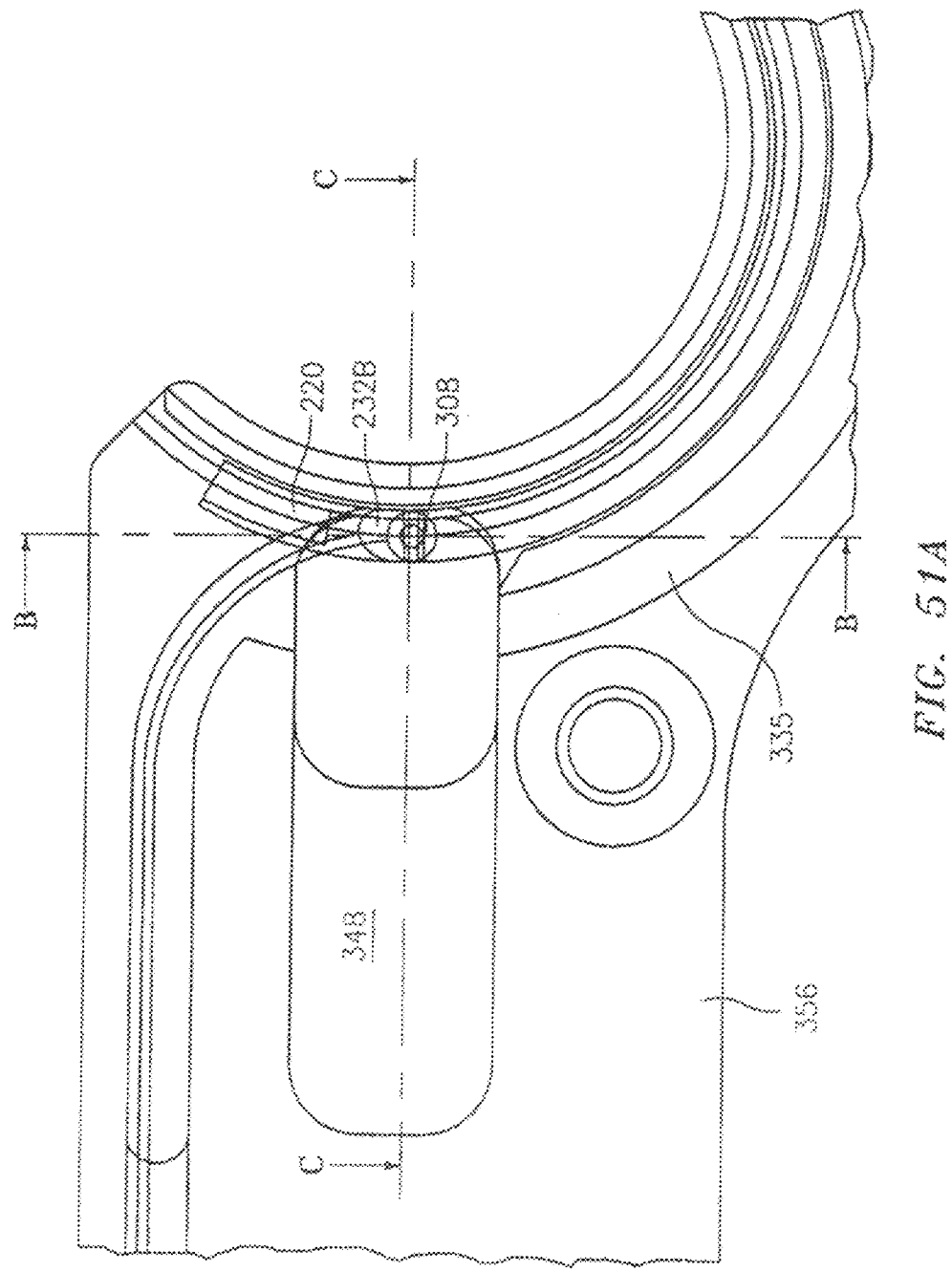

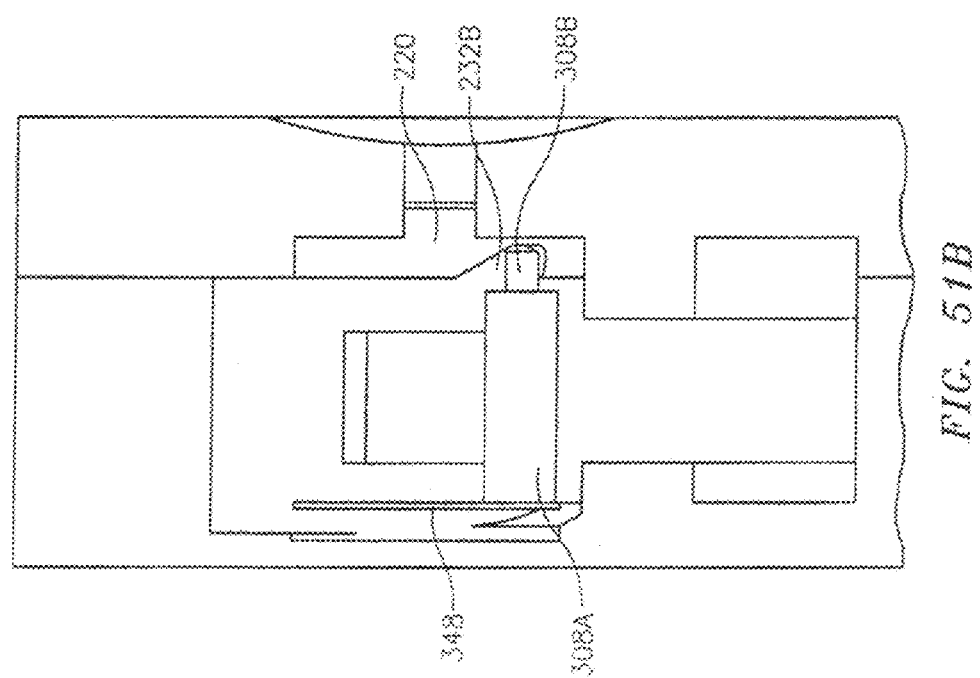

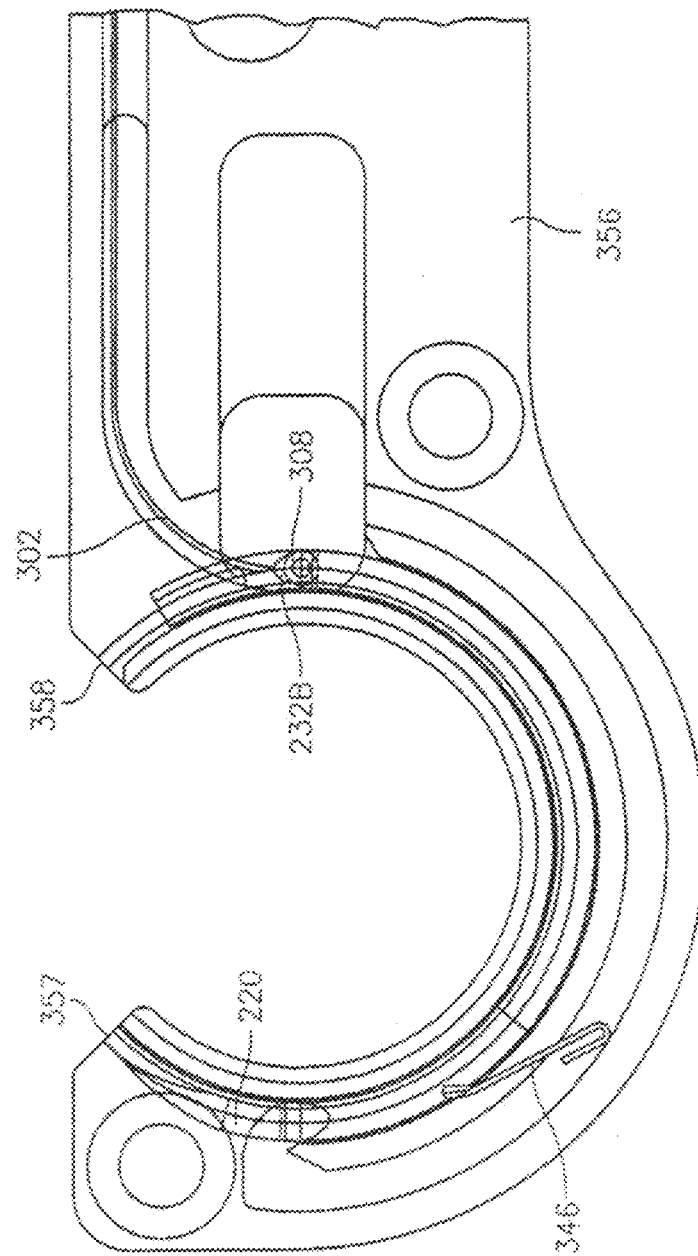

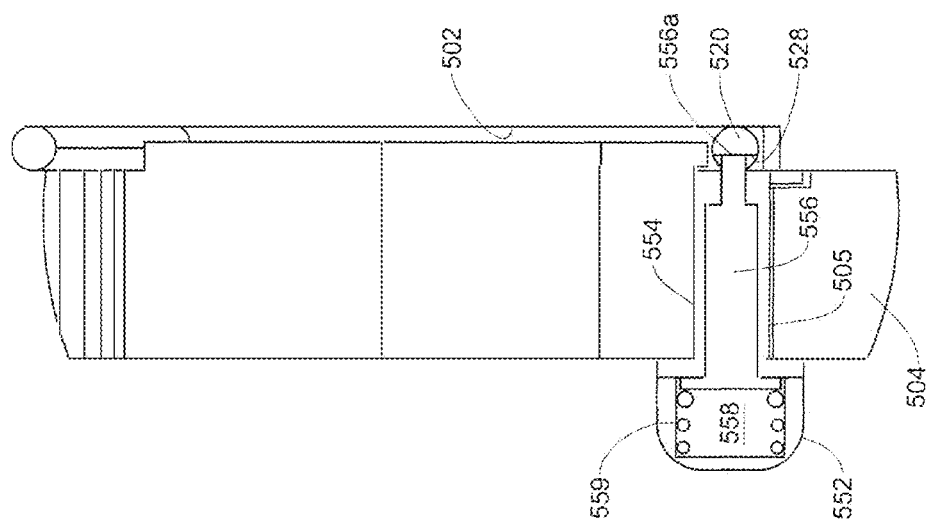

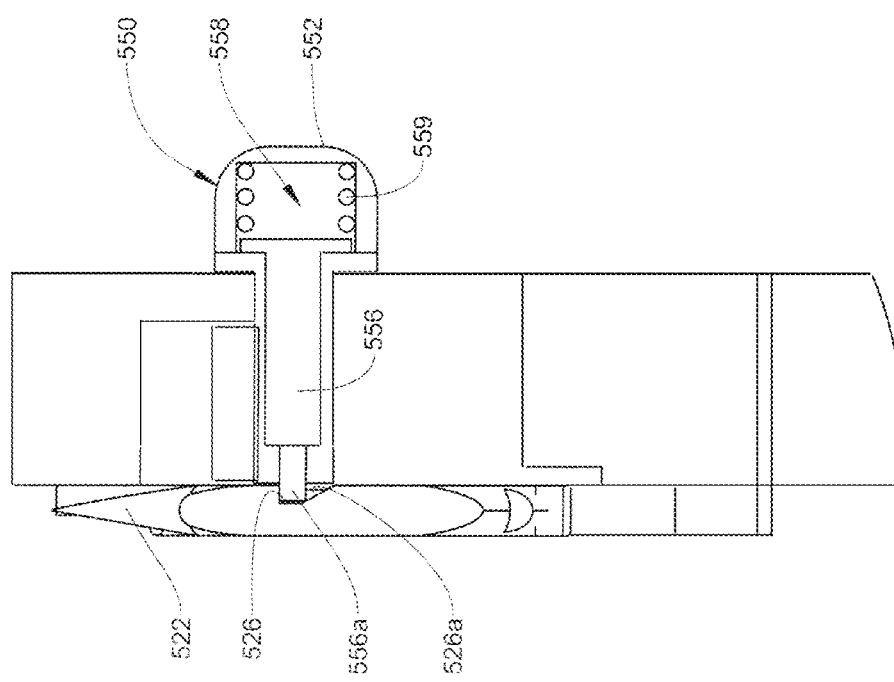

APPARATUS AND METHOD FOR MINIMALLY INVASIVE SUTURING

CROSS-REFERENCE TO RELATED APPLICATIONS

This patent application is a continuation of and claims the benefit of priority to U.S. patent application Ser. No. 15/480,561, filed Apr. 6, 2017, now U.S. Pat. No. 9,795,376, which in turn is a continuation of and claims the benefit of priority to U.S. patent application Ser. No. 15/357,375, filed Nov. 21, 2016, now U.S. Pat. No. 9,700,301, which in turn is a continuation of and claims the benefit of priority to U.S. patent application Ser. No. 15/265,650, filed Sep. 14, 2016, now U.S. Pat. No. 9,597,071, which is a continuation of and claims the benefit of priority to U.S. patent application Ser. No. 14/796,642, filed Jul. 10, 2015, now U.S. Pat. No. 9,474,523, which is a continuation of and claims the benefit of priority to U.S. patent application Ser. No. 14/472,090, filed Aug. 28, 2014, now U.S. Pat. No. 9,451,948, which is a continuation of and claims the benefit of priority to U.S. patent application Ser. No. 13/361,444 filed Jan. 30, 2012, now U.S. Pat. No. 8,821,519, which is a continuation of and claims the benefit of priority to U.S. patent application Ser. No. 12/592,174, filed on Nov. 20, 2009, now U.S. Pat. No. 8,123,764, which is a continuation-in-part of and claims the benefit of priority to U.S. patent application Ser. No. 11/231,135, filed Sep. 20, 2005, now U.S. Pat. No. 7,862,572, which in turn claims the benefit of priority to U.S. Provisional Application Ser. No. 60/611,362, filed Sep. 20, 2004.

This patent application is a continuation of and claims the benefit of priority to U.S. patent application Ser. No. 15/480,561, filed Apr. 6, 2017, now U.S. Pat. No. 9,795,376, which in turn is a continuation of and claims the benefit of priority to U.S. patent application Ser. No. 15/357,375, filed Nov. 21, 2016, now U.S. Pat. No. 9,700,301, which in turn is a continuation of and claims the benefit of priority to U.S. patent application Ser. No. 15/265,650, filed Sep. 14, 2016, now U.S. Pat. No. 9,597,071, which is a continuation of and claims the benefit of priority to U.S. patent application Ser. No. 14/796,642, filed Jul. 10, 2015, now U.S. Pat. No. 9,474,523, which is a continuation of and claims the benefit of priority to U.S. patent application Ser. No. 14/472,090, filed Aug. 28, 2014, now U.S. Pat. No. 9,451,948, which is a continuation of and claims the benefit of priority to U.S. patent application Ser. No. 13/361,444 filed Jan. 30, 2012, now U.S. Pat. No. 8,821,519, which is a continuation of and claims the benefit of priority to U.S. patent application Ser. No. 12/592,174, filed on Nov. 20, 2009, now U.S. Pat. No. 8,123,764, which is a continuation-in-part of and claims the benefit of priority to International Application No. PCT/US2008/06674 filed May 23, 2008, which in turn claims the benefit of priority to U.S. Provisional Application Ser. No. 60/939,887, filed May 24, 2007.

This Application is a continuation of and claims the benefit of priority to U.S. patent application Ser. No. 15/480,561, filed Apr. 6, 2017, now U.S. Pat. No. 9,795,376, which in turn is a continuation of and claims the benefit of priority to U.S. patent application Ser. No. 15/357,375, filed Nov. 21, 2016, now U.S. Pat. No. 9,700,301, which in turn is a continuation of and claims the benefit of priority to U.S. patent application Ser. No. 15/265,650, filed Sep. 14, 2016, now U.S. Pat. No. 9,597,071, which is a continuation of and claims the benefit of priority to U.S. patent application Ser. No. 14/796,642, filed Jul. 10, 2015, now U.S. Pat. No. 9,474,523, which is a continuation of and claims the benefit of priority to U.S. patent application Ser. No. 14/472,090, filed Aug. 28, 2014, now U.S. Pat. No. 9,451,948, which is a continuation of and claims the benefit of priority to U.S. patent application Ser. No. 13/361,444 filed Jan. 30, 2012, now U.S. Pat. No. 8,821,519, which is a continuation of and claims the benefit of priority to U.S. patent application Ser. No. 12/592,174, filed on Nov. 20, 2009, now U.S. Pat. No. 8,123,764, which is a continuation-in-part of and claims the benefit of priority to U.S. patent application Ser. No. 12/175,442, filed Jul. 17, 2008, now U.S. Pat. No. 7,976,555.

This patent application is a continuation of and claims the benefit of priority to U.S. patent application Ser. No. 15/480,561, filed Apr. 6, 2017, now U.S. Pat. No. 9,795,376, which in turn is a continuation of and claims the benefit of priority to U.S. patent application Ser. No. 15/357,375, filed Nov. 21, 2016, now U.S. Pat. No. 9,700,301, which in turn is a continuation of and claims the benefit of priority to U.S. patent application Ser. No. 15/265,650, filed Sep. 14, 2016, now U.S. Pat. No. 9,597,071, which is a continuation of and claims the benefit of priority to U.S. patent application Ser. No. 14/796,642, filed Jul. 10, 2015, now U.S. Pat. No. 9,474,523, which is a continuation of and claims the benefit of priority to U.S. patent application Ser. No. 14/472,090, filed Aug. 28, 2014, now U.S. Pat. No. 9,451,948, which is a continuation of and claims the benefit of priority to U.S. patent application Ser. No. 13/361,444 filed Jan. 30, 2012, now U.S. Pat. No. 8,821,519, which is a continuation of and claims the benefit of priority to U.S. patent application Ser. No. 12/592,174, filed on Nov. 20, 2009, now U.S. Pat. No. 8,123,764, which claims the benefit of priority to U.S. Provisional Application Ser. No. 61/200,180, filed Nov. 25, 2008.

Each of the aforementioned patent applications is incorporated by reference herein in its entirety for any purpose whatsoever.

FIELD

The embodiments disclosed herein relate to a medical device for suturing tissue, and more particularly to a device for the manipulation and control of a suturing needle during minimally invasive suturing, methods for making such a device and methods for using such a device for suturing tissue.

BACKGROUND

Minimally invasive surgery (MIS) has allowed physicians to carry out many surgical procedures with less pain and disability than conventional, open surgery. Unlike conventional open surgery, where the surgical site is readily accessible through a large incision, enabling the surgeon to easily visualize and manipulate both tissue and instruments, MIS requires the surgeon to operate remotely by inserting and manipulating instruments through small punctures ("keyhole surgery") or through natural orifices, including for example the vagina, the esophagus, or the anus.

In MIS, a small puncture is typically made in the body. Medical instruments are then inserted through a cannula. A cannula has a small inside diameter, typically 5-10 millimeters (mm), and sometimes up to 20 millimeters (mm) or more. A number of such cannulas may be inserted into the body for any given operation. Minimally invasive surgical instruments are necessarily smaller, and are also generally longer and therefore are more difficult to manipulate with precision.

Perhaps the most problematic surgical task in MIS is suturing. Suturing requires coordinated manipulation with both hands of small needles and sutures that are difficult to visualize (particularly when only indirect, two-dimensional video imaging is available) as well as the several instruments (including needle-drivers and pick-up forceps) ordinarily used to suture by hand. In an environment characterized by limited space, limited visualization, and limited mobility, many surgeons find minimally invasive suturing by hand an extremely difficult, often virtually impossible, surgical task.

In the preferred method of suturing by hand, a grasping forceps ("needle driver") is held by the surgeon and is used to grip a curved needle near the needle's tail. Pronation of the surgeon's wrist drives the needle into the tissue. When the point of the curved needle emerges from the tissue, the surgeon releases the needle from the grip of the needle driver and grasps the point with another forceps ("pick-ups"). The surgeon then pulls the curved needle by the needle point, preferably in a circular path following the arc of the needle's curvature to follow the most atraumatic path through the tissue, until the entire length of the needle has exited the tissue. Each time a stitch is placed, the curved needle is thus driven around in a complete circular arc. Individual (interrupted) stitches are placed by tying off the suture following placement of each stitch. Running (continuous) stitches are placed by repeatedly driving the curved needle in a complete circular arc repeatedly until the desired length of suture and number of stitches has been placed. In order to place additional interrupted or continuous stitches, the surgeon must let go of the point of the needle and re-grasp the needle near the needle's tail.

In the manual suturing technique described above, the direct handling of the needle can result in accidental needle pricks through a surgeon or nurse's gloves, posing a potential risk of infection for the surgeon, nurse, staff, and patient, or cause the needle to become contaminated with pathogenic bacteria that can cause onset of infection at the site of the sutures. There is also a risk of the needle penetrating internal organs or vessels and causing a serious, and often fatal infection.

Various devices for suturing for MIS are described in U.S. Pat. No. 5,643,295 entitled "Methods and Apparatus for Suturing Tissue"; U.S. Pat. No. 5,665,096 entitled "Needle Driving Apparatus and Methods of Suturing Tissue"; U.S. Pat. No. 5,665,109 entitled "Methods and Apparatus for Suturing Tissue"; U.S. Pat. No. 5,759,188 entitled "Suturing Instrument with Rotatably Mounted Needle Driver and Catcher"; U.S. Pat. No. 5,860,992 entitled "Endoscopic Suturing Devices and Methods"; U.S. Pat. No. 5,954,733 entitled "Suturing Instrument with Rotatably Mounted Needle Driver and Catcher"; U.S. Pat. No. 6,719,763 entitled "Endoscopic Suturing Device"; and U.S. Pat. No. 6,755,843 entitled "Endoscopic Suturing Device", all of which are incorporated by reference in their entireties for the teachings therein.

Assignees' U.S. Pat. No. 5,437,681, U.S. Pat. No. 5,540,705 and U.S. Pat. No. 6,923,819 disclose a suturing device with thread management comprising a protective cartridge, suturing needle and needle rotation drive, the disclosures of which are hereby incorporated by reference. The devices described in the above-mentioned patents and patent applications comprise a mechanism for driving a protected needle however, the needle is rotated about an axis that is parallel to the axis of the device. In addition, the orientation and size of the suturing device makes it difficult to visualize and cumbersome to use for MIS.

Therefore, there remains a need in the art for a minimally invasive suturing device that is easily manipulated within the small diameter of the cannula; functions in an environment characterized by limited space, limited visualization, and limited mobility; mimics the preferred method of suturing used by surgeons; permits the surgeon to secure and tie knots quickly and with controlled tension; places continuous stitches; and protects user's from accidental needle sticks during needle handling, as well as internal organs and vessels, from inadvertent needle-pricks.

SUMMARY

Devices and methods for minimally invasive suturing of tissue internal to a body are disclosed herein.

According to aspects illustrated herein, there is provided a medical device for closing openings internal to a patient's body, which closely emulates or replicates the manual suturing actions carried out by a surgeon. The device offers several advantages over conventional methods used by surgeons for suturing tissue during minimally invasive surgery in that the device provides a hand-held suturing instrument of relatively simple mechanical construction that requires no external motive source. The presently disclosed embodiments provide relative ease of operation for the surgeon with only one hand.

According to aspects illustrated herein, a suture head assembly may be removably attached to an actuator mechanism of the suturing device. The diameter of the device is small enough to fit into a typical cannula, thus making the device extremely easy to maneuver, as well as suture, during endoscopic or other MIS procedures. Also, the suture head assembly of the device can be laterally articulated to the left of center, to the right of center, up, and down, once inside the cannula, which is ideal for use in the course of endoscopic surgery, including laparoscopy, thoracoscopy and arthroscopy, as well as other less-invasive surgical procedures.

The device of the present disclosed embodiments closely emulates or replicates the manual suturing actions carried out by a surgeon. For example, during manual suturing by hand, the needle is held in forceps and travels in a circular arc with no obstructions anywhere in the interior of the arc. The design of the suturing device of the present disclosed embodiments allows for a lack of obstruction in the center of the arc of the needle during suturing. In other words, there is no hub at the center of the circular arc of the suturing needle. The entire area within the circular arc of the needle is unobstructed. This allows for the user to have better visualization during operation, unlike the present mechanical suturing methods, while maintaining control over needle movement.

In accordance with one embodiment a "locomotive-type" drive mechanism is provided for advancing the needle about a path of travel. This embodiment of a drive enables the small diameter of the device and affords better visualization during operation because of the lack of a hub. There are many benefits afforded by the design of the suturing device of the presently disclosed embodiments, including, but not limited to, more tissue being able to fit into the device, thus enabling a bigger bite of tissue and a more secure suture; the device can be used to ligate, that is, place a loop of suture around a blood vessel, duct, or other tubular structure; and the device can be inserted further into smaller incisions/ openings (one side of the aperture can be inserted deeply, for example).

A benefit provided by the suturing device of the presently disclosed embodiments is that the device enables maneuvering a suturing material through a tissue incision in a manner substantially similar to the way a surgeon would do so by hand. In particular, the suturing device first pushes a suturing needle from the tail of the needle and drives the point of the needle through the tissue. The device then picks up the point of the needle that passed through the tissue, and pulls the remainder of the suturing needle and the suture attached to the suturing needle through the tissue. The suturing needle thus consistently follows the arc of the needle's own curve, which is the preferred method of suturing, in the most atraumatic way of passing a needle through tissue. A benefit provided by the suturing device of the presently disclosed embodiments is the ability of the suturing needle to pull the suturing thread entirely through the tissue segments being closed, following each stitch. When using the suturing device of the presently disclosed embodiments, no ancillary instruments or tools such as needle holders, pick-up forceps or the like are needed to complete the stitch. A forceps can be used to tighten the knots.

According to aspects illustrated herein, there is provided a suturing device that includes a suturing needle that is protected by a housing, the suturing needle is not exposed to or handled directly by the user, thereby preventing inadvertent needle sticks. The configuration of the suturing device of the presently disclosed embodiments also protects against inadvertent penetration of internal organs or vessels by the needle, since the housing acts as a shield between the organs and the needle.

The suturing device of the presently disclosed embodiments is useful for suturing tissue internal to a body. An embodiment of the device includes an elongated barrel having a proximal end, a distal end, and a longitudinal axis therebetween; a suture head assembly extending from the distal end of the elongated barrel; a suturing needle having a pointed end and a blunt end, the suturing needle capable of rotating about an axis approximately perpendicular to a longitudinal axis of the elongated barrel, wherein the pointed end of the suturing needle is positioned within the suture head assembly prior to and after rotation of the suturing needle; and an actuator extending from the proximal end of the elongated barrel to actuate a drive mechanism having a needle driver for engaging and rotating the suturing needle.

According to aspects illustrated herein, there is provided a method for suturing tissue during minimally invasive surgery that includes: (a) engaging a cartridge to a suture head assembly at a distal end of a suturing device, the cartridge having a protective housing and a suturing needle with a pointed end and a blunt end; (b) introducing the distal end of the suturing device into a body cavity; (c) positioning an opening in the cartridge to span a plurality of separated tissue segments or a single tissue segment; (d) activating an actuator coupled to a drive mechanism that engages the suturing needle to cause rotational movement of the suturing needle about an axis approximately perpendicular to a longitudinal axis of the suturing device and advance the suturing needle through the plurality of separated tissue segments or the single tissue segment; (e) pulling a suturing material attached to the suturing needle through the plurality of separated tissue segments or the single tissue segment forming a stitch; and repeating steps (c) through (e) to cause a plurality of stitches to be placed through the separated tissue segments or the single tissue segment.

According to aspects illustrated herein, there is provided a method for suturing tissue during minimally invasive surgery that includes: (a) engaging a suturing needle with a pointed end and a blunt end to a suture head assembly at a distal end of a suturing device, the suture head assembly includes a curved track, whereby the suturing needle follows a curved path along the track during rotation of the suturing needle, and a latch that provides a protective housing for the suturing needle; (b) introducing the distal end of the suturing device into a body cavity; (c) positioning an opening in the needle holder assembly to span a plurality of separated tissue segments or a single tissue segment; (d) activating an actuator coupled to a drive mechanism that engages the suturing needle to cause rotational movement of the suturing needle about an axis approximately perpendicular to a longitudinal axis of the suturing device and advance the suturing needle through the plurality of separated tissue segments or the single tissue segment; (e) pulling a suturing material attached to the suturing needle through the plurality of separated tissue segments or a single tissue segment forming a stitch; and repeating steps (c) through (e) to cause a plurality of stitches to be placed through the separated tissue segments or a single tissue segment.

According to aspects illustrated herein, there is provided a method for suturing tissue during minimally invasive surgery that includes inserting a distal end of a suturing device having a suturing needle with a pointed end into a body; positioning the suturing needle to span a plurality of separated tissue segments; activating an actuator a first time causing the pointed end of the suturing needle to extend beyond a protective housing of a cartridge to engage the plurality of separated tissue segments; and activating the actuator a second time to cause the suturing needle to complete a revolution and pull a suture extending from the suturing needle through the plurality of separated tissue segments to form a stitch.

In addition to the advantages discussed above, the suturing device of the presently disclosed embodiments is relatively simple and cost efficient to manufacture. Therefore, the suturing device should find widespread suturing applications that include single stitches or continuous stitches, e.g. spiral, mattress, purse string, etc., that are required to close tissue incisions, attach grafts, or the like.

These and other advantages of the presently disclosed embodiments are illustrated through the embodiments described hereinafter. The presently disclosed embodiments accordingly comprise the features of construction, combination of elements and arrangement of parts that will be exemplified in the following detailed description.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIGS. 2A and 2B are views of the suture head assembly of the suturing device of FIG. 1. FIG. 2A is a perspective assembly view of the suture head. FIG. 2B is a cutaway perspective view of the suture head.

FIG. 4A shows the position of the suturing needle and drive mechanism in a "home" position prior to use or after a complete full cycle. FIG. 4B shows the position of the suturing needle and drive mechanism after one full actuation of the handle, where the suturing needle is in a "rotation" position.

FIG. 5A shows the relationship between the pawl and anti-rotate spring when the suturing needle is in the home position. FIG. 5B shows a close-up view of the anti-rotate spring.

FIG. 6A shows the position of the suturing needle and the pawl immediately after the user squeezes the handle. The user then releases the handle and the pawl returns to the start position (FIG. 6B) while the suturing needle remains in the rotation position.

FIG. 7A shows a close-up view of the pawl spring loaded with a spring. FIG. 7B shows a close-up view of the pawl, showing the heel and tip.

FIGS. 8 and 9 are side elevational views of a much larger scale of the internal portions of the drive mechanism located within the handle and elongated barrel. FIG. 8 shows the drive mechanism when the handle is in an open position and FIG. 9 shows the drive mechanism when the handle is in a closed position.

FIG. 10 shows a top view when the handle is in the open position. FIG. 11 shows a bottom view when the handle is in the open position. FIG. 12 shows a top view when the handle is in the closed position. FIG. 13 shows a bottom view when the handle is in the closed position.

FIG. 16 is a view showing the relation between the cartridge holder assembly, cartridge, latch and C-brace.

FIGS. 17A, 17B and 17C show the suture head assembly. FIG. 17A shows a side view of the suture head assembly. FIG. 17B is a close-up side view showing the relationship between the lever and latch during attachment and ejection of the needle and cartridge from the cartridge holder assembly. FIG. 17C shows a top view of the suture head assembly.

FIG. 20 shows a side view of the suture head assembly. FIG. 21 shows a bottom view of the suture head assembly. FIG. 22 shows a bottom view of the suture head assembly articulated to the left. FIG. 23 shows a bottom view of the suture head assembly articulated to the right.

FIG. 24 shows a perspective view of the suturing device with the handles in the open position. FIG. 25 shows a perspective view of the suturing device with the handles in the closed position.

FIGS. 27A and 27B are cutaway segmental views of the suture head assembly of FIGS. 24 and 25 showing interaction points of a suturing needle with a portion of the drive mechanism. FIG. 27A shows the position of the suturing needle and drive mechanism in a "home" position prior to use or after a complete full cycle. FIG. 27B shows another view of the suturing needle and drive mechanism.

FIG. 30 shows the suture head assembly with the latch in the open position. FIG. 31 shows the suture head assembly with the latch in the closed or locked position.

FIG. 34 shows a top view of the suture head assembly. FIG. 35 shows a side view of the suture head assembly.

FIG. 36 shows a top view of the front pulley and cable when the handle is in the open position. FIG. 37 shows a top view of the return pulley and cable when the handle is in the open position.

FIG. 50A is a sectional view of the second embodiment of the suture head assembly in which the pawl is at the proximal end of the engagement drive track, immediately proximal to the trailing notch of the needle.

FIG. 50C is a top view through section C-C of FIG. 50A showing how the flat spring is deflected, pressing the pawl against the side of the needle.

FIG. 51A is a sectional view of the second embodiment of the suture head assembly in which the pawl is within the trailing notch of the needle at the proximal end of the engagement drive track.

FIG. 51B is a view through section B-B of FIG. 51A showing how the flat spring is relaxed against the pawl when the pawl tip is within the notch of the needle.

FIG. 52 is a sectional side view of the second embodiment of the suture head assembly, showing the needle in the 'home' position, the anti-rotate spring engaging the needle, and the pawl within the trailing notch, in position to drive the needle through a suturing cycle.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Figure 1:
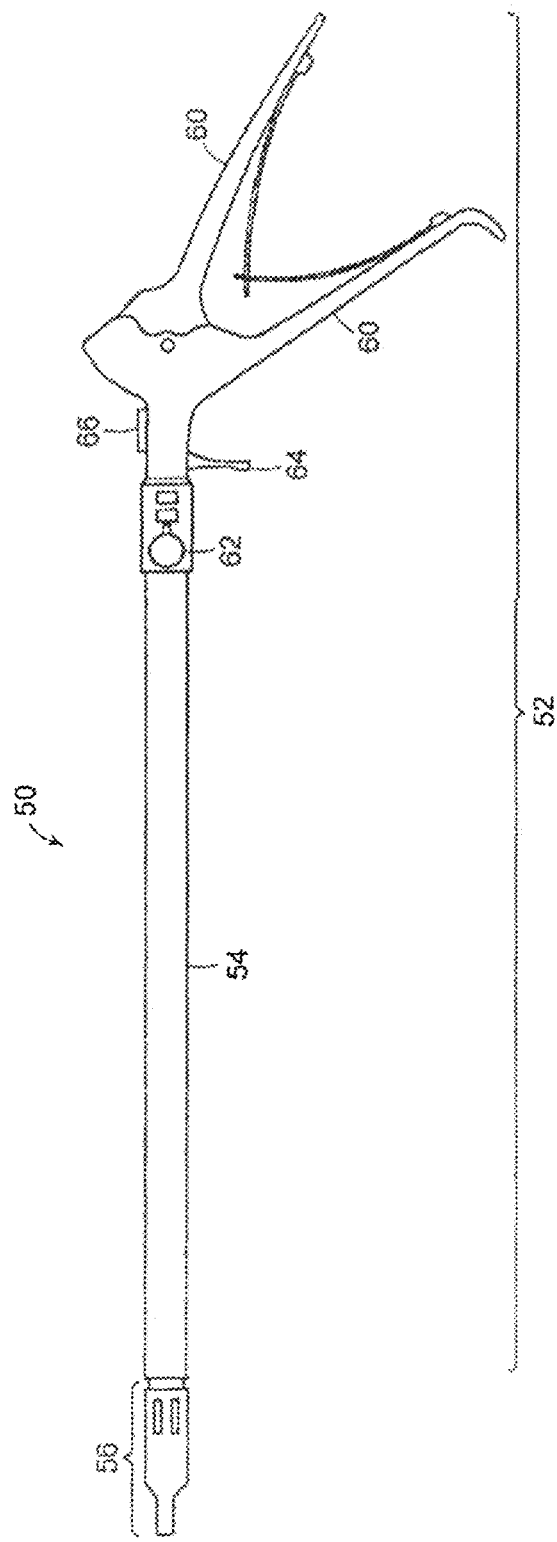
FIG. 1 is a perspective view of a suturing device of the presently disclosed embodiments.

The suturing device of the presently disclosed embodiments is shown generally at 50 in FIG. 1. Referring to FIG. 1, the suturing device 50 can be used to produce a continuous or interrupted stitch or suture so as to enable closure of openings internal to a patient's body. The suturing device 50 can be utilized to suture any type of anatomical tissue in any type of anatomical cavity; and, accordingly, while the device 50 is described hereinafter for use with a cannula in endoscopic procedures, such as laparoscopy, the device 50 can be used in open surgery and with catheters and other small and large diameter tubular or hollow, cylindrical members providing access to small cavities, such as veins and arteries, as well as large cavities, such as the abdomen.

In an embodiment suturing device 50 includes an actuator mechanism shown generally at 52 which comprises an elongated barrel 54 and a handle 60 that extends from the undersides at a proximal end of the elongated barrel 54. A suture head assembly 56 is attached to the distal end of the elongated barrel 54. In an embodiment, the suture head assembly 56 is removably attached to the distal end of the elongated barrel 54. The length of the suture head assembly 56 can range from about 20 mm to about 100 mm. In an embodiment, the length of the suture head assembly 56 is about 50 mm. The length of the elongated barrel 54 can range from about 50 mm to about 400 mm. Those skilled in the art will recognize that the elongated barrel 54 can be made shorter or longer depending on the intended use of the device 50. In an embodiment, the elongated barrel 54 is about 300 mm. In an embodiment, the elongated barrel 54 is about 350 mm. An articulation lever 66, just distal to the top of the handle 60 is pushed or pulled to cause the suture head assembly 56 to rotate. Moving the articulation lever 66 clockwise, moves the suture head assembly 56 to the right and moving the articulation lever 66 counterclockwise, moves the suture head assembly 56 to the left. The articulation lever 66 can also be moved to articulate the suture head assembly 56 up and down. The suture head assembly 56 is locked in place with a locking lever 64 located on an underside of the device 50, below the articulation lever 66. The suture head assembly 56 may be articulated, and the elongated barrel 54 may be any length appropriate for the intended clinical application of the device 50. The diameter of the device 50 can range from about 3 mm to about 20 mm. In an embodiment, the diameter of the device 50 is about 12 mm. In an embodiment, the diameter of the device 50 is about 3 mm. A flush port 62 is located on the side of the elongated barrel 54 in order to provide a port of entry for cleaning fluids or suction such that the device 50 can be cleaned prior to or after use.

The handle 60 is a grip that is squeezed in order to actuate the suturing device 50. The suturing device 50 is actuated by the actuator mechanism 52 coupled to a drive mechanism 70. The actuator mechanism 52 of the suturing device 50 may comprise a triggering mechanism that is known in the art, such as for example, the triggering mechanisms disclosed in U.S. Pat. Nos. 6,053,908 and 5,344,061, both of which are hereby incorporated by reference. Alternatively, the actuator mechanism can be either a manually operable button or switch, or a mechanically operable by an automated electrical or a fuel driven device, such as for example, an electrical, electromagnetic or pneumatic motor powered by electrical, electromagnetic, compressed air, compressed gas, hydraulic, vacuum or hydrocarbon fuels. Those skilled in the art will recognize that any actuator mechanism of any type known in the art can be within the spirit and scope of the presently disclosed embodiments.

The suturing needle (e.g., 120, 220) used with the suturing device 50 has an engagement or gripping surface at one or more locations along its length. By way of this surface, an engagement mechanism in the suture head assembly 56 can grip the needle to advance it through the target tissue. This gripping surface can take on a number of different forms, including, for example, one or more serrations or teeth raised above or depressed below the generally toroidal surface of the suturing needle, and properly oriented to allow the suturing needle to advance smoothly through tissue. In this case, the engagement mechanism in the suture head assembly 56 can include one or more number of interfitting teeth. The gripping or engagement surface of the suturing needle can also take the form of hatch marks engraved on the surface of the suturing needle, which either may be raised above or depressed slightly below the surface of the suturing needle. In this embodiment, the engagement mechanism in the suture head assembly 56 can comprise a rubberized contact surface, or a collapsible mesh that can surround the body of the needle at the gripping surface to apply a trapping force against the needle.

In a preferred embodiment, the gripping surface may include one or more notches that penetrate the surface of a suturing needle that is generally toroidal in shape, with the notches located on the outer circumference, inner circumference, or on one or both sides of the suturing needle. A corresponding engagement mechanism in the suture head assembly 56 can comprise a pawl, which can take many forms, but which at a minimum must effectively contact the leading or forward wall of a notch on the suturing needle, either to drive the needle in a forward direction, or to prevent the needle from moving in a reverse direction. The following description uses a particular embodiment of the gripping surface for illustrative purposes, and is not intended to limit the scope of the invention illustrated herein.

Figure 2A:
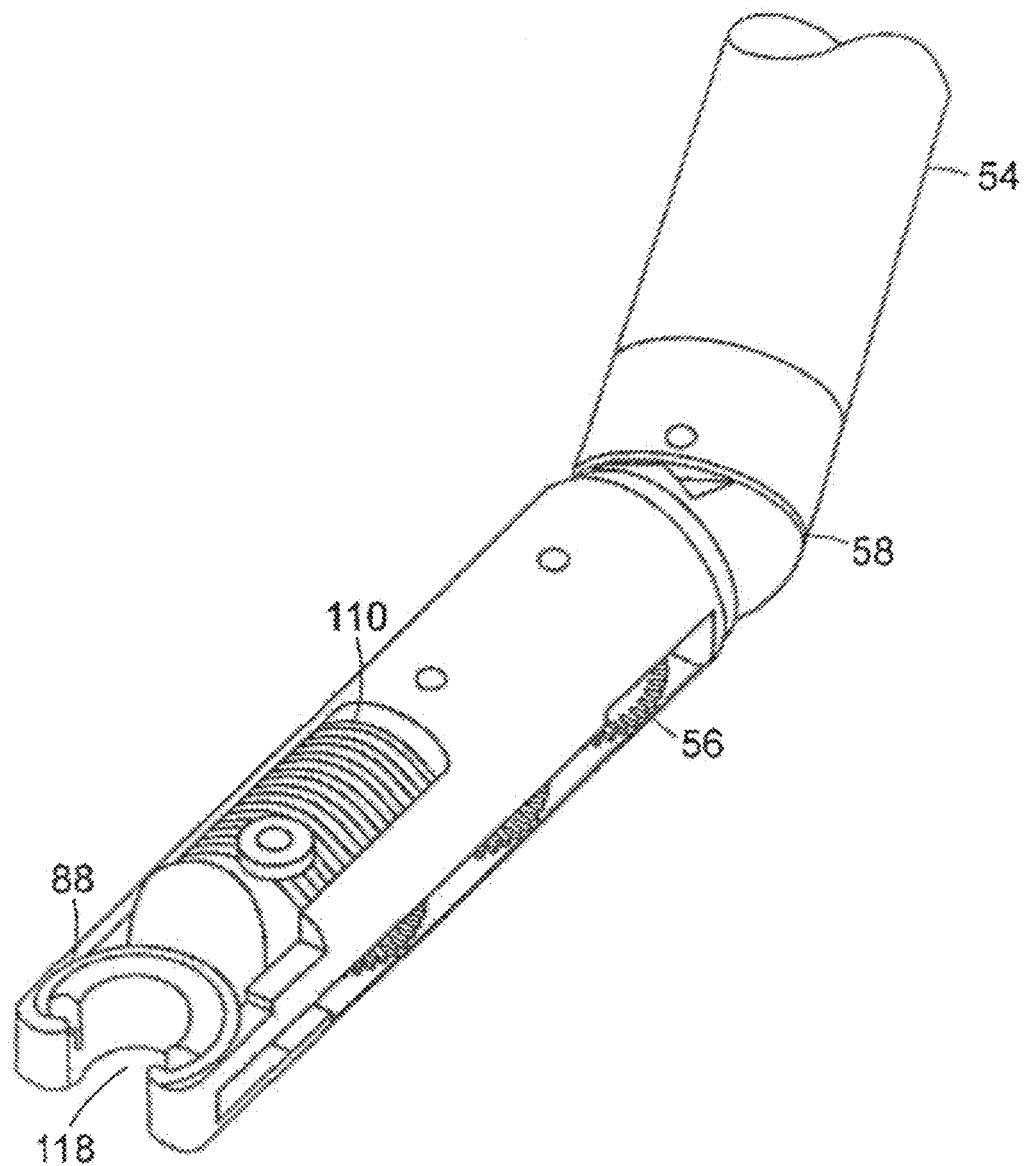

FIG. 2A is a perspective view of the suture head assembly 56 with a cartridge holder assembly 90 located at the distal end to which a cartridge 88 can be attached. In accordance with one embodiment, the suture head assembly 56 may be fabricated as a single piece. FIG. 2B is a perspective assembly view of the suture head assembly of the presently disclosed embodiments showing part of the drive mechanism 70, shown as a gear train/pulley system including pulleys 72, 74, 76 and 78. Located within the elongated barrel 54 are mechanical parts including drive shafts, belts, rods, cables, or hydraulic tubes which run from the elongated barrel 54 through the spherical portion 58 and then engages with the drive mechanism 70 in the suture head assembly 56. Connected at the proximal end of the suture head assembly 56 there is depicted a spherical portion 58 that contains part of the drive mechanism 70 including two idler pulleys 80 and cables 84 and 86. The spherical portion 58 resides within the distal portion of the elongated barrel 54 and rotates in a substantially frictionless fashion. In one embodiment, the drive mechanism 70 includes a gear train/pulley system ("locomotive-type" drive mechanism) and cables and rods that extend from the distal end of the suture head assembly 56 to the proximal end of the elongated barrel 54.

The suture head assembly 56 is that portion of the device 50 within which the mechanism for driving the curved needle 120 in a complete 360-degree circular arc, as well as the cartridge holder assembly 90 for attaching and releasing the cartridge 88 are situated. The suturing device 50 is unique in the fact that the orientation of the suture head assembly 56 is such that when the cartridge 88 is attached to the suture head assembly 56 the needle 120 is driven in a curved path about an axis approximately perpendicular to the longitudinal axis of the device 50. In this way, the needle 120 may be optimally visualized as the needle 120 is driven in a circular arc. Also, as shown in FIG. 2B, the needle 120 and cartridge 88 are in a plane parallel to the drive mechanism 70 and fit into the same space in the suture head assembly 56.

The improved visibility offered by the shape and configuration of the suture head assembly 56 enables precise device placement over the incision or other target tissue of interest, and uniform advancement of the suturing device 50 after every stitch to provide a uniform and symmetric suture, thereby minimizing the risk of tearing tissue and bleeding due to a stitch being positioned too close to the edge of the incised tissue. In one embodiment, the entire device 50 or parts of the device 50, such as the suture head assembly 56, the elongated barrel 54, the handle 60, and the needle 120 and cartridge 88, may be composed of a sterilizable medical grade plastic material, in which case, the entire device 50 or parts of the device 50 may discarded and disposed after a single use. In another embodiment, the device 50 may be composed of a sterilizable medical grade metallic material such as stainless steel to enable reuse subsequent to sterilization following a prior use. In still another embodiment, the device 50 is composed of a sterilizable medical grade metallic material such as titanium to enable reuse subsequent to sterilization following a prior use. The use of titanium is ideal for certain procedures including Magnetic Resonance Imaging (MRI) and Computed Tomography (CT) because they are X-Ray radiolucent and do not interfere with MRI and CT scans.

Figure 3A:
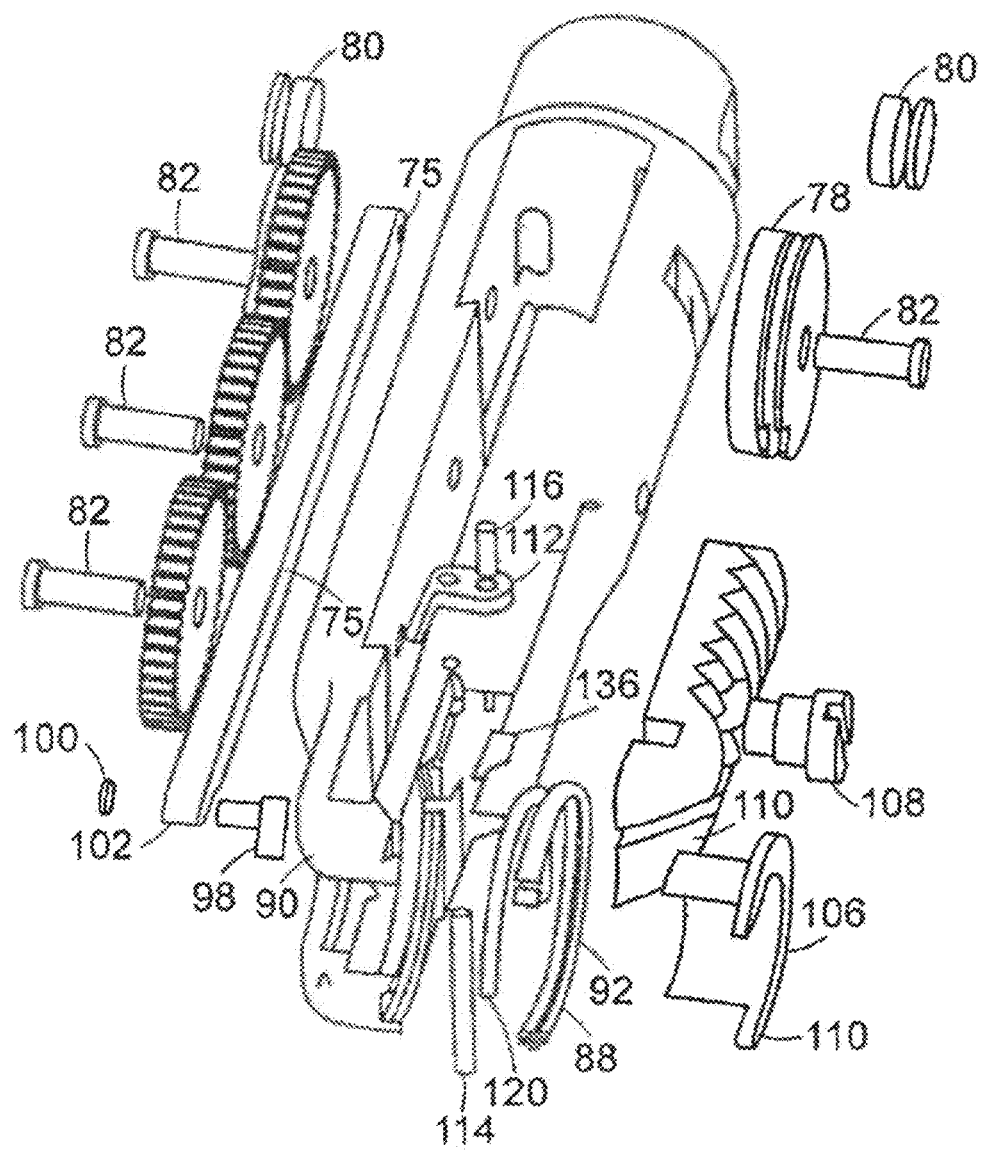
FIGS. 3A and 3B are segmented assembly views of the suture head assembly of FIG. 2.
Figure 3B:
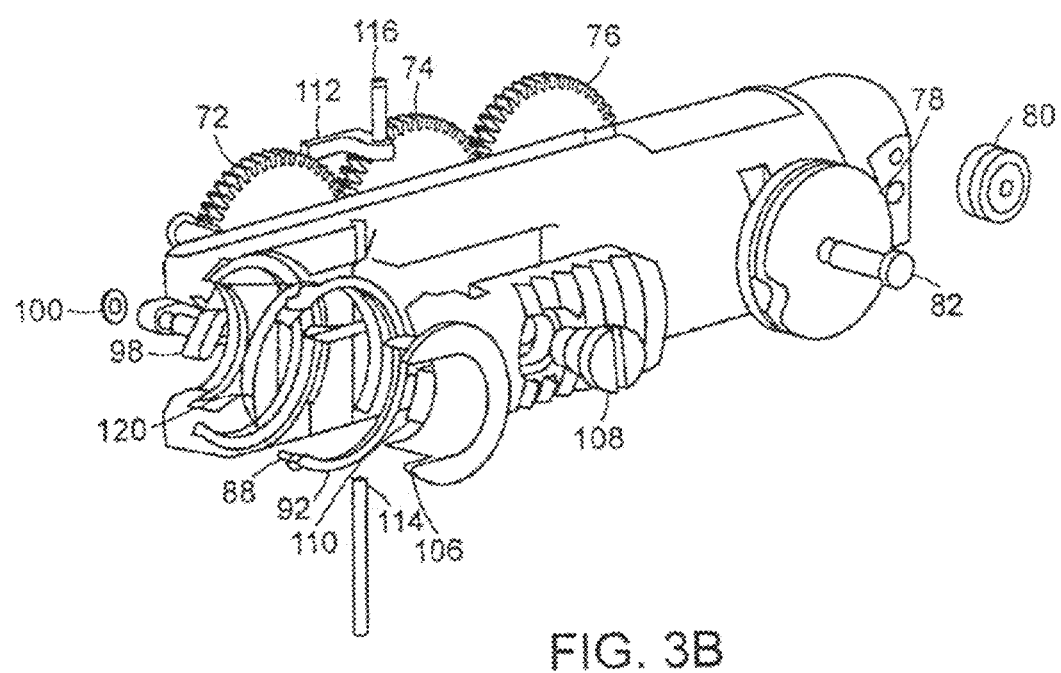
Figure 15:
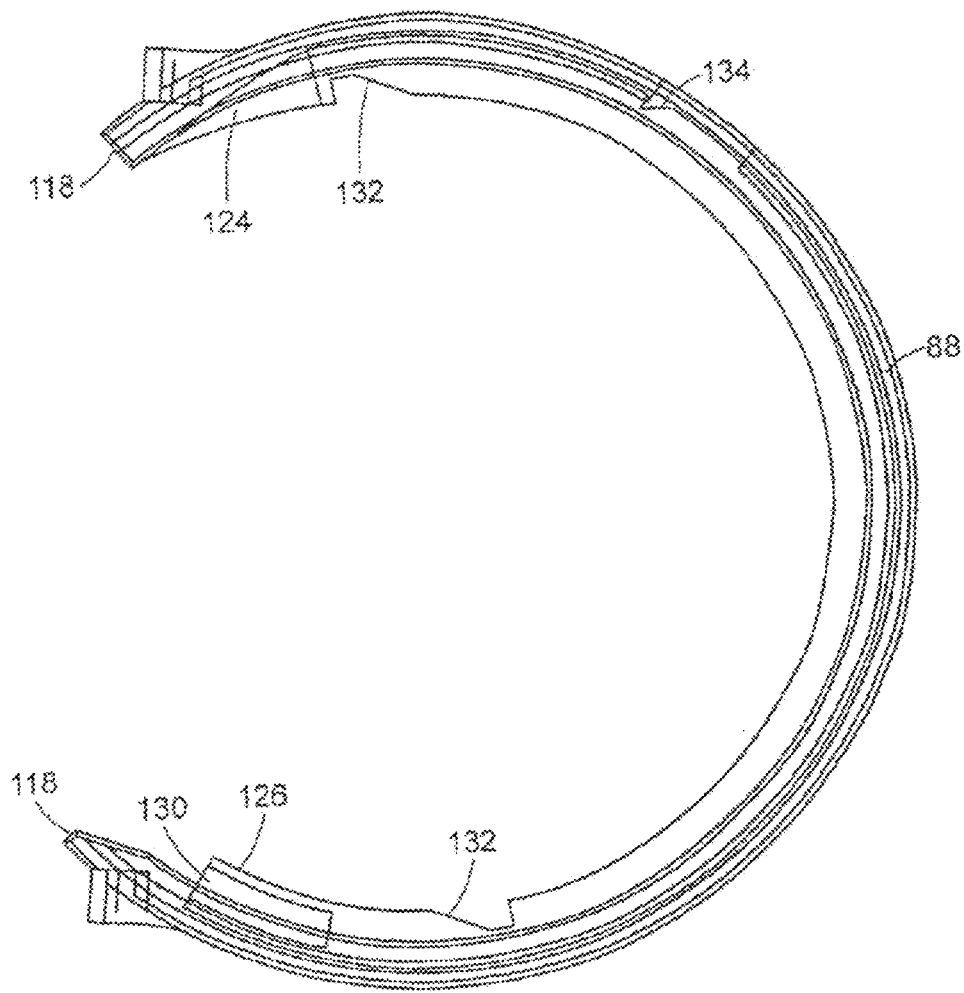
FIG. 15 is a view depicting the suturing needle positioned in the track of the cartridge.

FIGS. 3A and 3B provide detailed segmental views of the suture head assembly 56 showing the cartridge holder assembly 90, the disposable needle cartridge 88, a curved suturing needle 120, and parts of the drive mechanism 70 including a plurality of pulleys, 72, 74, 76, 78 and 80 involved in driving the needle driver 98 through a semicircular path. In one embodiment, the needle driver is a pawl 98. As depicted, a shoulder screw 108 is used to keep a latch 110 locked in place over the disposable cartridge 88 and the suturing needle 120. Pulleys 72, 74, 76 and 78 are engaged with an actuator arm 102, which is attached to the pawl 98. The pawl 98 interfits with two notches 132 (as depicted in FIG. 15) located on the needle 120 at 180 degrees apart from each other which drives the curved needle 120 in a completely circular arc. The suture head assembly 56 is preferably configured so that the pawl 98 (or other needle driver), does not intrude into or obstruct the area within the curve of the needle 120. The entire area within the circular arc of the needle 120 is unobstructed; there is no hub at the center of the circular arc so that the device 50 can encompass the maximum volume of tissue within the circular arc of the curved needle 120. In this way, the needle 120 may be rotated through a relatively large arc, allowing the needle 120 to obtain a sufficient "bite" into the tissue. Preferably, the needle 120 will have a radius of curvature of about 3 mm to about 40 mm. In an embodiment, the device 50 sutures within the limit of the diameter of the suture head assembly 56, which is advantageous to suturing through small cannulas during minimally invasive surgery. In an embodiment, the diameter of the curved needle 120 does not exceed the diameter of the suture head assembly 56.

Figure 4A:
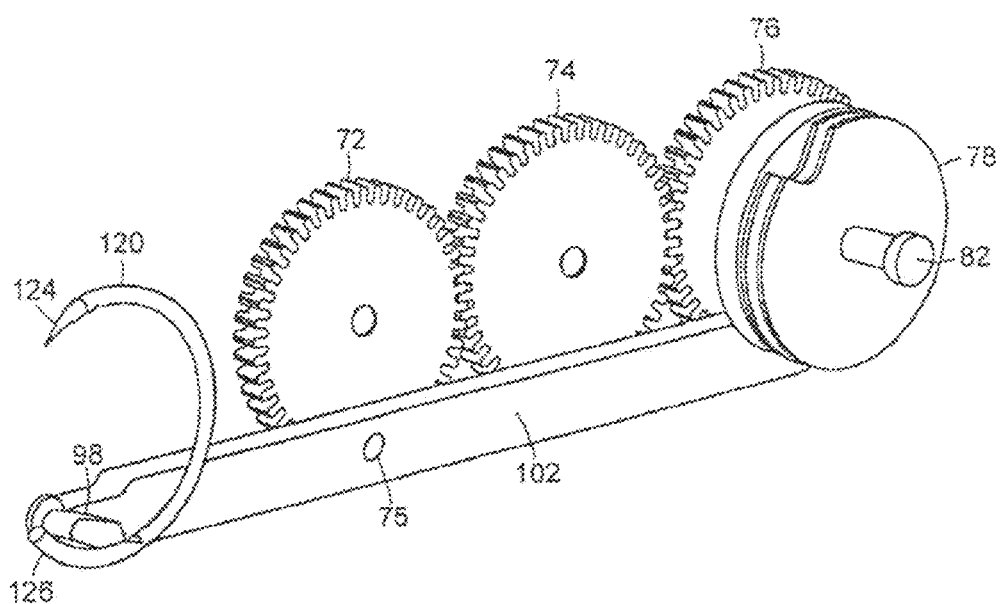
FIGS. 4A and 4B are cutaway segmental views of the suture head assembly showing interaction points of a suturing needle with a portion of the drive mechanism.
Figure 4B:
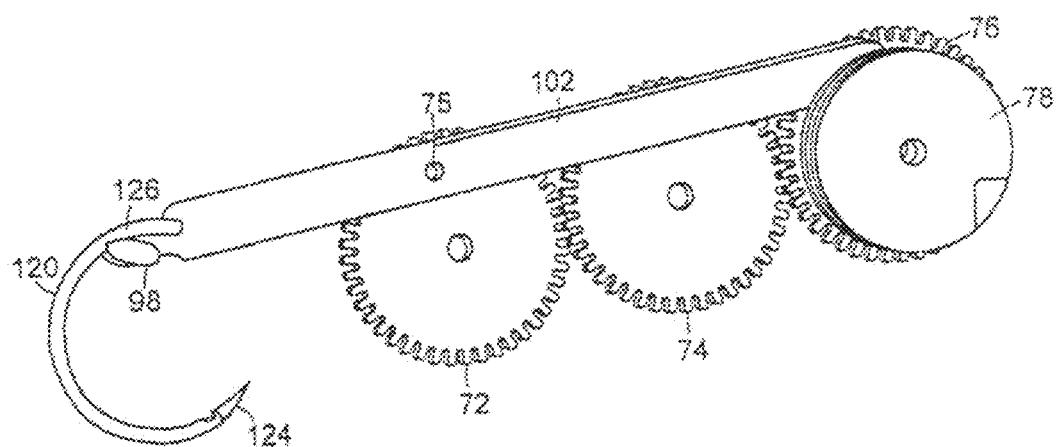

FIGS. 4A and 4B show detailed views of the drive mechanism 70 located in the suture head assembly 56 with respect to driving the needle 120 during use of the device 50 (the cartridge housing 88 has been removed to show the drive mechanism 70 in detail). The drive mechanism 70 includes a plurality of pulleys, 72, 74, 76 and 78, and the associated axle pins 82, involved in driving the pawl 98 through a semicircular path. The actuator arm 102 engages pulleys 72 and 76 and are pinned 75 to pulleys 72 and 76. As pulleys 76 and 78 rotate with the motion of the cables 86 and 84, respectively, which reside in the elongated barrel 54 (not shown), pulley 74 acts as an idler pulley, transferring the motion to the most distal pulley 72. Pulley 72 and pulley 76 rotate through identical arcs. The actuator arm 102 provides a connection to the pawl 98. The pawl 98 is located in the distal end of the actuator arm 102. The pawl 98 is attached to the actuator arm 102 by an integral shaft and collar 100 that fits loosely into the actuator arm 102 allowing smooth movement. As the handle 60 is closed and opened, the pawl 98 moves through the same arc as pulleys 72 and 76. The pawl 98 at the distal end of the actuator arm 102 is capable of engaging the notches 132 located along the radially inner edge of the needle 120. The actuator arm 102 is activated by the user upon squeezing of the handle 60, and is capable of sweeping back and forth in an arc spanning about 190 degrees or more. FIG. 4A shows a detailed view of the drive mechanism 70 and the suturing needle 120 either prior to using the device 50 or after one complete full cycle of the device 50. FIG. 4B shows a detailed view of the drive mechanism 70 and the suturing needle 120 after one squeeze of the handle 60. As shown, the drive mechanism 70 has moved in a circular arc greater than about 180 degrees, (about 190 degrees), while the suturing needle 120 has moved in a circular arc of about 190 degrees to drive through the tissue or vessel to be sutured.

Figure 7:
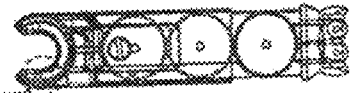
FIG. 7, including

The outer surface of the actuator arm 102 is shaped to accommodate a C-brace (shown as 106 in FIG. 7) that causes the pawl 98 to engage the needle 120 and thereby remain in contact. The advancing movement of the needle 120 during operation causes the notches 132 along the radially inner edge of the needle 120 to align with the pawl 98 in the actuator arm 102, thereby causing the pawl 98 to engage the notches 132 due to a positive pressure exerted by the C-brace (not shown), and to "lock" into the notches 132. The rotary advancing movement of the needle 120 is therefore controlled to occur sequentially through about 190 degrees each time the needle is actuated.

Figure 5:
FIG. 5, including
Figure 5A:
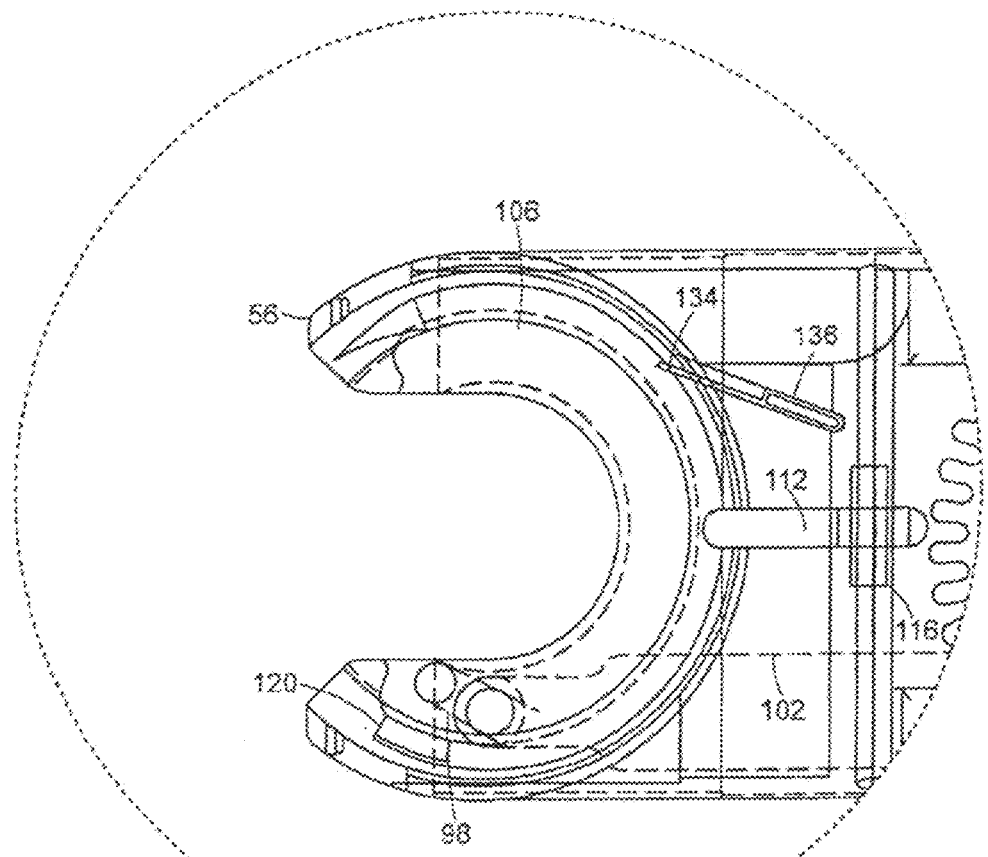
FIGS. 5A and 5B are expanded views of the working end of the suture head assembly with a suturing needle in the home position.
Figure 6A:
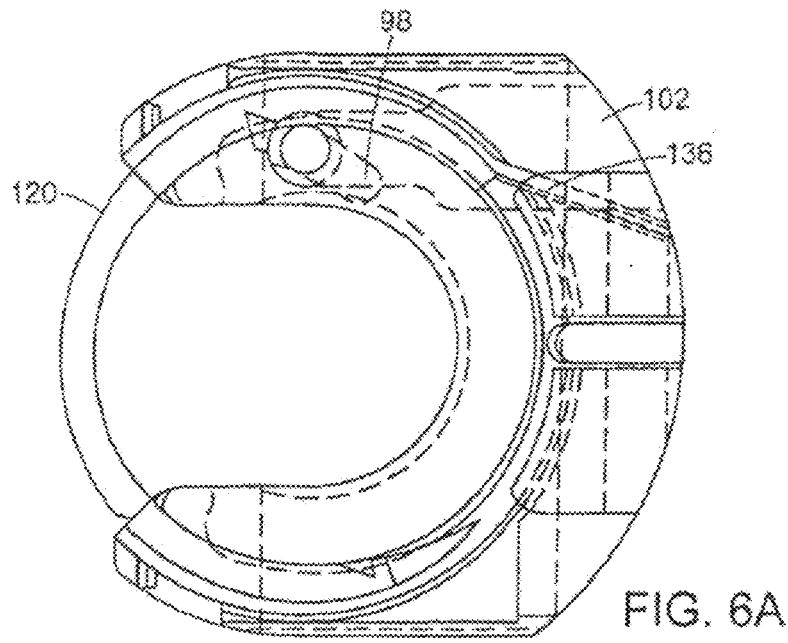
FIGS. 6A and 6B are expanded views of the working end of the suture head assembly during use of the device.
Figure 6B:
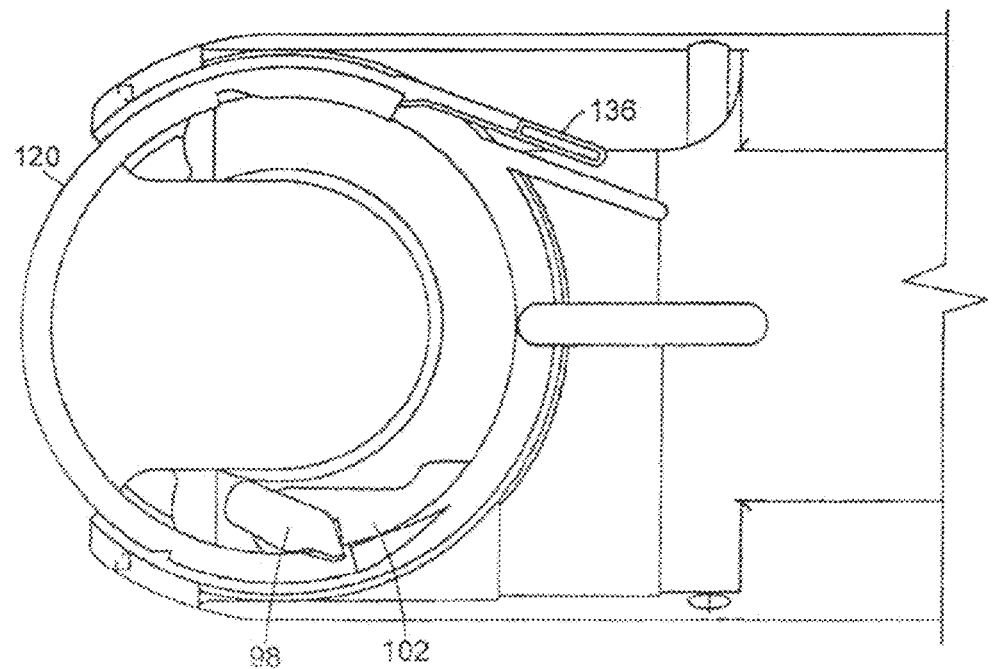

FIG. 5A shows a close-up view of the distal end of the suture head assembly 56 with the cartridge 88 and the needle 120 in view as well as the relationship between the pawl 98 and the actuator arm 102 with respect to the needle 120. The needle 120 is enclosed within the cartridge 88, so the sharp pointed end 124 is not exposed. This needle position, as loaded, is referred to as the "home" position (FIG. 5A). In the home position, the needle 120 is fully contained within the cartridge housing 88 to eliminate needle-pricks during handling of the cartridge 88 or the loaded device. Squeezing the device handle 60 fully, two times, operates the device 50 through one full cycle. As shown in FIG. 6A, the first full actuation of the handle 60 drives the needle 120 through an about 190 degree arc. The pointed end of the needle 124 exits the protective enclosure of the cartridge 88, drives through the tissue to be sutured, and re-enters the protection of the cartridge 88 of the device 50. This position, after the first squeeze of the handle 60, is referred to as the "rotation" position. As shown in FIG. 6B, the handle 60 is then released, and the needle 120 remains in the rotation position while the pawl 98 and the actuator arm 120 return to their start position. The handle 60 is then squeezed again driving the needle 120 through an about 190 degree arc and returning the needle 120 to the home position.

Figure 5B:
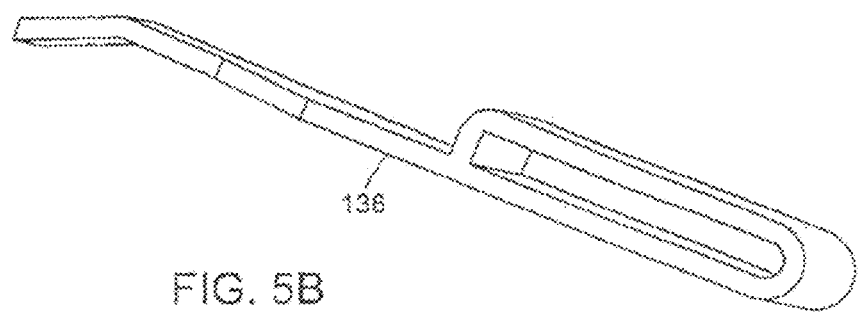

FIG. 5A shows the needle 120 in the home position, the pawl 98 is engaged in the notch 132 near the suture end of needle 126. An anti-rotate spring 136 is engaged in the notch 134 on the outer surface of the needle 120, not allowing the needle 120 to move backwards in the cartridge 88 of the device 50. A close-up view of the anti-rotate spring 136 is shown in FIG. 5B. In an embodiment, the needle 120 comprises at least one anti-rotate notch 134 and is engaged with at least one anti-rotate spring 136. As the pawl 98 drives the needle 120 through a first semi circular arc, the anti-rotate spring 136 slips out of the notch 134 and slides over the outer surface of the needle 120. As the pawl 98 reaches the end of a first drive stroke, the anti-rotate spring 136 snaps in behind the rear corner of the needle 120, near the suturing material or thread 146 (see FIG. 6A). As the pawl 98 returns to the start position, the anti-rotate spring 136 holds the needle 120 in place, preventing the needle 120 from moving with the pawl 98 back toward the start position. The pawl 98 returns to the start position and engages the notch 132 in the needle 120 near the pointed end 124 (see FIG. 6B). When the handle 60 is squeezed a second time, the needle 120 is driven back to the home position.

The width of the aperture 118 in the cartridge 88 is comparable to and corresponds with the width of the gap in the needle 120 so that when the needle 120 is in the home position (as shown in FIG. 5A) the needle 120 does not project materially into the aperture 118. Such an alignment causes the needle 120 to reside entirely within the cartridge 88, thereby preventing inadvertent contact of the sharp pointed end 124 with the user's fingers during handling of the disposable needle cartridge 88 for placement on the cartridge holder assembly 90 or disposal after use, and while operating the suturing device 50. Such protection of the needle 120 in the suturing device 50 prevents accidental "needle-pricks" from occurring, thereby substantially reducing the risk of infection caused by pathogenic bacteria or viruses that may contaminate the needle 120 during or after use prior to disposal. The needle 120 may be rotated in a curved track 92 of the cartridge 88 about the longitudinal axis of the suturing device 50 to advance the pointed needle end 124 so that the needle 120 first spans the aperture 118 and then returns to the home position. The suturing material or thread 146 is attached to the needle 120, and therefore follows the path of the needle 120. The suturing material or thread 146 may then be cut and secured by an appropriate method, such as for example, by tying, or additional stitches may be placed along the entire wound or incision by repeating the aforementioned process. Every stitch, whether a single, interrupted stitch, or one of a series of continuous, running stitches may be placed in like manner. The suturing device 50, therefore, may be used to insert either a single stitch, or to insert a suture comprising a plurality of continuous stitches as a replacement method for a more tedious and time-consuming manual suturing process. The terminal end of the suturing material or thread 146 may contain a knot or button to prevent the suturing material or thread 146 from pulling through the sutured tissue during placement of the first stitch. In an embodiment, the cartridge 88 comprises the suturing needle 120 attached to the terminal end suturing material or thread 146, and an appropriate length of suturing material or thread 146 are all packaged in a sterilizable medical packaging material.

Figure 7A:
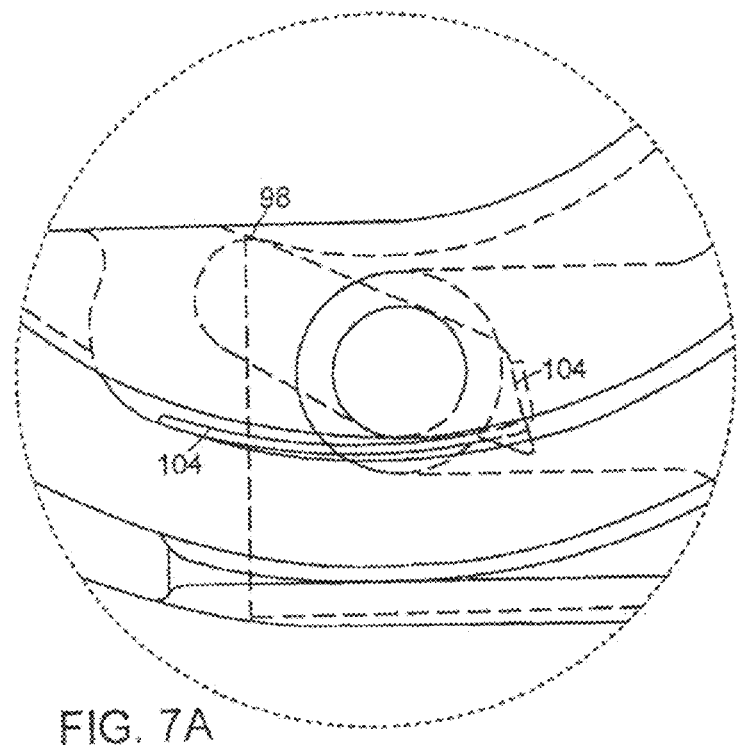
FIGS. 7A and 7B are expanded views of the pawl in contact with the C-brace while driving the suturing needle.
Figure 7B:
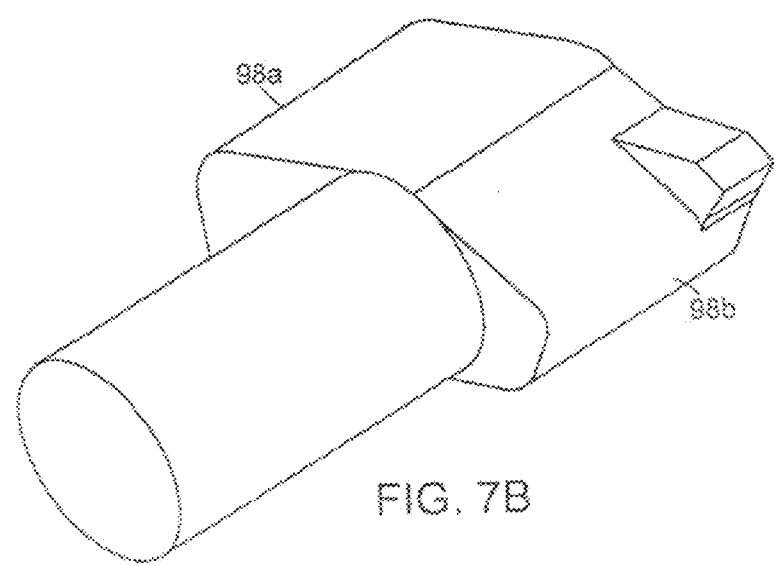

FIG. 7A shows a close-up view of the pawl 98 which rides in a track formed by the C-brace 106 and the suture head assembly 56. The pawl 98 is spring loaded with a spring 104. The spring 104 is engaged to the tip of the pawl 98b as shown in FIG. 7A. The spring 104 engages the pawl tip 98b into the notch 132 in the needle 120 during the driving stroke of the device 50 when the handle 60 is closed. The spring 104 also allows the tip of the pawl 98b to rotate out of notch 132 of the needle 120 during the return of the pawl 98 to the start position when the handle 60 is opened. The heel of the pawl 98a stays in contact with the C-brace 106 during the driving stroke of the device 50, preventing the pawl 98 from over-rotating and locking the needle 120. FIG. 7B shows a close-up view of the pawl 98 showing the pawl heel 98a and the pawl tip 98b.

Figure 9:
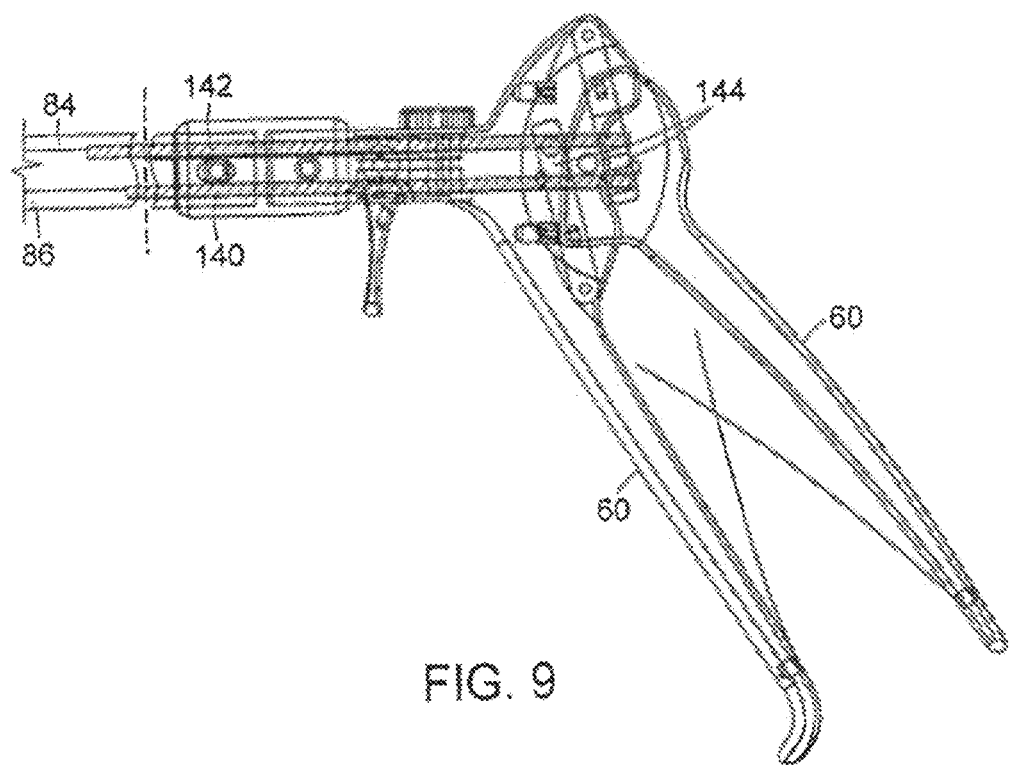

Referring now to FIGS. 8 and 9 in conjunction with FIG. 1, the user introduces the distal end portion of suturing device 50 into a body cavity, via a cannula assembly (not shown), and then laterally articulates the suture head assembly 56 using the articulation lever 66 located just distal to the top of the handle 60. The suture head assembly 56 is then positioned relative to the tissue/vessel to be sutured, and the user locks the suture head assembly 56 in place using the locking lever 64. The user then, through manipulation of suturing device 50, positions a plurality of separated tissue segments into the opening defined at the distal end portion of the suture head assembly 56 and within the aperture of the cartridge 118. The user, using only one hand, may manipulate the device 50 while actuating the handle 60 to close an incision with a continuous suture whose stitches may be individually tensioned precisely and uniformly along the length of the suture similar to suturing done by hand in the conventional way. The user may employ a single suture which would extend the entire length of the incision or multiple sutures.

The device 50 starts with the needle 120 in the home position and the handle 60 fully open (see FIG. 8). In an embodiment, the handle 60 is made up of a grip which rests in the user's palm and is squeezed in order to actuate the device 50. To drive the needle 120 through the tissue to be sutured, the user squeezes the handle 60 moving the needle 120 from the home position to the rotation position. The handle 60 contains linkages 144 to both the upper drive rod 142 and the lower drive rod 140. Squeezing the handle 60 (see FIG. 9) causes the two drive rods 140 and 142 to move in opposite directions. The upper drive rod 142, moves forward while the lower drive rod 140 moves backward. The drive rods are connected to the suture head assembly 56 with cables 84 and 86 and idler pulleys 80. The upper rod 142 is connected to pulley 78 with cable 84. The lower rod 140 is connected to pulley 76 with cable 86.

Figure 10:
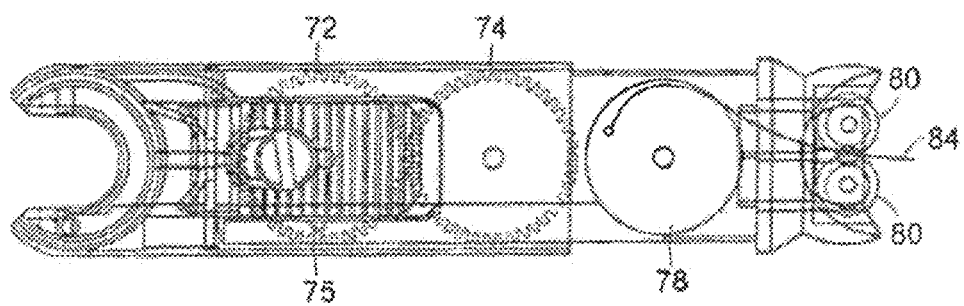
FIGS. 10-13 are top and bottom views of the suture head assembly, including cables that provide the connection between the drive mechanism located in the suture head assembly and the elongated barrel when the handle is in the open and closed positions.
Figure 11:
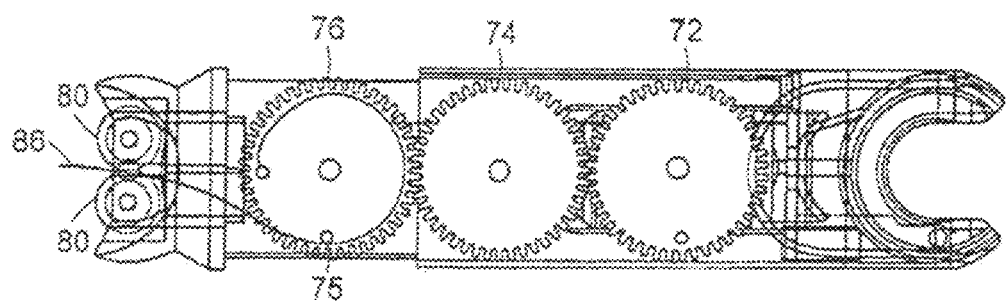
Figure 12:
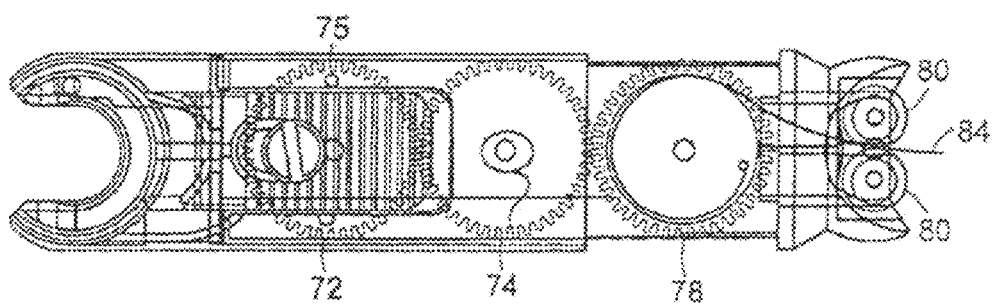
Figure 13:
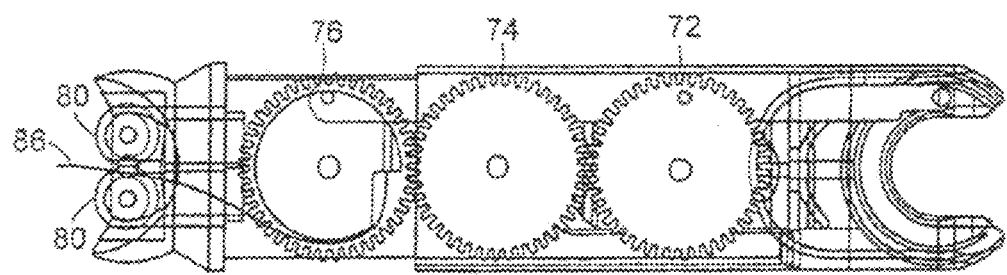

FIGS. 10 and 11 in conjunction with FIG. 8, show the connections and positions of cables 84 and 86 and the drive pulleys 72, 74, 76 and 78 when the handle 60 is in the open position. FIGS. 12 and 13 in conjunction with FIG. 9, show the connections and positions of cables 84 and 86 and the drive pulleys 72, 74, 76 and 78 when the handle 60 is in the closed position. The force to move needle 120 from the home position to the rotation position comes from the lower rod 140 pulling backward on the drive cable 86. The lower rod 140 extends nearly the full length of the elongated barrel 54, connecting to drive cable 86, at the proximal end of the elongated barrel 54. As shown in FIG. 11, cable 86 exits the elongated barrel 54 and enters the suture head assembly 56, passing over an idler pulley 80 located in the spherical portion 58, then wrapping clockwise (as viewed from the bottom) around pulley 76 and is secured to pulley 76 located in the suture head assembly 56. The pulling action of cable 86 causes pulley 76 to rotate through an arc of approximately 190 degrees. As lower rod 140 pulls backward, the upper rod 142 moves forward. The upper rod 142 also extends nearly the full length of the elongated barrel 54, connecting to drive cable 84, at the proximal end of the elongated barrel 54. As shown in FIG. 10, cable 84 also exits the elongated barrel 54 and enters suture head assembly 56, passing over a second idler pulley 80 located in the spherical portion 58, then wrapping (clockwise as viewed from the top) around pulley 78 and is secured to pulley 78 located in the suture head assembly 56. Pulley 78 is directly linked to pulley 76 through the actuator arm 102, and cables 84 and 86 are wrapped in opposing directions, so that as cable 86 unwinds from pulley 76, cable 84 winds onto pulley 78.

Figure 14:
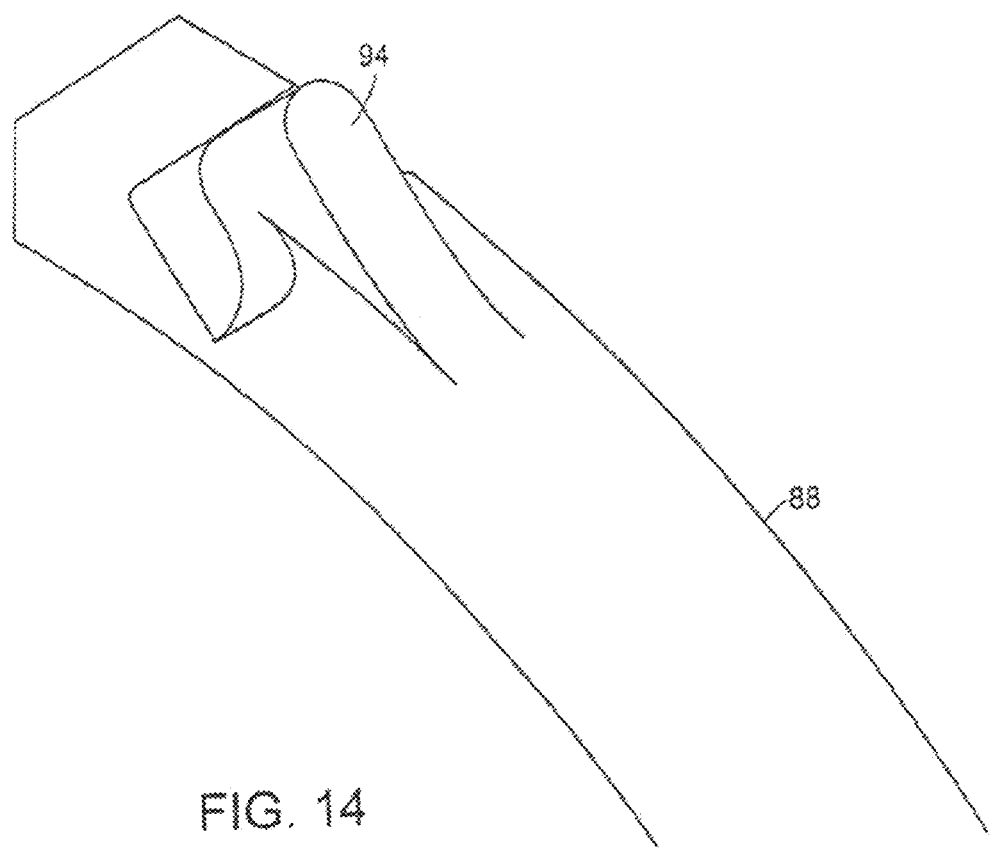
FIG. 14 is a close-up view of the cartridge holder with a tab that locks into a mating groove on the cartridge holder assembly.

The needle 120 is held in a path of rotation by a combination of three components. The cartridge 88, the C-brace 106 and the cartridge holder assembly 90 interact to constrain the needle 120 to the path of rotation (see FIG. 5). The cartridge 88 is a semicircular shaped component that is held into the device 50 by a plurality of extensions 94 located on each end of the cartridge 88 (see FIGS. 14 and 15). In an embodiment, the plurality of extensions 94 takes the form of tabs. In an embodiment, the cartridge 88 is made from a sterilizable medical grade metallic material such as stainless steel. The cartridge 88 provides some of the support structure for keeping the needle 120 in a rotational path and therefore should be constructed from a material with structural integrity. Those skilled in the art will recognize that any high-strength medical grade material may be used to fabricate the cartridge 88, such as a high-strength plastic. In an embodiment, the plurality of extensions are tabs extending from the cartridge housing 88. The plurality of extensions 94 lock into mating grooves 96 located along on the distal edge of the cartridge holder assembly 90 that are located diametrically opposite to one another, and are capable of engaging the plurality of extensions 94 correspondingly located in the needle cartridge housing 88 as shown in FIG. 16.

The proximal end of cartridge 88 is held in place by a cartridge holder assembly 90, as shown in FIG. 17A. The cartridge holder assembly 90 also includes a latch 110, a lever 112, associated pins 114 and 116, a shoulder screw 108, an anti-rotate spring 136 and at least one groove 96 that can engage with the plurality of extensions 94 located on the cartridge 88. It is the interaction of all of the elements of the cartridge holder assembly 90 that hold and lock the cartridge 88 in place. The latch 110 slides back to release the cartridge 88 and forward to lock the cartridge 88 in place. The latch 110 also has a built into ejector feature, as shown in FIG. 17B. A lever 112 is located distal and below the needle 120 and the cartridge 88. The lever 112 pivots on a pin 114. A second pin 116 located above the pivot pin 114, engages with a slot in the latch 110. To release the needle 120 and the cartridge 88, the latch 110 is pulled back and the lever 112 is rotated up and back, causing pin 116 to move back with the latch 110 and to rotate about pin 114 thus pushing the needle 120 and the cartridge 88 from the cartridge holder assembly 90. The needle 120 and the cartridge 88 are then removed from the device 50 by a slight proximal motion to disengage the plurality of extensions 94 from their mating grooves 96 in the cartridge holder assembly 90. FIG. 17C shows the needle 120 as it is driven through a first semi circular arc (the handle 60 has partially completed a first full squeeze). As the pawl 98 drives the needle 120 through a first semi circular arc, the anti-rotate spring 136 slips out of the notch 134 and slides over the outer surface of the needle 120.

Loading of the needle 120 and the cartridge 88 is accomplished by engaging the plurality of extensions 94 into both grooves 96 on the cartridge holder assembly 90 and then pressing the proximal ends down against the sloped distal surface of the latch 110. The latch 110 is spring loaded at the proximal end, thus can slide back as the needle 120 and the cartridge 88 are pressed into place and then snap closed to the locked position, retaining the needle 120 and the cartridge 88. The lever 112 is down and out of the way of the operation of the needle 120 and the cartridge 88.

Figure 18:
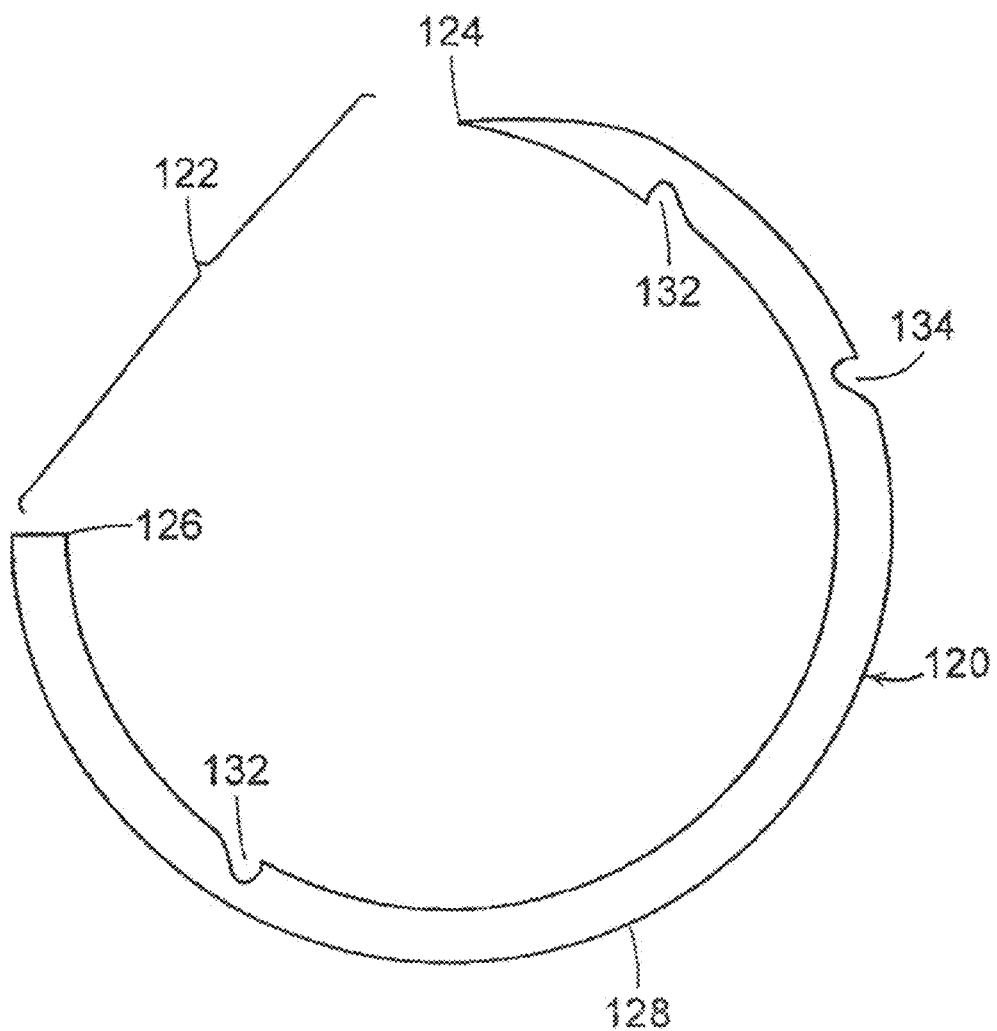
FIG. 18 is an expanded view of a curved suturing needle with notches depicted on the surface of the needle.
Figure 19A:
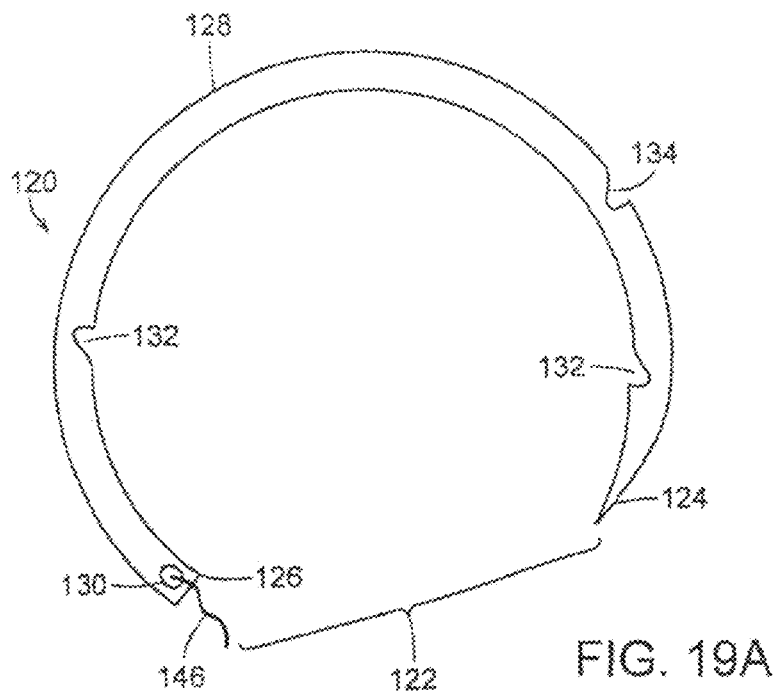
FIGS. 19A and 19B depict two exemplary embodiments of the curved suturing needle.
Figure 19B:
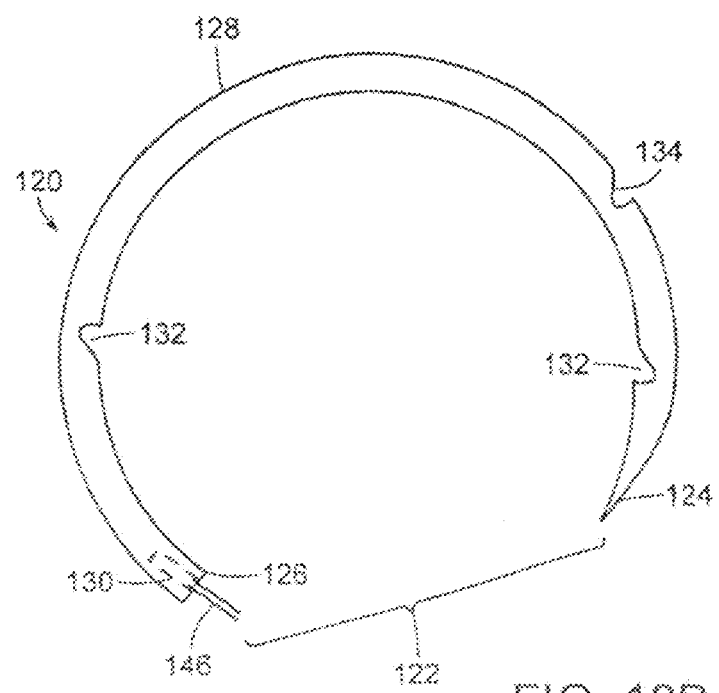

FIG. 18 shows a close-up view of the needle 120. The two notches 132 are located about 180 degrees apart on the inner surface and assist in driving the needle 120. The pawl 98 engages the notches 132 when driving the needle 120 through the circular motion. A third notch 134 is located on the outer surface of the needle 120. The notch 134 assists in preventing rotation of the needle 120 and provides an anti-rotation feature. In an embodiment (see FIGS. 19A and 19B), the needle 120 is formed as a circular split ring with a gap 122, a sharp, pointed end 124, and a blunt end 126. The needle 120 further comprises an opening 130 to accommodate the leading end of the suturing material or thread 146. In one embodiment, the opening 130 is the form of an eye though which the leading end of the suturing material or thread 146 may be passed through for attachment to the needle 120. In the illustrated needle 120 (FIG. 19A), the opening 130 is located adjacent to the blunt end 126. The opening 130 however, can be positioned anywhere along the arc or the needle 120 between the apex 128 and the blunt end 126. In another embodiment (FIG. 19B), the needle 120 comprises an opening 130 in the form of a cylindrical bore aligned axially with respect to the needle 120, located at the blunt end 126 (FIG. 19B). The leading end of the suturing material or thread 146 is inserted into the opening 130 and restrained by mechanically crimping. To enable the needle 120 to penetrate tissue to a required depth, the arc length of the needle 120 is preferably about 240 degrees to about 300 degrees. The needle 120 comprises two symmetric notches 132 along the radially inner edge ("inner notches") that are positioned proximally to the sharp, pointed end 124 and the blunt end 126 of the needle 120. The notches 132 are located directly opposite to each other, each having a perpendicular (about 90 degree) segment and an angular segment that makes an angle of about 60 degrees with the perpendicular segment. The inner notches 132 are engaged by the needle driver 98 of the drive mechanism 70 and enable the needle 120 to undergo a rotary movement upon actuation of the drive mechanism 70, thereby causing the needle 120 to penetrate into and advance through tissue. A similar triangular notch 134 is located on the radially outer edge ("outer notch") of the needle 120 proximally to the inner notch 132 closer to the sharp, pointed end 124. The outer notch 134 engages with the anti-rotate spring 136 located on the cartridge holder assembly 90, whereby rotation of the needle 120 in a direction opposite to the advancing direction or "needle backing-up" is prevented. The positive engagement of the needle outer notch 134 during operation of the suturing device precludes needle 120 from straying out of sequence during the suturing process.

The suture head assembly 56 of the device 50 can be laterally articulated to the left of center and also to the right of center. In one embodiment, the suture head assembly 56 can be laterally articulated through an arc of about 22.5 degrees to the left of center and also to the right of center, for a total of about 45 degrees or more. In addition, the suture head assembly can be articulated up and down. In one embodiment, the suture head assembly 56 can be articulated up and down. The ability of the suture head assembly 56 to be articulated to the left and right of center, as well as up and down, permits the user to position the suture head assembly 56 for many different types of suturing applications. The articulation lever 66, just distal of the top of the handle 60, is pushed or pulled to cause the suture head assembly 56 to rotate. Viewed from above, moving the articulation lever 66 clockwise moves suture head assembly 56 to the right and moving the articulation lever 66 counterclockwise moves suture head assembly 56 to the left. The suture head assembly 56 is locked in place with the locking lever 64 located on the bottom of the device 50, below the articulation lever 66. Movement is accomplished using the solid articulation rod 68 to link the articulation lever 66 to the suture head assembly 56. The articulation rod 68 is pinned to the articulation lever 66 and to one side of the most proximal section of the suture head assembly 56 so that the articulation rod 68 pushes or pulls the suture head assembly 56 through a full range of motion (see FIGS. 20-23).

Figure 20:
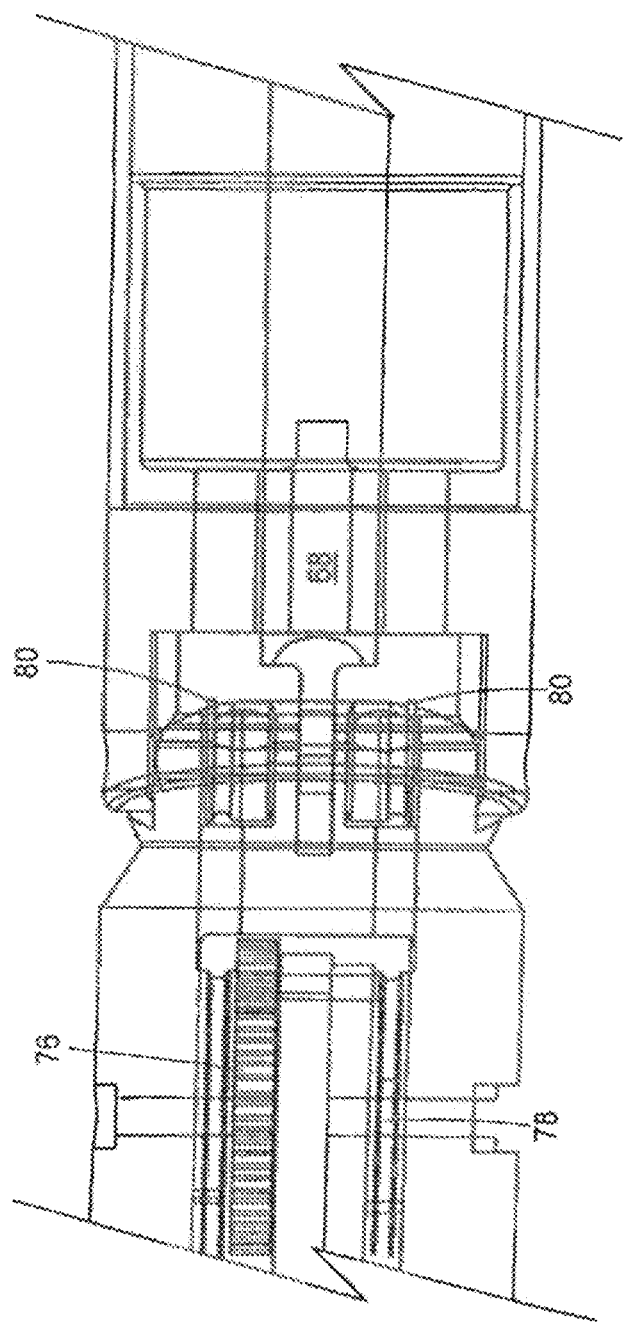
FIGS. 20-23 show different views of the suture head assembly attached to the elongated barrel via a rotation rod. The primary fixation point of the suture head assembly to the elongated barrel is depicted as being at the axis of lateral rotation.
Figure 21:
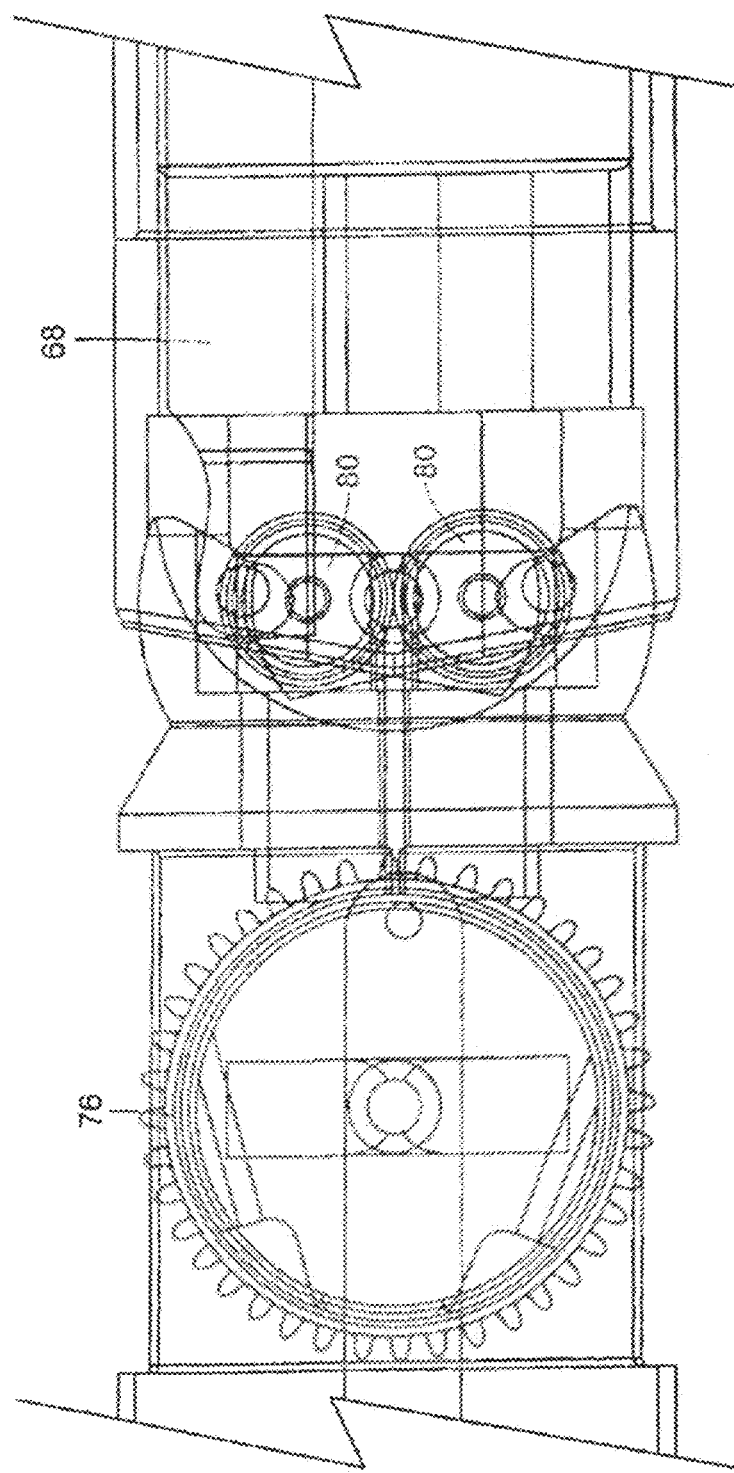
Figure 22:
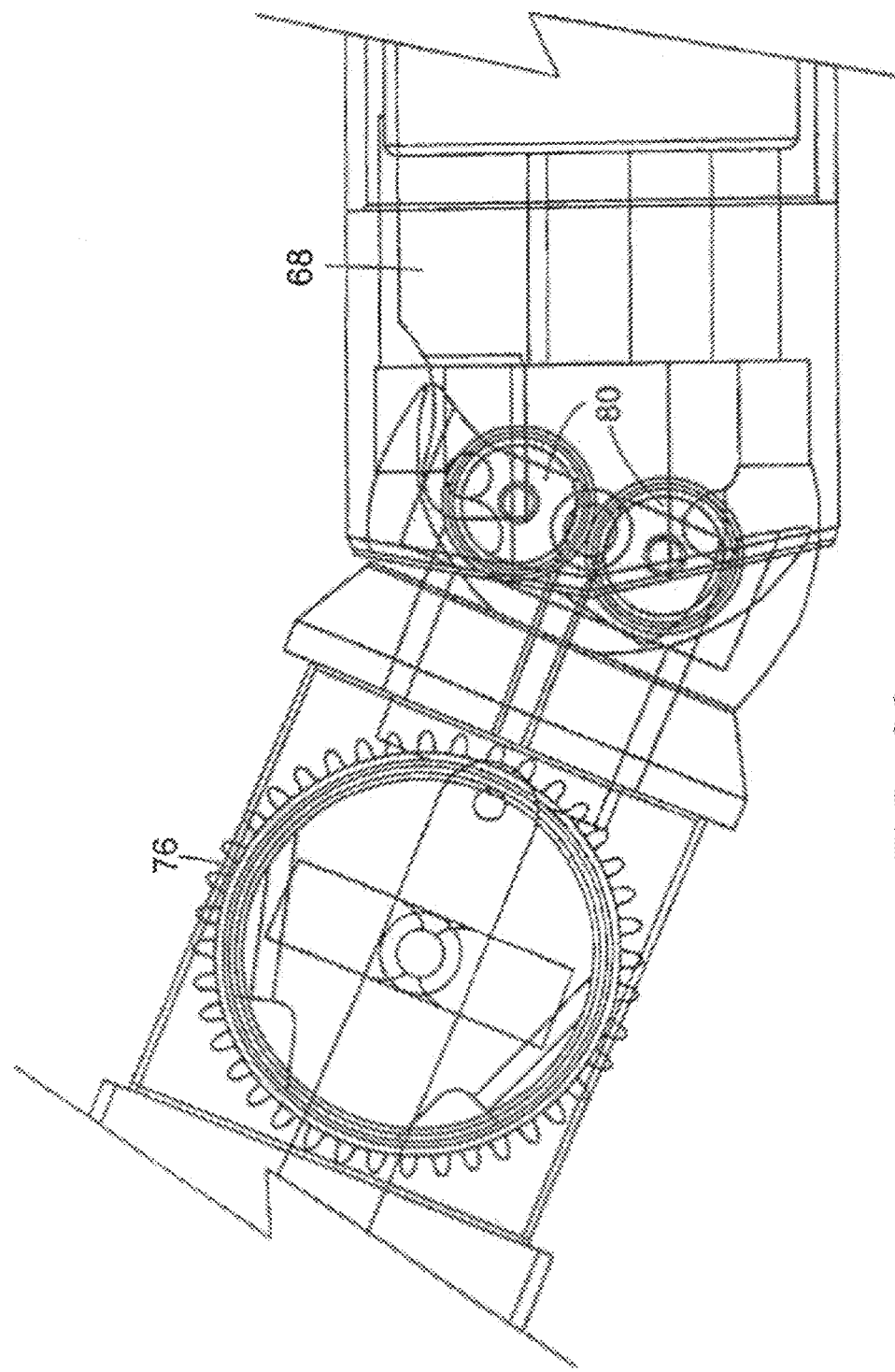
Figure 23:
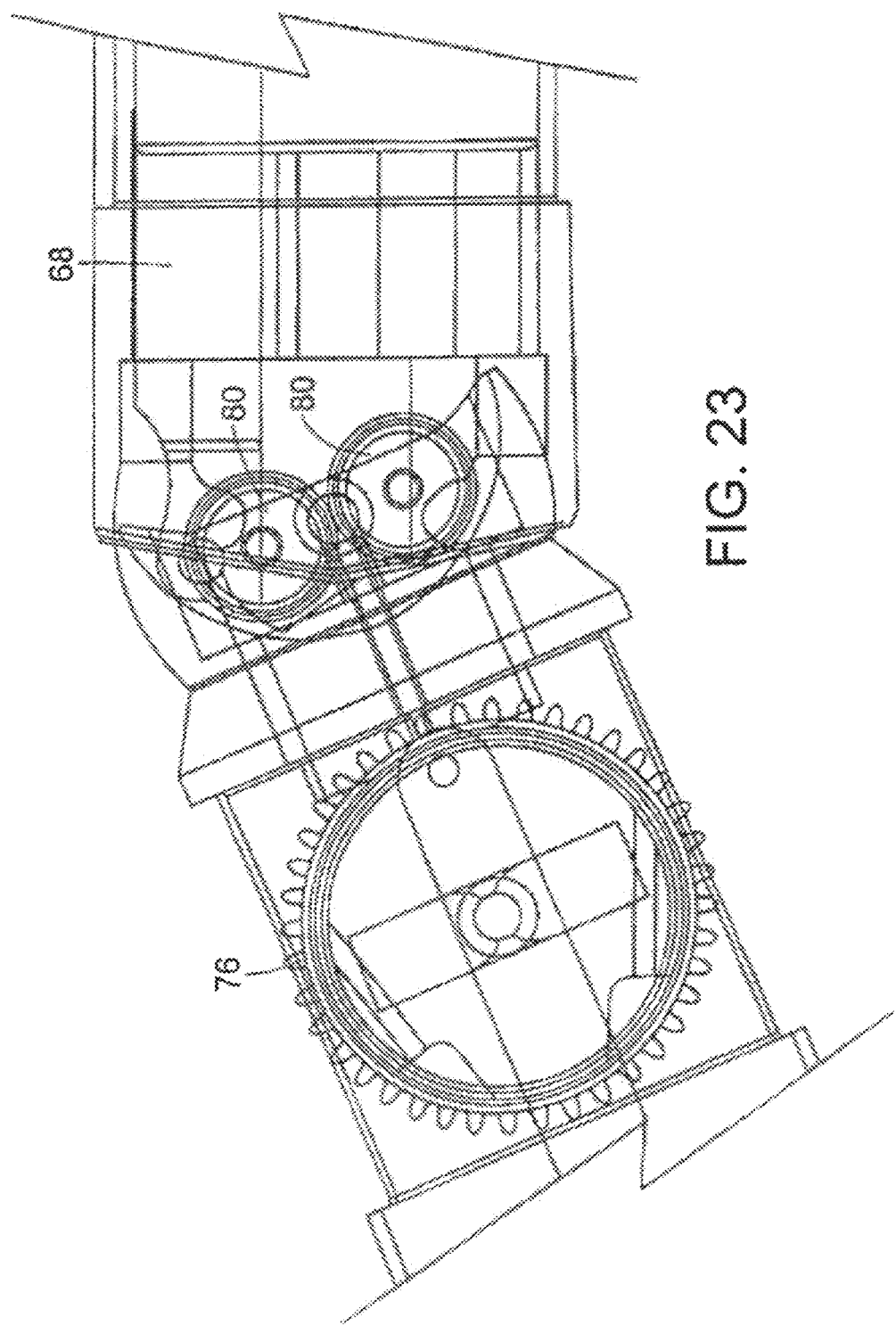

FIGS. 20-23 show the articulation rod 68 in the elongated barrel 54 and the connection to the suture head assembly 56. The suture head assembly 56 is shown moving from left articulation, to straight to right articulation (some components are not shown to allow clear viewing of the linkage). FIG. 20 shows a side view of the suture head assembly 56. FIG. 21 shows a bottom view of the suture head assembly 56 with no articulation. FIG. 22 shows a bottom view of the suture head assembly 56 articulated to the left. FIG. 23 shows a bottom view of the suture head assembly 56 articulated to the right. FIGS. 20-23 show a number of items. The articulation rod 68 runs down the center of the elongated barrel 54 and is attached to one side of the spherical portion 58. The function of the articulation rod 68 is to push and pull the suture head assembly 56 through an articulation. The two idler pulleys 80, which drive cables 84 and 86 are located in the spherical portion 58. Looking at FIG. 20, the two idler pulleys 80 seem to be one on top of the other. Instead however, they are located in plane with either pulley 76 and lower rod 140 or pulley 78 and upper rod 142.

In accordance with one embodiment, the entire suturing device 50 can be designed as a single unit which may be either reusable or disposed after a single use. If desired, the entire suturing device 50 can be designed from a number of units which, each unit may be either reusable or disposed after a single use.

The suturing device 50 is preferably configured to provide a "pistol like" grip for the user that includes an elongated barrel 54 and a handle 60 that extends from the proximal end of the elongated barrel 54. The elongated barrel 54 has either a linear or non-linear configuration, including but not limited to, straight, curved and angled configurations. A suture head assembly 56 is removably attached to the distal end of the elongated barrel 54. The suture head assembly 56 contains a portion of the drive mechanism 70 of the device 50. The working end of the suture head assembly 56 has a cartridge holder assembly 90 to which a disposable cartridge 88 that is capable of accommodating a suturing needle 120 may reside.

The disposable cartridge 88 preferably has a generally cylindrical housing with an opening or aperture 118 in the sidewall of the housing at the distal or working end thereof. An arcuate suturing needle 120 having a sharp, pointed end 124 is slidably mounted in a circular track 92 of the cartridge 88. A blunt end of the needle 126 is connected to a suturing material or thread 146. The radius of the arc defining the arcuate suturing needle 120 is approximately equal to the circumference to the cartridge housing 88 at the aperture 118 therein. The needle 120 normally resides in a "home" position in the track 92 such that the gap in the arcuate suturing needle 122 is in alignment with the aperture 118 in the cartridge 88. The sharp, pointed end of the needle 124 is situated on one side and entirely within the confines of the housing aperture 118; the pointed end of the needle 124 is, therefore, shielded by the cartridge housing 88. The blunt end of the suturing needle 126 that is attached to the suturing material or thread 146 is located at the opposite side of the aperture 118. The sharp, pointed end of the needle 124 is, therefore, wholly contained within the cartridge 88 and does not protrude beyond the housing of the cartridge 88. Thus, the sharp pointed end of the needle 124 is not exposed to the user.

In accordance with the presently disclosed embodiments, the needle 120 may be releasably engaged by a needle driver 98 that is rotatably mounted within the suture head assembly 56 so that the needle 120 can be rotated from the home position by about 360 degrees about the central vertical axis of the cartridge 88. Such a rotary action of the needle 120 causes the sharp point 124 to advance across the cartridge housing 88 so as to span the aperture 118. Thus, when the device 50 is positioned such that the incised tissue segments to be sutured are situated at the housing aperture 118, the needle 120 penetrates the tissue segments and spans the incision between them. A continued rotary movement of the needle 120 causes the needle 120 to return to the home position, and thereby causes the suturing material or thread 146 attached to the needle 120 to be pulled into and through the tissue in an inward direction on one side of the tissue incision, and upwards and out through the tissue on the opposite side of the incision. Thus, the suture material or thread 146 follows the curved path of the needle 120 to bind the tissues together with a stitch of material or thread 146 across the incision in a manner similar to manual suturing, wherein the needle 120 is "pushed" from the blunt end 126 and then "pulled" from the pointed end 124 by the pawl 98. Preferably, an anchoring mechanism is provided at the trailing terminal end of the suturing material or thread 146 to prevent the material 146 from being pulled completely through and out of the tissue segments. For example, the anchoring mechanism can be a pre-tied or a welded loop, a knot wherein the suture material or thread 146 is simply tied, or a double-stranded, looped suture is that attached to the suturing needle 120. The rotary movement of the needle 120 within the needle cartridge 88 is accomplished by a pawl 98 that may be operated by the user by holding the suturing device 50 with one hand in a pistol-like grip around the handle 60, and using at least one finger of that hand to activate.

The suturing device 50 of the presently disclosed embodiments can be used for a laparoscopic procedure, including but not limited to laparoscopic colostomy, colectomy, adrenalectomy, splenectomy, repair of paraesophageal hernia, inguinal hernia repair, ventral hernia repair, Nissen fundoplication, liver lobectomy, gastrectomy, small bowel resection, treatment of small bowel obstruction, distal pancreatectomy, nephrectomy and gastric bypass. Those skilled in the art will recognize that the presently disclosed embodiments can be used in other laparoscopic procedures.

In using the device 50 of the presently disclosed embodiments, the abdomen is insufflated with gas to create a working space for the user. Any gas known to those skilled in the art including, but not limited to, nitrogen or carbon dioxide, can be used. Access portals are established using trocars in locations to suit the particular surgical procedure. A variety of surgical instruments may then be inserted into the body through these access ports/cannulas. The user then introduces the distal end portion of suturing device 50 into a cannula, and then laterally articulates the suture head assembly 56 using the articulation lever 66 located just distal to the top of the handle 60. The suture head assembly 56 is then positioned relative to the tissue/vessel to be sutured together, and the user locks the suture head assembly 56 in place using the locking lever 64. The user then, through manipulation of suturing device 50, positions a plurality of separated tissue segments into the opening defined at the distal end portion of the suture head assembly 56 and within the aperture 118 of the cartridge 88. The user, using only one hand, may manipulate the device 50 while actuating the handle 60 to close an incision with a continuous suture whose stitches may be individually tensioned precisely and uniformly along the length of the suture similar to suturing done by hand in the conventional way. The user may employ a single suture which would extend the entire length of the incision or multiple sutures. Thus, by placement of the device 50 with the needle cartridge aperture 118 spanning the incised tissue segments and actuating the handle 60, the suturing device 50 enables the user to lay down a running stitch or interrupted stitch to close the tissue incision in a time efficient manner. Those skilled in the art will recognize that any conventional procedure for conducting laparoscopic surgery can be used with the device 50.

The needle cartridge 88 is disposably mounted on a cartridge holder assembly 90 at the distal end of the suture head assembly 56. The minimalized structural design of the suture head assembly 56 enables the user to have a clear, unobstructed view of the suturing needle 120 during advancement through the tissue segments during the course of a suturing operation, thereby enabling precise placement of the suturing device 50 to provide uniform sutures and precluding the risk of tearing tissue by placement too close to the edge of the incision. The suturing device 50 is then advanced a short distance along the incision and the aforementioned operation is repeated to produce another stitch comprising the suturing material or thread 146.

The user may continue to manipulate the suturing device 50, alternately advancing and actuating rotation of the needle 120 about an axis that is generally parallel to the direction of advancement to create a continuous suture which may extend through the entire length of the incision or a series of interrupted stitches. After each individual stitch is laid down, the stitch is tightened by exerting a pull on the suturing material or thread 146 so that the resultant suture is tensioned uniformly along the length of the incised tissue segments. Therefore, a tight closure of the segments is accomplished and bleeding and tearing of tissue are minimized. Once the appropriate amount of suture material or thread 146 has been placed, the user can use a needle grasper to tighten and knot the formed stitches.

The presently disclosed embodiments provide a method for suturing tissue during minimally invasive surgery including engaging a cartridge 88 to a suture head assembly 56 at a distal end of a suturing device 50, the cartridge 88 having a protective housing and a suturing needle 120 with a pointed end 124 and a blunt end 126; introducing the distal end of the suturing device 50 into a body cavity; positioning an opening 118 in the cartridge 88 to span a plurality of separated tissue segments; activating an actuator 52 coupled to a drive mechanism 70 that engages the suturing needle 120 to cause rotational movement of the suturing needle 120 about an axis approximately perpendicular to a longitudinal axis of the suturing device 50 and advance the suturing needle 120 through the plurality of separated tissue segments; and pulling a suturing material 146 attached to the suturing needle 120 through the plurality of separated tissue segments forming a stitch.

The presently disclosed embodiments provide a method for suturing tissue during minimally invasive surgery including (a) engaging a cartridge 88 to a suture head assembly 56 at a distal end of a suturing device 50, the cartridge 88 having a protective housing and a suturing needle 120 with a pointed end 124 and a blunt end 126; (b) introducing the distal end of the suturing device 50 into a body cavity; (c) positioning an opening 118 in the cartridge 88 to span a plurality of separated tissue segments; (d) activating an actuator 52 coupled to a drive mechanism 70 that engages the suturing needle 120 to cause rotational movement of the suturing needle 120 about an axis approximately perpendicular to a longitudinal axis of the suturing device 50 and advance the suturing needle 120 through the plurality of separated tissue segments; (e) pulling a suturing material 146 attached to the suturing needle 120 through the plurality of separated tissue segments forming a stitch and repeating steps (c) through (e) to cause a plurality of stitches to be placed through the separated tissue segments.

The presently disclosed embodiments provide a method for suturing tissue during minimally invasive surgery including inserting a distal end of a suturing device 50 having a suturing needle 120 with a pointed end 124 into a body; positioning the suturing needle 120 to span a plurality of separated tissue segments; activating an actuator 52 a first time causing the pointed end 124 of the suturing needle 120 to extend beyond a protective housing of a cartridge 88 to engage the plurality of separated tissue segments; activating the actuator 52 a second time to cause the suturing needle 120 to complete a revolution and pull a suture 146 extending from the suturing needle 120 through the plurality of separated tissue segments to form a stitch.

The suturing device 50 may be configured in different ways with respect to length and angle of the suture head assembly 56. The size of the needle 120, the needle cartridge 88, the cartridge aperture 118 and the aperture position may also be varied for use in open surgery to perform procedures such as closing of the fascia, skin closure, soft tissue attachment, anastomosis, fixation of mesh, grafts and other artificial materials.

Figure 24:
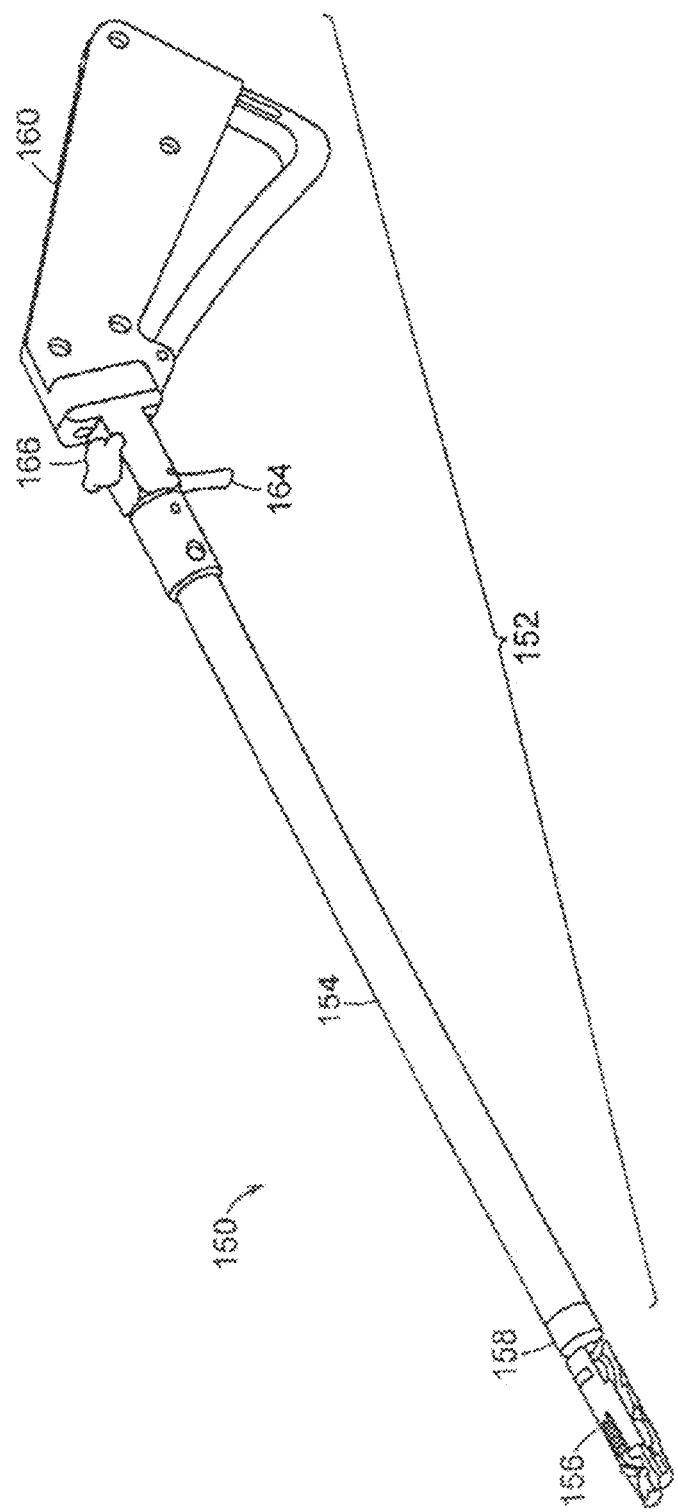
FIGS. 24 and 25 are perspective views of a suturing device.
Figure 25:
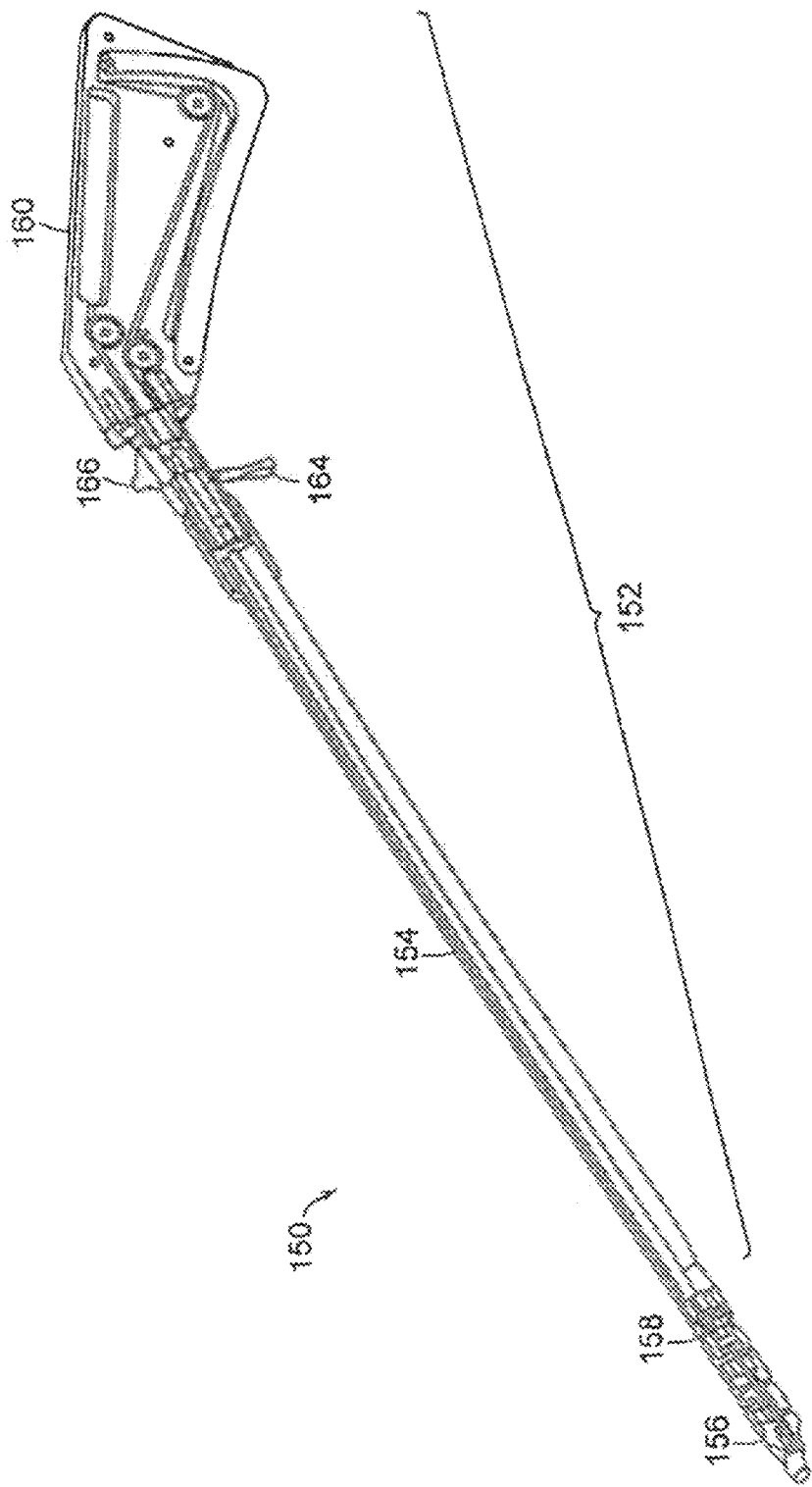

FIGS. 24 and 25 show an alternative embodiment of a suturing device shown generally at 150. Referring to FIGS. 24 and 25, the suturing device 150 can be used to produce a continuous or interrupted stitch or suture so as to enable closure of openings internal to a patient's body. The suturing device 150 can be utilized to suture any type of anatomical tissue in any type of anatomical cavity; and, accordingly, while the device 150 is described hereinafter for use with a cannula in endoscopic procedures, such as laparoscopy, the device 150 can be used in open surgery and with catheters and other small and large diameter tubular or hollow, cylindrical members providing access to small cavities, such as veins and arteries, as well as large cavities, such as the abdomen.

In an embodiment, the suturing device 150 includes an actuator mechanism shown generally at 152 which comprises an elongated barrel 154 and a handle 160 that extends from the undersides at a proximal end of the elongated barrel 154. Located within the elongated barrel 154 are mechanical parts including cables which run from the elongated barrel 154 through a spherical portion 158 and then engages with the drive mechanism in a suture head assembly 156. The spherical portion 158 resides within the distal portion of the elongated barrel 154 and rotates with low friction. In an embodiment, a drive mechanism 170 includes a pulley system and cables that extend from the distal end of the suture head assembly 156 to the proximal end of the elongated barrel 154.

The suture head assembly 156 houses the mechanism for driving a curved needle 220 in a complete 360 degree circular arc. The orientation of the suture head assembly 156 is such that when the needle 220 is attached to the suture head assembly 156 the needle 220 is driven in a curved path about an axis approximately perpendicular to the longitudinal axis of the device 150. In this way, the needle 220 may be optimally visualized as the needle 220 is driven in a circular arc. Also, as shown in FIGS. 24 and 25, the needle 220 is in a plane parallel to the drive mechanism and fits into the same space in the suture head assembly 156.

The improved visibility offered by the shape and configuration of the suture head assembly 156 enables precise device placement over the incision, and uniform advancement of the suturing device 150 after every stitch to provide a uniform and symmetric suture, thereby minimizing the risk of tearing tissue and bleeding due to a stitch being positioned too close to the edge of the incised tissue. In one embodiment, the entire device 150 or parts of the device 150, such as the suture head assembly 156, the elongated barrel 154, the handle 160, and the needle 220, are composed of a sterilizable medical grade plastic material, in which case, the entire device 150 or parts of the device 150 may discarded and disposed after a single use. In an embodiment, the device 150 is composed of a sterilizable medical grade metallic material such as stainless steel to enable reuse subsequent to sterilization following a prior use. In another embodiment, the device 150 is composed of a sterilizable medical grade metallic material such as titanium to enable reuse subsequent to sterilization following a prior use. The use of titanium is beneficial for certain procedures including Magnetic Resonance Imaging (MRI) and Computed Tomography (CT) because they are X-Ray radiolucent and do not interfere with MRI and CT scans.

FIG. 24 shows the handle 160 in an open position. FIG. 25 shows the handle 160 in the closed position. The suture head assembly 156 is attached to the distal end of the elongated barrel 154. In one embodiment, the suture head assembly 156 is removably attached to the distal end of the elongated barrel 154. The length of the suture head assembly 156 can range from about 10 mm to about 100 mm. In a particular embodiment, the length of the suture head assembly 156 is about 40 mm. The length of the elongated barrel 154 can range from about 50 mm to about 400 mm. Those skilled in the art will recognize that the elongated barrel 154 can be made shorter or longer depending on the intended use of the device 150. In one embodiment, the elongated barrel 154 is about 300 mm in length. In another embodiment, the elongated barrel 154 is about 350 mm in length. An articulation lever 166, just distal to the top of the handle 160 is pushed or pulled to cause the suture head assembly 156 to rotate. Moving the articulation lever 166 clockwise moves the suture head assembly 156 to the right and moving the articulation lever 166 counterclockwise moves the suture head assembly 156 to the left. The articulation lever 166 can also be moved to articulate the suture head assembly 156 up and down, as desired. The suture head assembly 156 is locked in place with a locking lever 164 located on an underside of the device 150, below the articulation lever 166. The suture head assembly 156 may be articulated, and the elongated barrel 154 may be any length appropriate for the intended clinical application of the device 150. The diameter of the device 150 can range from about 3 mm to about 20 mm. In one embodiment, the diameter of the device 150 is about 12 mm. In another embodiment, the diameter of the device 150 is about 3 mm.

The handle 160 may be a grip that is squeezed in order to actuate the suturing device 150. The suturing device 150 is actuated by the actuator mechanism 152 coupled to a drive mechanism 170. The actuator mechanism 152 of the suturing device 150 may comprise a triggering mechanism that is known in the art, such as for example, the triggering mechanisms disclosed in U.S. Pat. No. 6,053,908 and U.S. Pat. No. 5,344,061, both of which are hereby incorporated by reference. Alternatively, the actuator mechanism 152 can be either a manually operable button or switch, or mechanically operable by an automated electrical or a fuel driven device, such as for example, an electrical, electromagnetic or pneumatic motor powered by electrical, electromagnetic, compressed air, compressed gas, hydraulic, vacuum or hydrocarbon fuels. Those skilled in the art will recognize that any actuator mechanism of any type known in the art can be within the spirit and scope of the presently disclosed embodiments.

Figure 26:
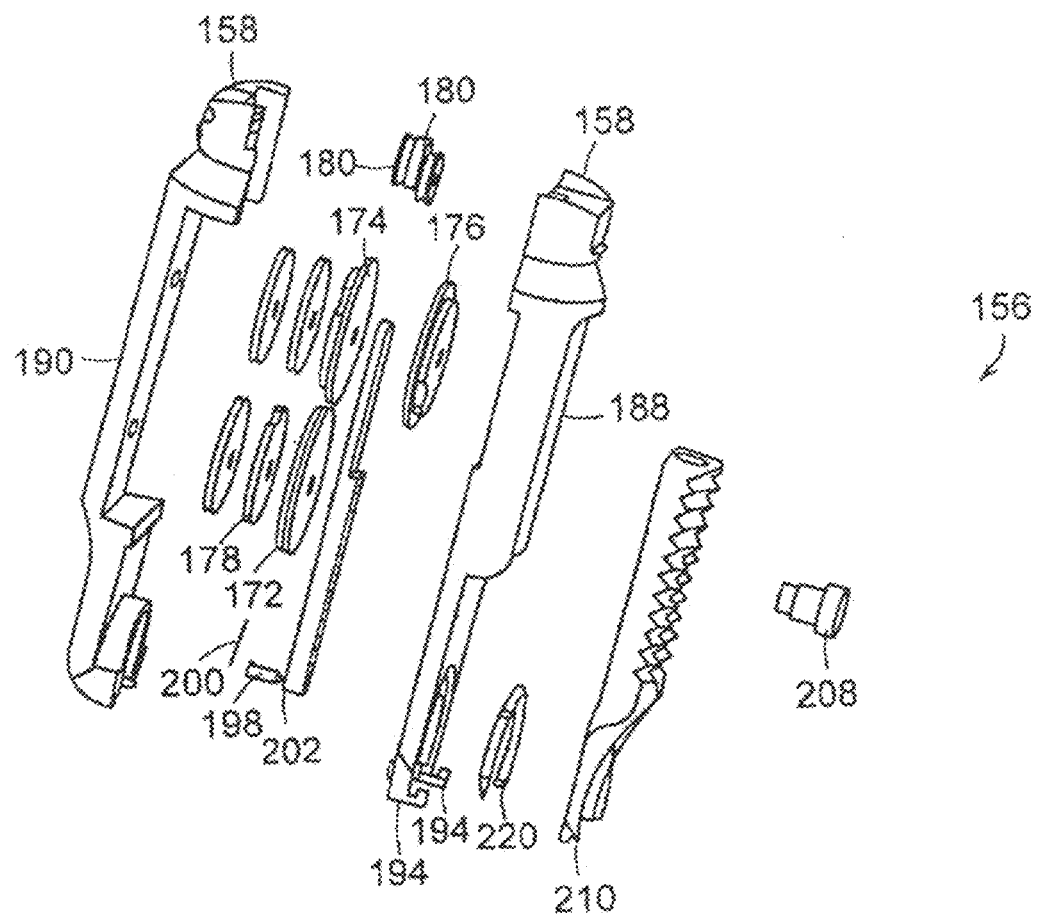
FIG. 26 is a segmented assembly view of the suture head assembly of FIGS. 24 and 25.

FIG. 26 provides an assembly view of the suture head assembly 156. The suture head assembly 156 is fabricated from multiple pieces including a holder assembly 190, a needle holder assembly 188, a latch 210, and parts of the drive mechanism 170 including a plurality of pulleys, 172, 174 and 176 and two idler pulleys 180 involved in driving a needle driver 198 through a semicircular path. Pulleys 172 and 174 may include a set of four pulleys, or two sets of pulleys, labeled 178. In one embodiment, the needle driver is a pawl 198. A shoulder screw 208 and a plurality of needle assembly extensions 194 may be used to keep the latch 210 locked in place over the needle holder assembly 188 and the suturing needle 220. The needle holder assembly 188 includes a curved track 192 where the needle 220 rides. Pulleys 172, 174 and 176 are engaged with an actuator arm 202, which is attached to the pawl 198. The pawl 198 interfits with two notches 232 located on the face of the needle 220 at about 180 degrees apart which drives the curved needle 220 in a circular arc. The suture head assembly 156 is configured so that the pawl 198 or other needle driver known in the art, does not intrude into or obstruct the area within the curve of the needle 220. The area within the circular arc of the needle 220 is unobstructed; there is not a hub at the center of the circular arc so that the device 150 can encompass the maximum volume of tissue within the circular arc of the curved needle 220. In this way, the needle 220 may be rotated through a relatively large arc, allowing the needle 220 to obtain a sufficient "bite" into the tissue. Preferably, the needle 220 will have a radius of curvature of about 3 mm to about 40 mm. In one embodiment, the device 150 sutures within the limit of the diameter of the suture head assembly 156, which is advantageous to suturing through small cannulas during minimally invasive surgery. In one embodiment, the diameter of the curved needle 220 does not exceed the diameter of the suture head assembly 156.

FIGS. 27A and 27B show detailed views of the drive mechanism 170 located in the suture head assembly 156 with respect to driving the needle 220 during use of the device 150 (the needle holder assembly 188 and the holder assembly 190 have been removed to show the drive mechanism 170 in detail). The drive mechanism 170 includes the actuator arm 202 that engages pulleys 172, 174, and 176 and the pawl 198 that drives the needle 220 through a curved path. The pawl 198 is located in the distal end of the actuator arm 202 and is capable of engaging the notches 232 located along the face of the needle 220. A flat spring 200 keeps the pawl 198 engaged into the notches 232 of the needle 220. When the needle 220 is pushed around, the pawl 198 will be pushed back up against the flat spring 200 and allow the needle 220 to cycle. As the handle 160 is closed and opened, the pawl 198 moves through the same arc as the pulleys. The actuator arm 202 is activated by the user upon squeezing of the handle 160, and is capable of sweeping back and forth in an arc spanning about 190 degrees or more.

Figure 28:
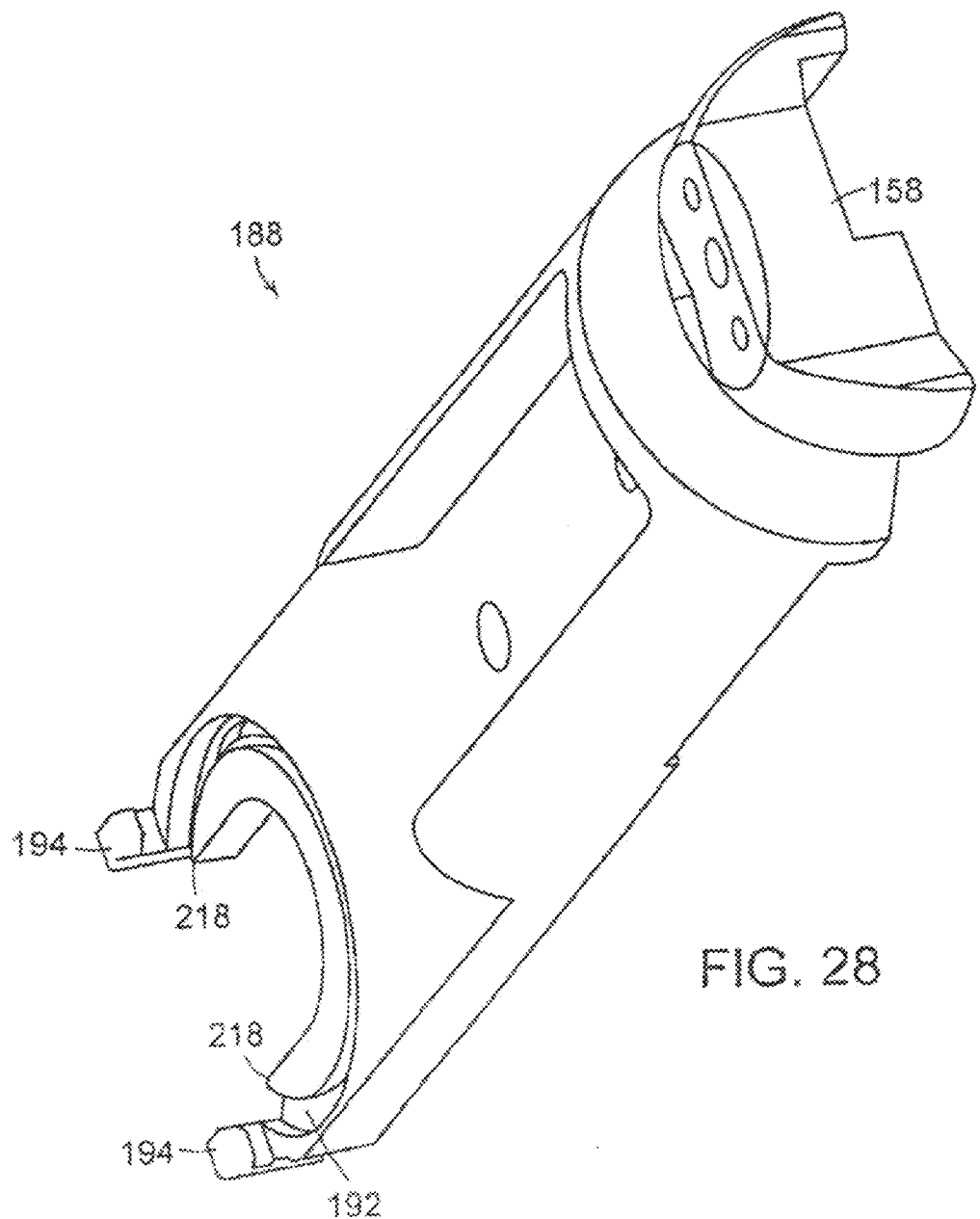
FIG. 28 is a close-up view of the needle holder assembly for the suture head assembly of FIGS. 24 and 25.

FIG. 28 shows a close-up view of the needle holder assembly 188 showing the curved track 192 where the needle 220 resides as well as the needle holder assembly extensions 194 that help keep the latch 210 in place. The suturing needle 220 follows a curved path along the track 192 during rotation of the suturing needle 220. The curved track 192 for the needle 220 may be machined into the needle assembly 188 and provides a captive curved track 192 so that the needle 220 can be driven around with precision. The curved track 192 includes an inside slot and a larger slot surrounding the inside slot. The larger outside slot provides clearance for the pawl 198, so that the pawl 198 can maneuver around without hitting anything, and the smaller inside slot provides clearance for a pawl tip 199, which goes through the smaller inside slot and then into the needle 220 so that the pawl tip 199 can drive the needle 220.

Figure 29:
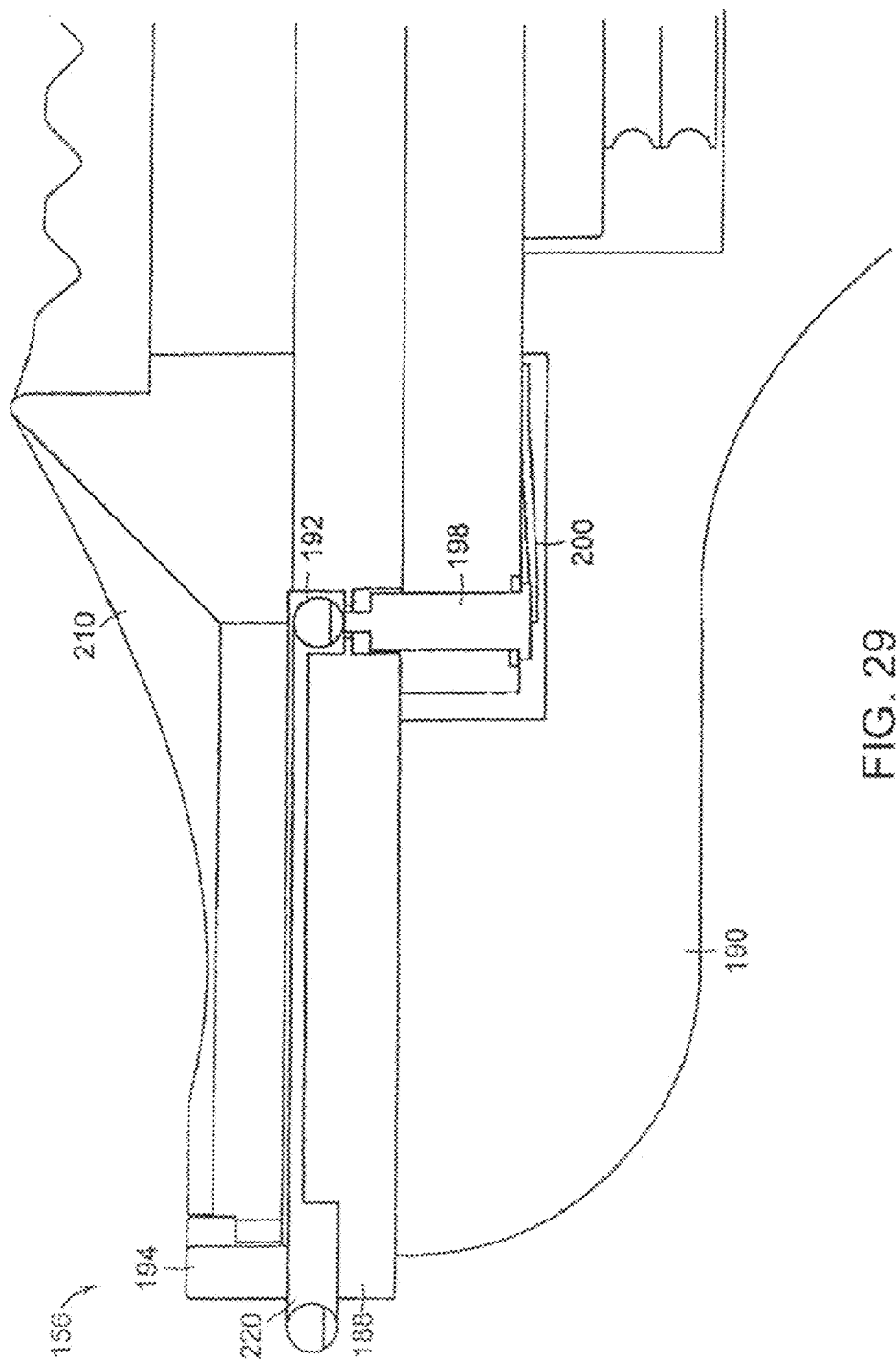
FIG. 29 is a close-up view of the distal end of the suture head assembly of FIGS. 24 and 25.

FIG. 29 shows a close-up view of the suture head assembly 156 with the needle holder assembly 188, the holder assembly 190, the latch 210 and the needle 220 in view as well as the relationship between the pawl 198 and the actuator arm 202 with respect to the needle 220. The needle 220 is enclosed within the needle holder assembly 188, so the sharp pointed end 224 of the needle 220 is not exposed. This needle 220 position, as loaded, is referred to as the "home" position. In the home position, the needle 220 is fully contained within the needle holder assembly 188 to eliminate needle-pricks during handling of the suture head assembly 156. The needle assembly extensions 194 form a "tongue-in-groove" connection with the latch 210, which keeps the forces from the needle 220 from opening the thin members of the latch 210. The needle assembly extensions 194 cause an entrapment at a distal end of the suturing device, thus locking the latch 210 in place. Squeezing the device handle 160 fully operates the device 150 through one full cycle. The first full actuation of the handle 160 drives the needle 220 through about a 190-degree arc. The pointed end 224 of the needle 220 exits the protective enclosure of the needle holder assembly 188, drives through the tissue to be sutured, and re-enters the protection of the needle holder assembly 188 of the device 150. This position, after the first squeeze of the handle 160, is referred to as the "rotation" position. The handle 160 is then released, and the needle 220 remains in the rotation position while the pawl 198 and the actuator arm 220 return to their start position. The handle 160 is then squeezed again driving the needle 220 through about a 190-degree arc returning the needle 220 to the home position. A flat pawl spring 200 keeps the pawl 198 engaged into the pawl notches 232 on the needle 220. When the needle 220 is pushed around the pawl 198 will be pushed back up against the flat pawl spring 200 and allow the needle 220 to cycle.

Figure 30:
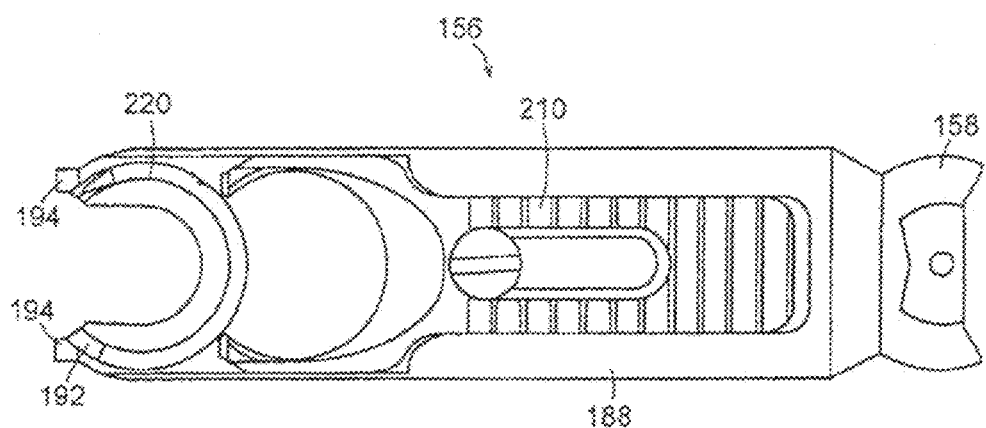
FIGS. 30 and 31 show the suture head assembly of FIGS. 24 and 25.
Figure 31:
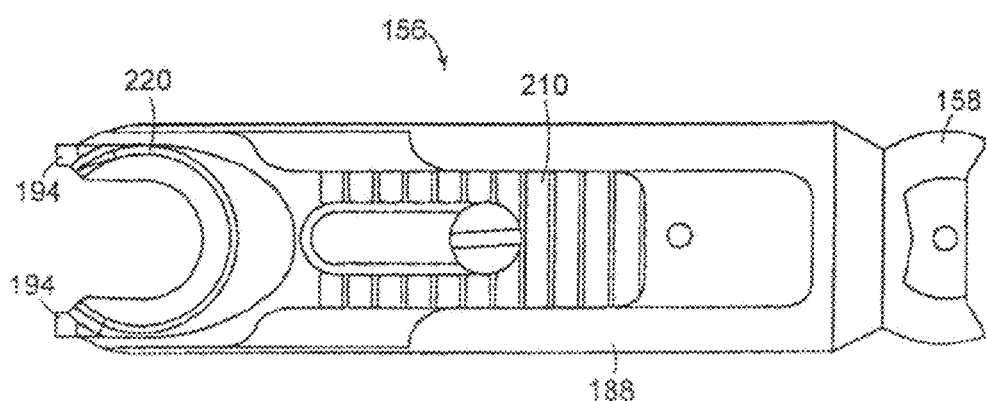

FIGS. 30 and 31 show top views of the suture head assembly 156. Needle holder assembly 188 forms a connection with the latch 210. The latch 210 forms a top cover over the suturing needle 220 which is in the curved track 192 of the needle holder assembly 188. FIG. 30 shows the latch 210 in the open position, which is for needle 220 removal and insertion into the needle holder assembly 188. To insert and/or remove the needle 220 a user may turn the needle 220 180 degrees in its curved track 192 from the as-drawn position. A user may grab the needle 220 by hand or with a surgical tool to either install the needle 220 or remove the needle 220. By grabbing and lifting the needle 220 out, the needle 220 is removed. By grabbing the needle 220 the needle can be inserted when the latch 210 in the open position. FIG. 31 shows the latch 210 in the locked position, also known as the forward position.

Figure 32:
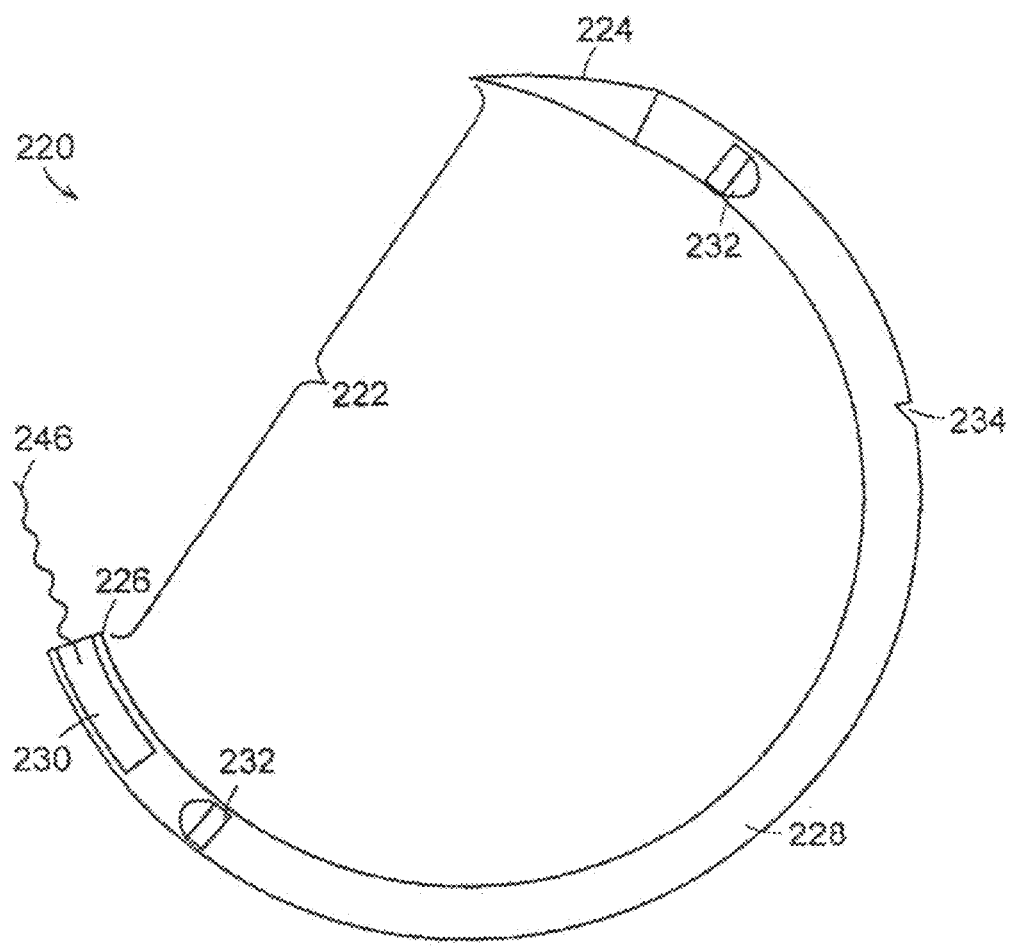
FIG. 32 is a view of a curved suturing needle with notches on the face of the suturing needle to be used with the suturing device of FIGS. 24 and 25.

FIG. 32 shows the suturing needle 220. The two notches 232 are located about 180 degrees apart on the face of the needle 220 and assist in driving the needle 220. The pawl 198 engages the notches 232 when driving the needle 220 through the circular motion. A third notch 234 is located on the outer surface of the needle 220. The notch 234 provides an anti-rotation feature by preventing rotation of the needle 220. The needle 220 is formed as a circular split ring with a gap 222, a sharp, pointed end 224, and a blunt end 226. The needle 220 further comprises an opening 230 to accommodate the leading end of the suturing material or thread 246. In an embodiment, the opening 230 is the form of an eye though which the leading end of the suturing material or thread 246 may be passed through for attachment to the needle 220. In the illustrated needle 220, the needle 220 comprises an opening 230 in the form of a cylindrical bore aligned axially with respect to the needle 220, located at the blunt end 226. The opening 230, can be positioned anywhere along the arc or the needle 220 between the apex 228 and the blunt end 226. The leading end of the suturing material or thread 246 is inserted into the opening 230 and restrained by mechanically crimping or other connection methods known in the art. To enable the needle 220 to penetrate tissue to a required depth, the arc length of the needle 220 is preferably about 240 degrees to about 300 degrees. The needle 220 comprises two symmetric notches 232 along the face ("drive notches"). The notches 232 are located directly opposite to each other. A similar notch 234 is located on the radially outer edge ("outer notch") of the needle 220 proximally to the inner notch 232 closer to the sharp, pointed end 224. The outer notch 234 engages with an anti-rotate spring, whereby rotation of the needle 220 in a direction opposite to the advancing direction or "needle backing-up" is prevented. The positive engagement of the needle outer notch 234 during operation of the suturing device precludes the needle 220 from straying out of sequence during the suturing process.

Figure 33:
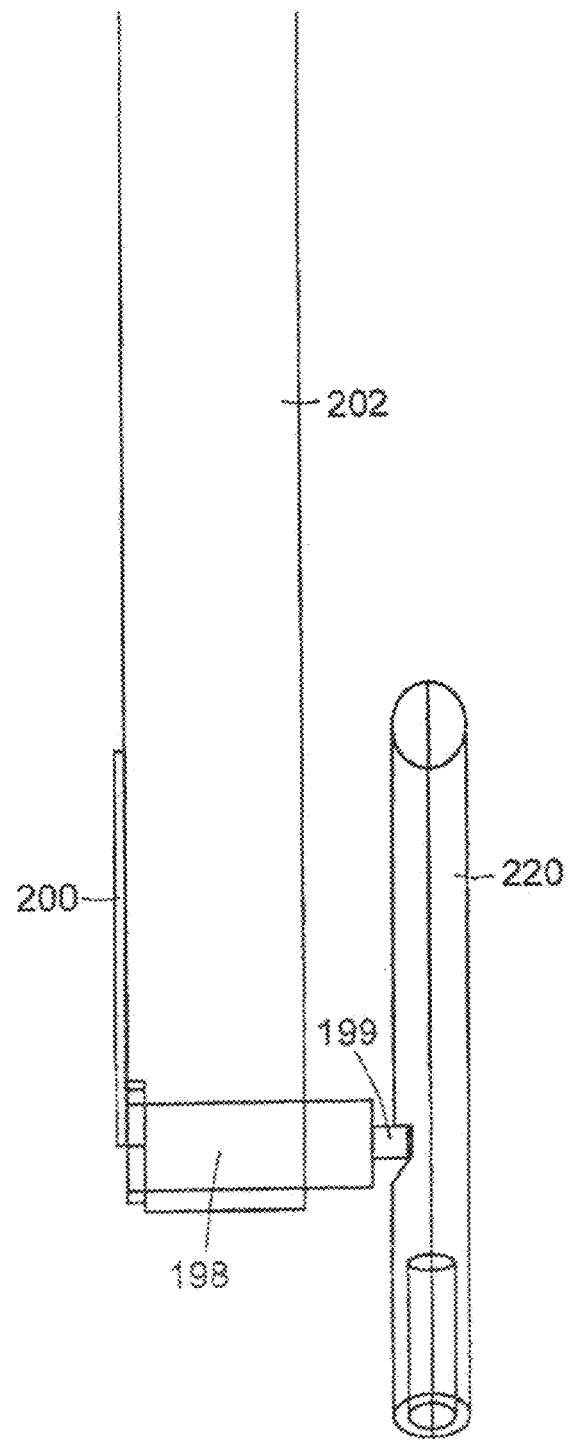
FIG. 33 shows a view of the pawl in contact with the suturing needle for the suturing device of FIGS. 24 and 25.

FIG. 33 shows a close-up view of the pawl tip 199 engaging the drive notches 232 of the needle 220. The drive notches 232 are engaged by the pawl tip 199 of the drive mechanism 170 and enable the needle 220 to undergo a rotary movement upon actuation of the drive mechanism 170, thereby causing the needle 220 to penetrate into and advance through tissue.

Figure 34:
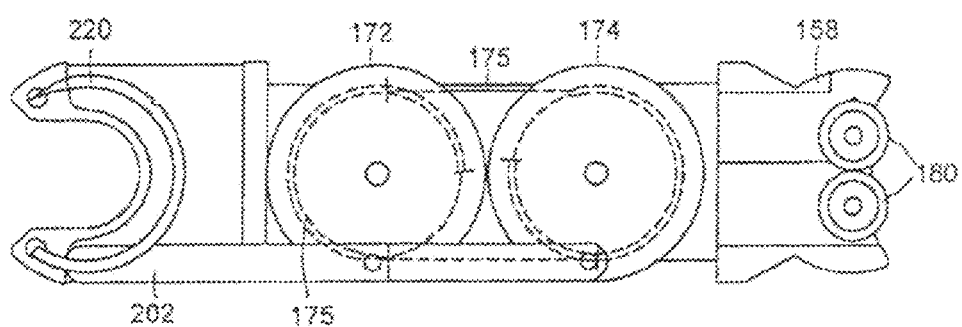
FIGS. 34 and 35 show a close-up view of the suture head assembly of FIGS. 24 and 25 and the associated pulleys that move the drive mechanism.
Figure 35:
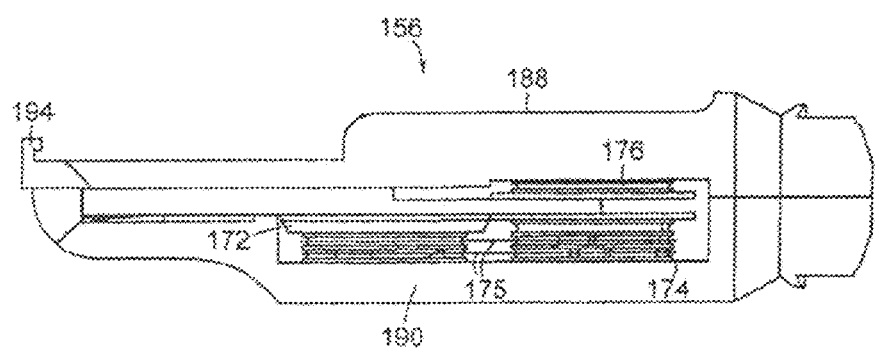

FIGS. 34 and 35 show parts of the drive mechanism 170 including return pulleys 172 and 174. Pulleys 172 and 174 are connected to each other using wires 175. As can be seen in FIG. 27A and FIG. 27B, pulleys 172 and 174 are made up of four pulleys 178 that are connected together by laser welding or other methods known in the art. The four pulleys 178 produce an over-rotation, of about 190 degrees. The over-rotation leads to the wire 175 design where there is a wire 175 on each set of pulleys 178. As shown in FIG. 34 and FIG. 35, there are two wires 175 with four pulleys 178, resulting in the four pulleys 178 being in synch with one another, even under load. The four pulleys 178 are rotationally in sync, i.e., one pulley 178 will follow the other pulley 178, because the wires 175 are configured to be pulling against one another. The wire 175 may be attached to the pulleys 178 via a hole that the wires 175 are soldered into. FIG. 35 shows a side view of the suture head assembly 156 which shows the two wires 175 connecting the four pulleys 178 together for synchronized rotation.

Figure 36:
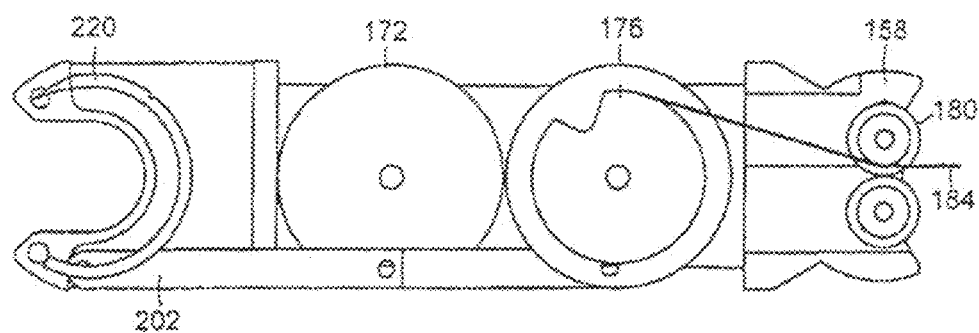
FIGS. 36 and 37 are top views of the suture head assembly and cables that connect the drive mechanism located in the suture head assembly and the elongated barrel when the handle is in the open position for the suture device of FIGS. 24 and 25.
Figure 37:
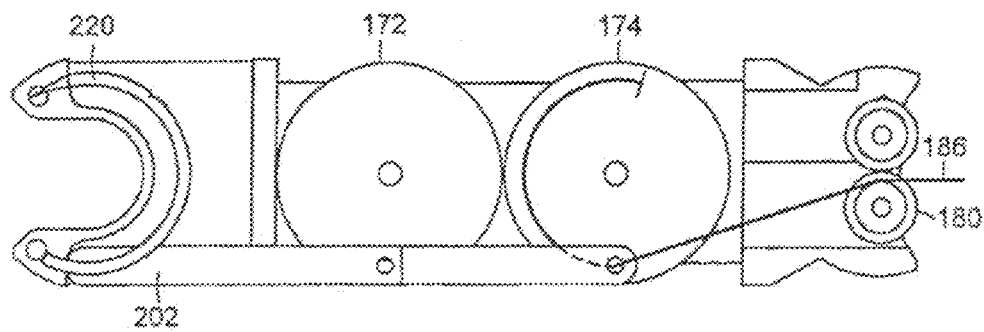
Figure 38:
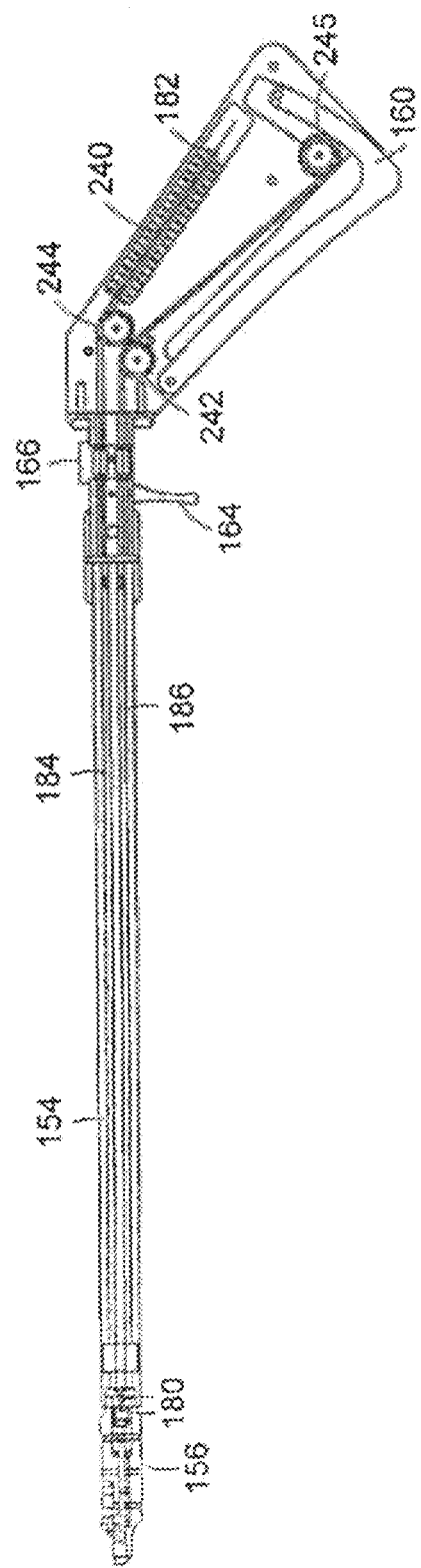
FIG. 38 shows a side elevational view of the suturing device of FIGS. 24 and 25 showing parts of the drive mechanism.

FIGS. 36 and 37 in conjunction with FIG. 38, show the connections and positions of cables 184 and 186 to the drive pulley 176 and to the return pulleys 172 and 174, respectively, and to the when the handle 160 is in the open position. The cables 184 and 186 may be made from stainless steel. Connected at the proximal end of the suture head assembly 156 there is the spherical portion 158 that contains part of the drive mechanism 170 including two idler pulleys 180 and cables 184 and 186. FIG. 36 shows a top view of the suture head assembly 156 with the cable 184 running through two idler pulleys 180 and wrapped around drive pulley 176. FIG. 37 shows a top view of the suture head assembly 156 with the cable 186 running through two idler pulleys 180 and wrapped around return pulley 174. The cable 186 runs from return pulley 174 through the elongated barrel 154 and to the very proximal end of the handle 160. The force to move the needle 220 from the home position (shown in FIGS. 36 and 37) to a rotation position comes from a return spring 240 that is connected to the cable 184, resulting in a pre-load (shown in FIG. 38). When the trigger of the handle 160 is squeezed closed, the handle 160 moves to the closed position and the drive pulley 176 turns counterclockwise, driving the needle 220. At the same time, the cable 186 drives the return pulley 174 counterclockwise and cycles the actuator arm 202 to drive the needle 220 forward through the tissue. The needle 220 is driven through a circular motion, through a cycle, and the cable 184 is compressing the return spring 240 on the other end. When the handle 160 closes more, the actuator arm 202 drives the needle. When the trigger of the handle 160 is released, the front pulley 178, which is now fully charged with the return spring 240, will return the needle 220 to the home position. The return spring 240 pulls cable 184, returning the pulleys to their starting positions, and returning the actuator arm 202 to a position to engage the second drive notch of needle 220. A second compression-release cycle returns the needle 220 to the home position. Relaxing the trigger of handle 160 takes no power.

FIG. 38 shows a side elevational view of the suturing device 150. The handle 160 includes a number of internal parts—a cable connector 182 has a hole and a shoulder. The shoulder rides against the end of the return spring 240, and the hole provides an opening for the cable 184. The return spring 240 is compressed and the cable 184 is soldered or locked to the connector 182, so that the cable 184 provides a preload onto the return spring 240. The cable 184 runs from the connector 182 through the return spring 240 over pulley 244, through the elongated barrel 154, through the spherical portion 158, between the idler pulleys 180 and fixed to the drive pulley 176. The cable 186 is connected at the very proximal end of the handle 160 and lies under pulley 245, over pulley 242, through the elongated barrel 154, through the spherical portion 158, between the idler pulleys 180 and fixed to the return pulley 174.

When the handle 160 is translated from the open position to the closed position the needle 220 is driven through the tissue. A user has a tactile feel as the needle 220 moves. If the needle 220 runs across something that is impenetrable, the handle 160 will stop moving and the user could feel this in their hand holding the handle. When the handle 160 is in a closed position, the return spring 240 takes on a charge, the return spring 240 has shortened in length. When the handle 160 is released, the return spring 240 pulls the cable 184 and brings the needle 220 back to the home position and also brings the handle 160 back to the open position. The return spring 240 provides a load on the cable 184. A loop is formed throughout the suturing device 150 that includes the cables 184 and 186 and the pulleys 172, 174 and 176 such that cable 184 is attached at one end to the return spring 240, at the other end to the drive pulley 176. The cable 186 is attached to the return pulley 174 and then cable 186 attaches to the very proximal end of the handle 160, thus forming a loop. The return spring 240 can be set to a desired spring-rate so that the return spring 240 performs as desired by the user. The return spring 240 should have a small amount of preload to make sure that the handle 160 opens all the way, which provides that the driving mechanism 170 would return the needle 220 to the home position.

The cables 184 and 186 extend through the elongated barrel 154 and connect to the drive mechanism 170 in the suture head assembly 156. The long length of the cables 184 and 186 provides a small amount of a spring buffer. If the suturing device 150 were to become bound or something locked up at the suture head assembly 156 this would not translate. If the user continued to pull on the handle 160 to close the handle 160, the cables 184 and 186 would stretch and should not break. The two idler pulleys 180, which drive the cables 184 and 186 are located in the spherical portion 158. As shown in FIG. 34, the two idler pulleys 180 appear to be one on top of the other, but they are located in a plane with either pulleys 174 and 176 or pulley 178 (see FIG. 26).

FIG. 39 shows an alternative embodiment of a suture head assembly 356. The actuator arm 102 (FIGS. 3A, 4A and 4B) of the suture head assembly 56 is replaced by a tendon or band filament 302 (FIG. 39). The cables 84 and 86, and drive rods 140 and 142 (FIG. 8) can be replaced by an actuator that can move fore and aft with compression and release of the handle 60 (FIG. 8) or 160 (FIG. 24). The actuator can be a drive rod (not shown), and can be constructed of a tensile material that permits lateral elastic flexibility but minimal longitudinal compressibility, such as steel or other metal alloys with spring-like qualities, shape memory alloys, such as NITINOL® or a flexible hardened polymer or plastic such as high density polyethylene or polypropylene. The drive rod can be encased within a passageway inside the elongated barrel 54, the walls of which can include a sufficiently lubricious material to minimize the friction of the fore and aft movement of the drive rod. For example, the passageway may be made from or include a coating of a fluoropolymer or other lubricious material, such as silicone oil and the like. The drive rod can be connected on its distal end to the tendon or filament 302 by any suitable means (including, for example, the use of a screw, a bolt, adhesive, a weld joint, a hinge joint, or a snap-lock connection).

The suture head assembly 356 can be attached rigidly to the elongated barrel 54. Alternatively, the suture head assembly 356 can be attached moveably to the elongated barrel 54 by an articulating joint as shown in FIG. 2A and FIGS. 20-23. For example, the proximal end of the suture head assembly 356 (FIG. 39) can be modified to form a partially spherical portion similar to spherical portion 58 (FIG. 2A), which can permit superior-inferior motion of the suture head assembly 356 with respect to the elongated barrel 54. An articulation rod 68 can be used as shown in FIGS. 20-23 to push and pull the suture head assembly 356 through an arc within the limits of the articulation. Those skilled in the art will recognize there are many possible means of connecting an embodiment exemplified by the suture head assembly 356 to a handle and actuating mechanism to achieve the push-pull motion of the tendon or filament 302.

Figure 39A:
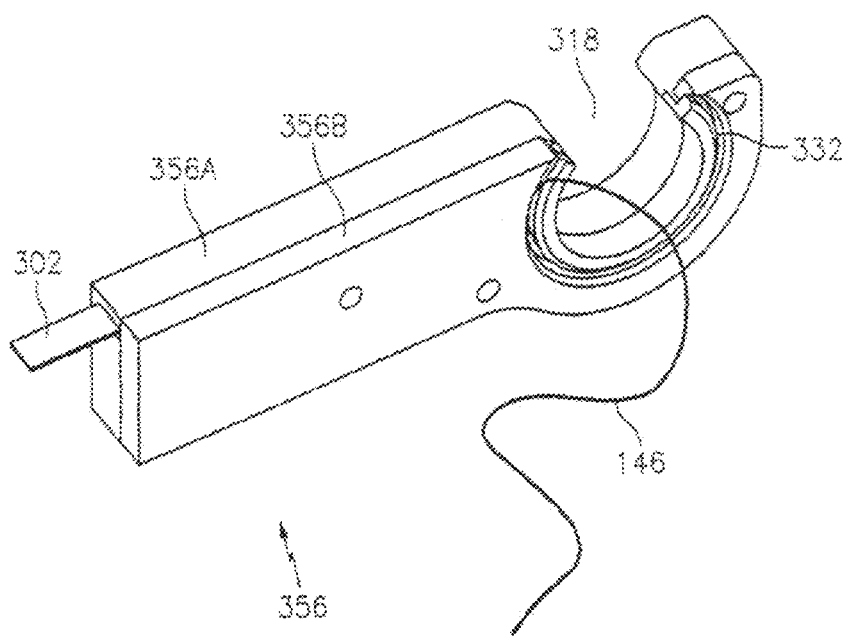
FIG. 39A shows a top perspective view of a second embodiment of the suture head assembly made in accordance with the teachings of the invention, in which a resilient elongated member moves proximally and distally to actuate movement of the suturing needle about a circular path.

As shown in FIG. 39A, in this embodiment the suture head assembly 356 is comprised of two mating components 356A and 356B. A needle track 332 is located in the needle track component 356B. A drive track (not shown) is located in the drive track component 356A next to the needle track 332. In this embodiment, the suturing needle 220 exits the suture head assembly 356 from the distal end of aperture 318, and re-enters the device at the proximal end of aperture 318. Therefore, in its 'home' position, the blunt end 226 of needle 220, and its attached suture material 246 are situated more proximally in the suture head assembly 356 than the pointed end 224 (not shown).

Figure 39B:
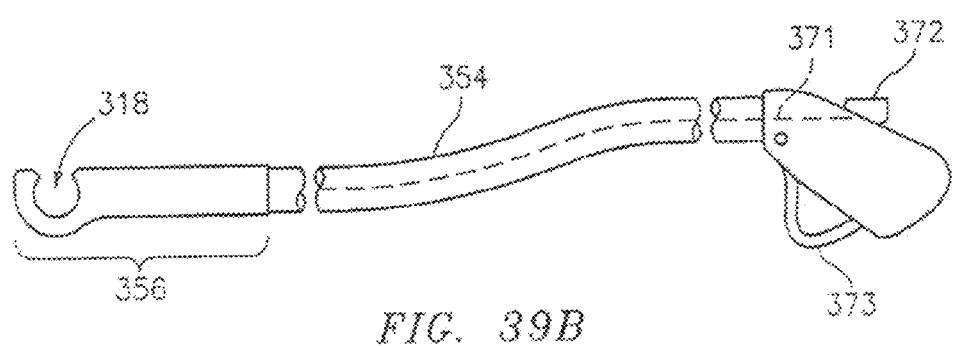
FIG. 39B depicts the suturing head of FIG. 39A incorporated into a suturing device having a flexible steerable proximal segment.

By way of further example, as depicted in FIG. 39B, device 300 equipped with a suture head assembly 356 may be provided with a flexible proximal segment 354 and include a steering mechanism for controlling curvature of the shaft. The steering mechanism may achieve steering in any suitable manner, such as steering wires. For example, two, four or any other suitable number of steering wires 371 may be used to control movement of device 300. Steering may be controlled accordingly by way of a steering control mechanism 372, which may be made in any way known in the art. Similar to the embodiments of FIGS. 1-38, an actuator 373 is also provided for activating the suturing head. As will be appreciated by those of skill in the art, the embodiments of FIGS. 1-38 may similarly be modified to include a flexible barrel (54, 154), as desired.

As embodied herein, the tendon 302 may include an elongated flexible member that can slide fore and aft within a track in the suture head assembly 356. It can have any cross-sectional shape, including for example, round, oval, square, or rectangular. In a preferred embodiment, it is relatively flat, forming a band, which has the advantage of limiting the flexibility of the tendon 302 to one lateral dimension (e.g., superior-inferior and not side-to-side). It is preferably constructed of material that is minimally compressible, allowing for the longitudinal transmission of a pushing as well as a pulling force. In one embodiment, the material from which a tendon is constructed has sufficient tensile properties to exert a spring-like force that opposes lateral flexion. Examples of material with such properties can include, for example, shape memory alloys such as NITINOL®, steel or other metal alloys with spring-like qualities, or a flexible hardened polymer or plastic such as high density polyethylene or polypropylene. In other embodiments, spring-like properties on lateral flexion are not required, where, for example, the lateral movement of the tendon is urged by a spring located with the suture head assembly 356 that exerts a force against the external surface of the tendon.

Figure 40:
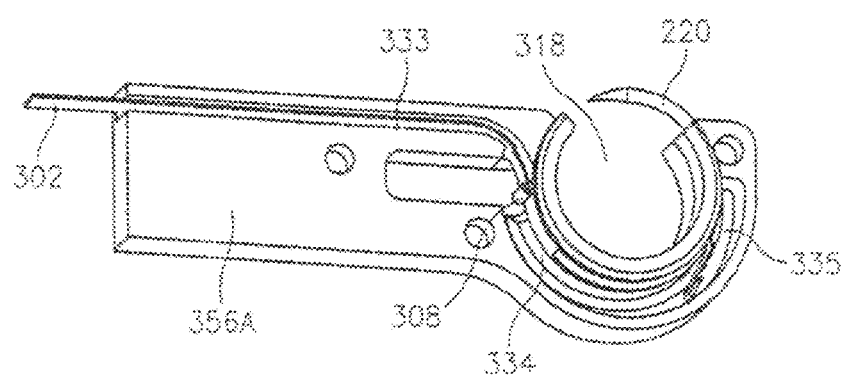
FIG. 40 shows a sectional view of the drive track of the second embodiment of the suture head assembly, depicting the course of the drive tendon, the drive pawl, and the anti-rotate spring in relation to the suturing needle.
Figure 41:
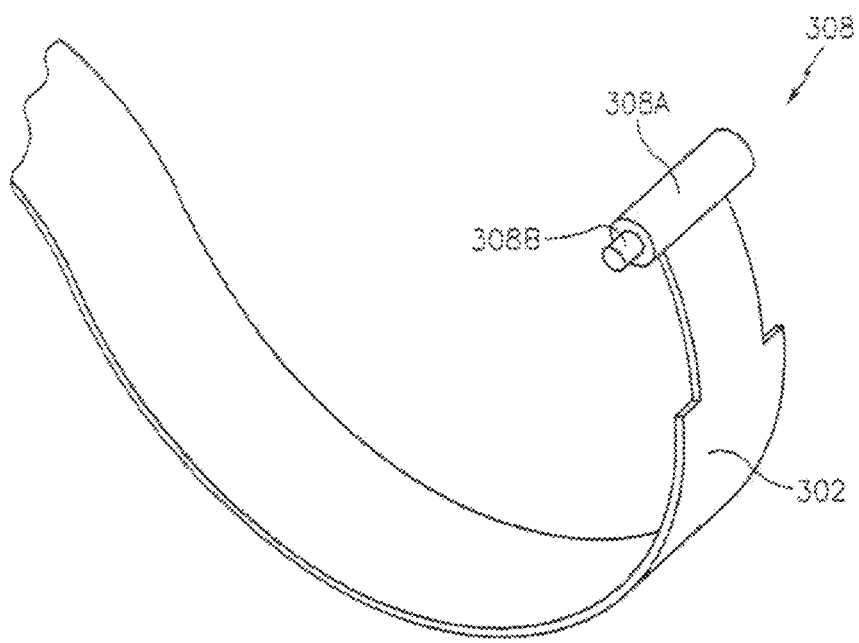
FIG. 41 is a close-up view of the distal end of the drive tendon with attached pawl.
Figure 42A:
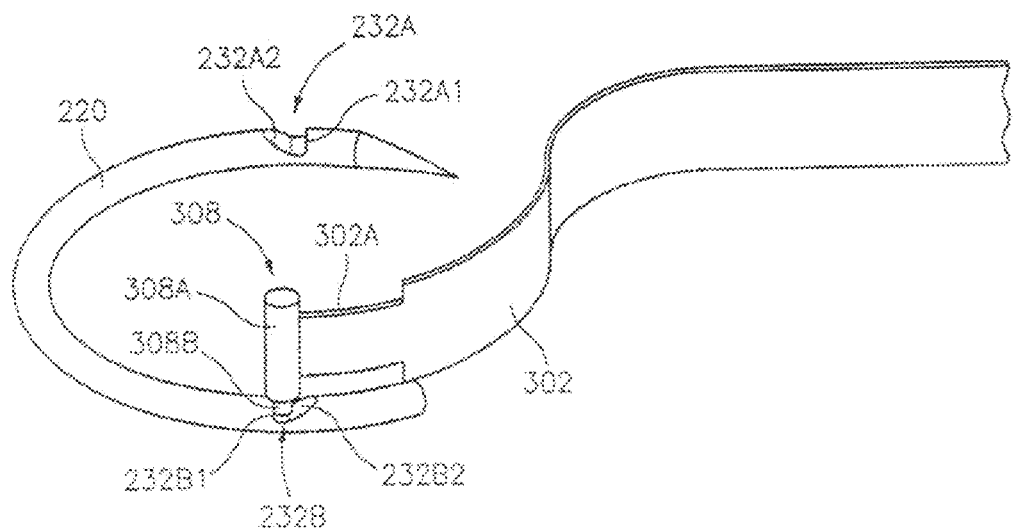
FIG. 42A is an isolated view of the tendon and pawl engaging a notch in the suturing needle
Figure 42B:
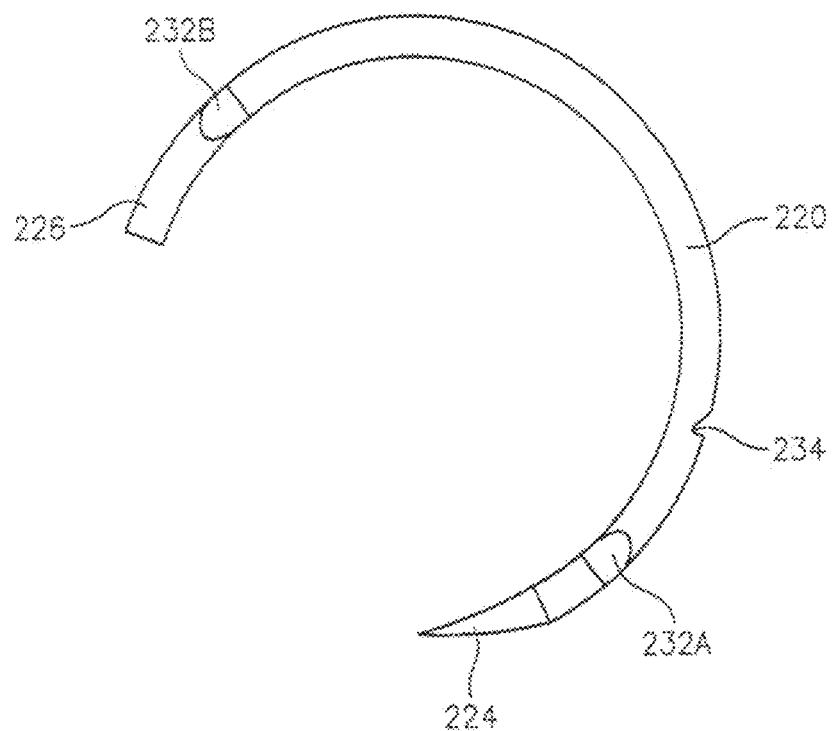
FIG. 42B is an isolated view of an exemplary suturing needle that may be used with the second suturing head embodiment, showing a leading notch and a trailing notch on the side of the needle, and an anti-rotate notch on the outer circumference of the needle.

As shown in FIG. 40, the tendon 302 is situated in a drive track 333 within the drive track component 356A of the suture head assembly 356. The drive track 333 is substantially straight until it reaches the distal portion of the suture head assembly 356, which at this point is shaped to define an aperture 318. At this location the drive track 333 in one embodiment divides into an engagement track 334, and disengagement track 335, which each follow a curved path conforming to the contour of the suturing needle 220. As shown in FIG. 41, tendon 302 flexes to conform to the shape of the engagement and disengagement tracks 334 and 335. FIG. 41 shows a perspective view of the distal flexed end of tendon 302, to which is attached a cylindrical pawl 308. The pawl 308 consists of a pawl body 308A and a pawl tip 308B. The cylindrical shape of the pawl body 308A and pawl tip 308B reduce the frictional resistance to movement of the tip of tendon 302 within engagement and disengagement tracks 334 and 335. Other cross-sectional shapes of the pawl assembly 308A and 308B are also possible, including, for example, an oval, a square a rectangle, or other more complex shapes. Moreover, the pawl body can also be constructed as a roller bearing, further reducing frictional resistance to the fore and aft motion of the tendon 302. FIG. 42A shows how the pawl tip 308B engages a trailing notch 232B or leading notch 232A on needle 220 to allow the tendon 302 to advance the needle 220 within its track 332. FIG. 42B shows the needle 220 in isolation, in which the drive notches 232A and 232B are located on the side of the needle 220, and the anti-rotate notch 234 is located on the outer circumference of the needle 220. A pointed end 224 pierces the target tissue during forward rotation of the needle 220, and suture material 246 is attached to the blunt end 226 of needle 220.

In one embodiment, notches 232A and 232B have a substantially perpendicular leading wall 232A1 and 232B1 against which the pawl tip 308B can engage and move the needle forward in its track 332; whereas the angled trailing walls 232A2 and 232B2 allow the pawl tip 308B to slide smoothly into position in the notches 232 and 233 as it advances within the engagement track 334. The leading walls 232A1 and 232B1 of notches 232A and 232B can also be inclined away from the pointed end of the needle, the angle of inclination being in the range of about 91 degrees to about 160 degrees with respect to the surface of the needle. The trailing walls 232A2 and 23B2 of notches 232A and 232B can also be inclined away from the pointed end of the needle, the angle of inclination being in the range of about 91 degrees to about 160 degrees with respect to the surface of the needle.

Alternatively, the trailing wall 232B2 of trailing notch 232B can also be made substantially perpendicular to the surface of the needle, with a gap between the leading wall 232B1 and the trailing wall 232B2 large enough to accommodate the pawl tip 308B. This embodiment allows the user either to advance the needle 220 by pushing the tendon 302 distally, or move the needle backwards by pulling the tendon 302 proximally when the pawl tip 308B is engaged in the trailing notch 232B. The surgeon can thus 'back out' the needle from the tissue being sutured when an obstacle is encountered that prevents complete penetration of the needle 220, or when repositioning of the needle in tissue is desired for other reasons. Under these circumstances, the leading wall 233A1 of leading notch 232A is preferably not angled away from the pointed end in order to avoid a 'barb-like' structure that would impede reversal of the needle path in tissue. In addition, the leading wall 233A1 can have a chamfered or rounded corner at the junction with the surface of needle 220 to facilitate backing the needle out of tissue. For the same reasons, the anti-rotate notch 234 can have a leading wall that does not angle away from the pointed end 224 of the needle 220, and it can have a chamfered or rounded corner at the junction with the surface of the needle 220. The trailing wall 232B2 of trailing notch 232B can also be constructed with a chamfered or rounded corner to facilitate forward movement of the needle through tissue.

Figure 43:
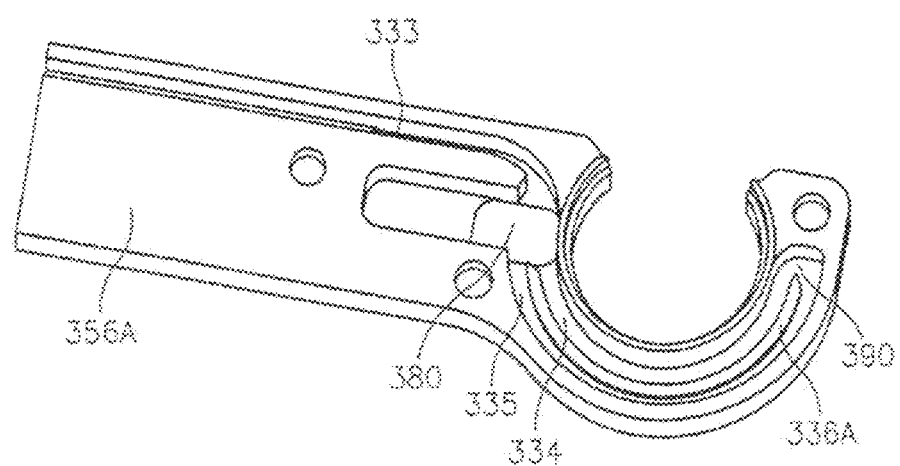
FIG. 43 is a sectional view of the inside structure of the drive track component of the second embodiment of the suture head assembly, without the tendon, pawl, anti-rotate spring and needle present to highlight the engagement and disengagement tracks, including a flat spring in the proximal chamber used to press the pawl against the drive notch of the needle.

As shown in FIG. 43, in one embodiment, the track 333 divides into engagement track 334 and disengagement track 335. Engagement track 334 is adjacent to and side-by-side with the needle track 332. Disengagement track 335 is adjacent to the outside circumference of engagement track 334. Pawl body guides 336A (FIG. 43) and 336B (FIG. 44) separate engagement track 334 from disengagement track 335, except for a gap between the pawl body guides 336A and 336B running the length of the tracks 334 and 335. (best shown in FIG. 46A) The base of pawl body guide 336A is either formed or attached along the inside wall of the drive track side 356A of suture head assembly 356. The base of pawl body guide 336B is either formed or attached along the inside wall of the needle track side 356B of suture head assembly 356. The pawl body guides 336A and 336B terminate short of the ends of the tracks 334 and 335, both at their proximal and distal ends, at proximal chamber 380 and distal chamber 390. This allows engagement track 334 to be in full communication with disengagement track 335 at both the proximal chamber 380 and the distal chamber 390 of the tracks. Tendon 302 moves only within engagement track 334, whereas the distal end 302A of tendon 302 and pawl 308 can move in engagement track 334 when driving needle 220, and move in disengagement track 305 when returning to proximal chamber 380. At the proximal end 308 of the engagement and disengagement tracks 334 and 335 (i.e. at the proximal chamber 380), the spring force caused by tendon 302 being flexed in a downward direction causes the pawl 308 to move up into the proximal end of engagement track 334. As the tendon moves distally in the engagement track 334, it engages the trailing notch 232B or leading notch 232A of needle 220, moving the needle 220 forward in its track 332. When the pawl 308 reaches the distal end of the track 334 at the distal chamber 390, the tendon 302 is flexed in an upward direction, and the spring force of tendon 302 now exerts a downward force on the pawl 308. The pawl 308 drops down into the distal end of disengagement track 335. The distal end of tendon 302 comprises a narrowed segment 302A, allowing this distal segment to travel within the disengagement track 335 as tendon 302 is pulled proximally, because the narrower dimension of the distal end of tendon 302 clears the pawl body guides 336A and 336B. The more proximal portion of tendon 302, at full width, continues to travel in engagement track 334, being held in place by the pawl body guides 336A and 336B.

Figure 45:
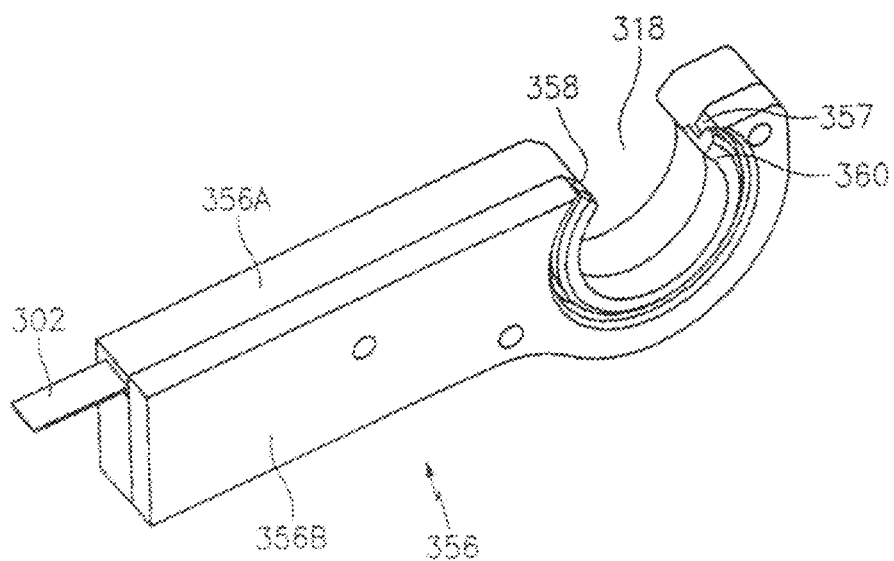
FIG. 45 is a top perspective view of the second embodiment of the suture head assembly, showing the placement of the thrust collar over the lateral side of the needle track, enclosing the needle within it.
Figure 46A:
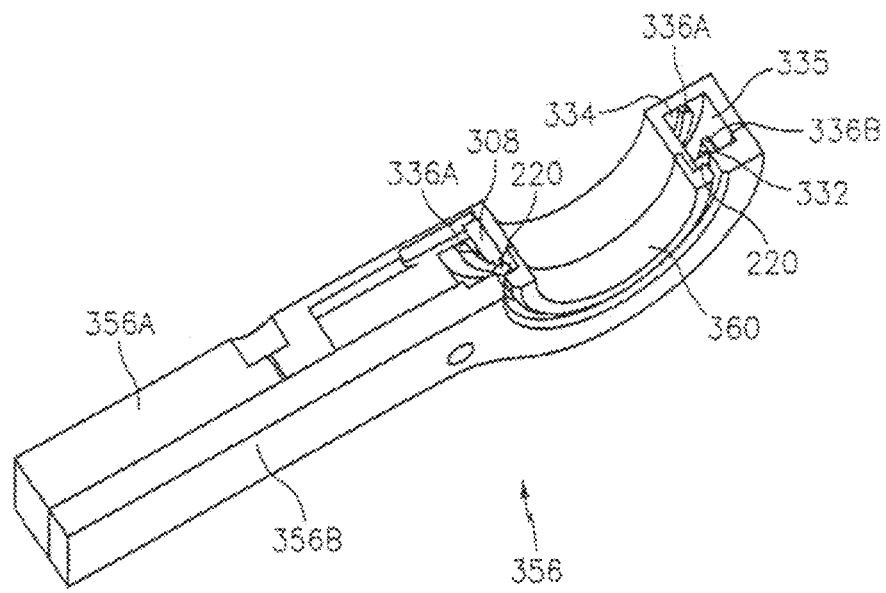
FIG. 46A is a sectional view through the upper portion of the second embodiment of the suture head assembly, revealing the cross-section of the pawl as it engages the trailing notch of the needle, and showing the distal ends of both pawl body guides, separating the engagement track from the disengagement track. The relationship of the thrust collar to the needle and needle track is also apparent.
Figure 46B:
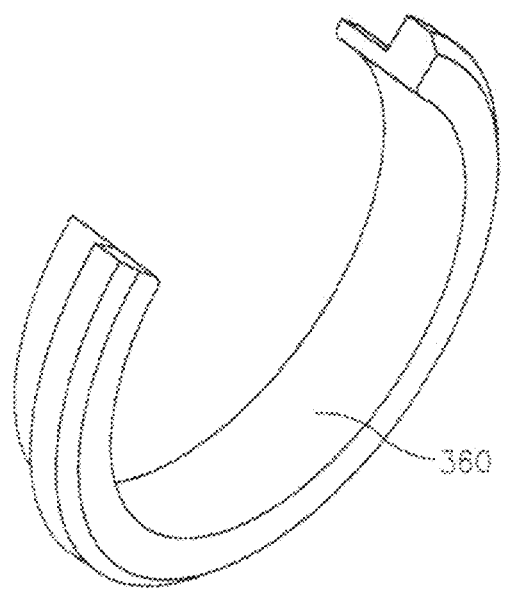
FIG. 46B is a view of the thrust collar in isolation.

FIG. 45 shows a top perspective view of the suture head assembly 356. The drive track side 356A is mated to the needle track side 356B. The needle track 332 is formed on the outside surface of the needle track side 356B of the suture head assembly 356. In this embodiment, a second opening 357, located at the distal end of aperture 318, is where the pointed end 224 of needle 220 exits the device. A first opening 358, located at the proximal end of aperture 318, is where the pointed end 224 of needle 220 re-enters the suture head assembly 356 after penetrating the target tissue. FIG. 46A shows a cutaway top perspective view of suture head assembly 356, in which the roof of track 333, the proximal chamber 380, and the distal chamber 390 have been cut away. The pawl 308 can be seen in cross-section within the proximal end of engagement track 334, adjacent to the cross-section of needle 220 at trailing notch 232B. Pawl tip 308B is engaged in trailing notch 232B of needle 220. The pawl 308 is held within the track by pawl body guides 336A and 336B. The narrow segment 302A of tendon 302 can pass through the gap between pawl body guides 336A and 336B. Thus while the main portion of tendon 302 remains within engagement track 334, the pawl 308 and narrow segment 302A of tendon 302 can travel either in engagement track 334 or engagement track 335. A thrust collar 360, shown in FIG. 46A (and in isolation in FIG. 46B) snaps over the outside of needle 220 into suture head assembly 356 to hold needle 220 within its needle track 332. Alternatively, a cartridge 88, as shown in FIG. 2A and FIG. 2B, can be used, which can then be attached to a cartridge holder assembly 90. A cartridge 88 can provide operating room personnel with the added safety of avoiding inadvertent puncture from handling an exposed needle 220.

Figure 44:
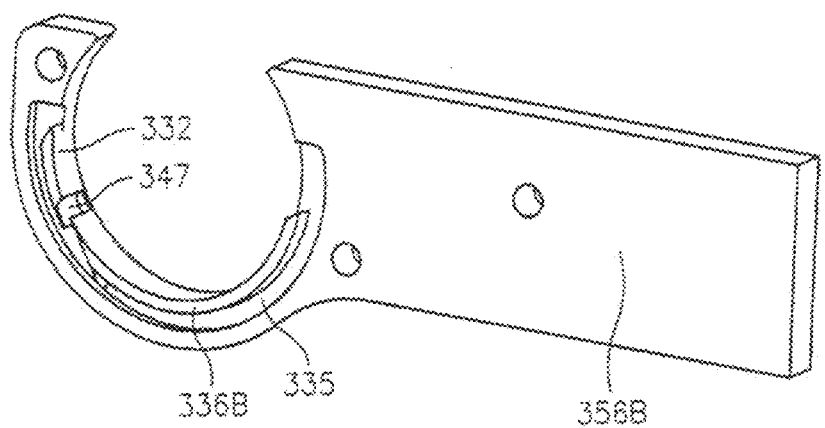
FIG. 44 is a perspective view of a portion of the inside structure of the needle track component of the second embodiment of the suture head assembly, showing one of the pawl body guides, and the aperture through which the anti-rotation spring engages the outer circumference of the needle.
Figure 47:
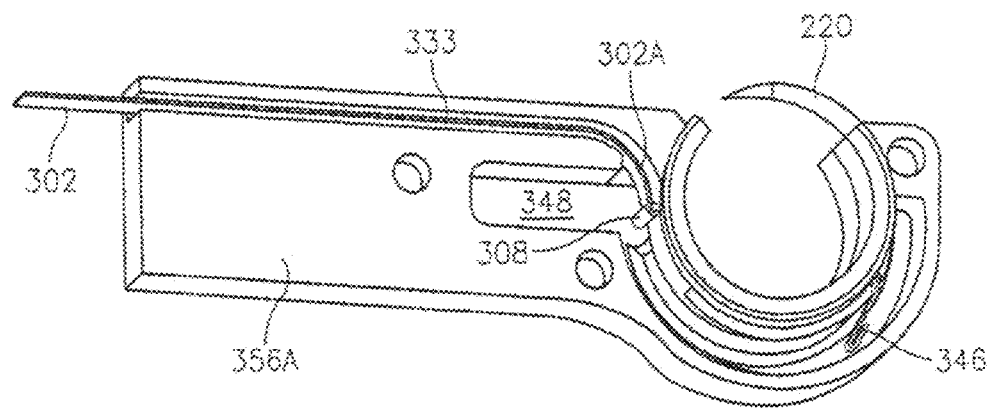
FIG. 47 is a sectional view of the second embodiment of the suture head assembly showing the pawl body positioned against the flat spring, which urges the pawl tip against the side of the needle. In this view, the needle is partially spanning the aperture of the suture head assembly, and the anti-rotate spring is visible as it contacts the outer circumference of the needle.
Figure 48:
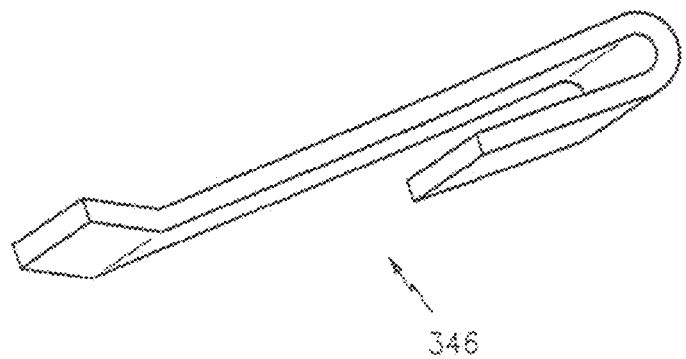
FIG. 48 is an isolated view of the anti-rotate spring.

A further enhancement of suture head assembly 356 is shown in FIG. 47. An anti-rotate spring 346 (shown in isolation in FIG. 48), anchored inside suture head assembly 356 can engage a notch on the outer circumference of needle 220 to prevent backward migration of needle 220 in its track 332. As shown in FIG. 44, the anti-rotate spring 346 contacts the surface of needle 220 through an aperture 347 lateral to the disengagement track 335 so as not to interfere with movement of the distal end of tendon 302 and pawl 308. In a preferred embodiment, the anti-rotate notch 234 is located on the outer circumference of needle 220, and sufficiently distally along the needle to cause engagement of the anti-rotate spring 346 only when the pointed end of needle 220 is within the confines of suture head assembly 356.

Figure 49:
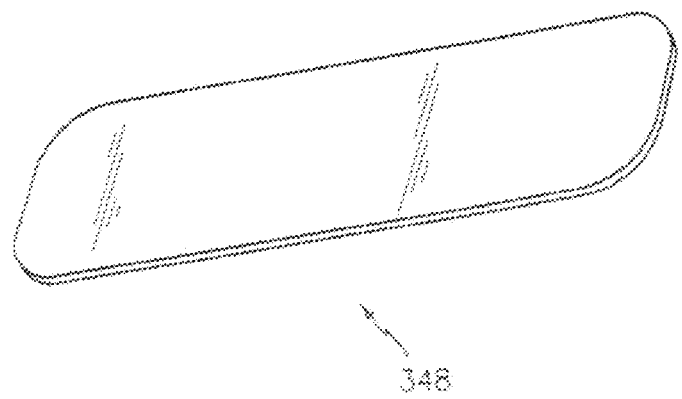
FIG. 49 is an isolated view of the flat spring, which presses against the pawl body to urge the pawl tip against the side of the needle.
Figure 50B:
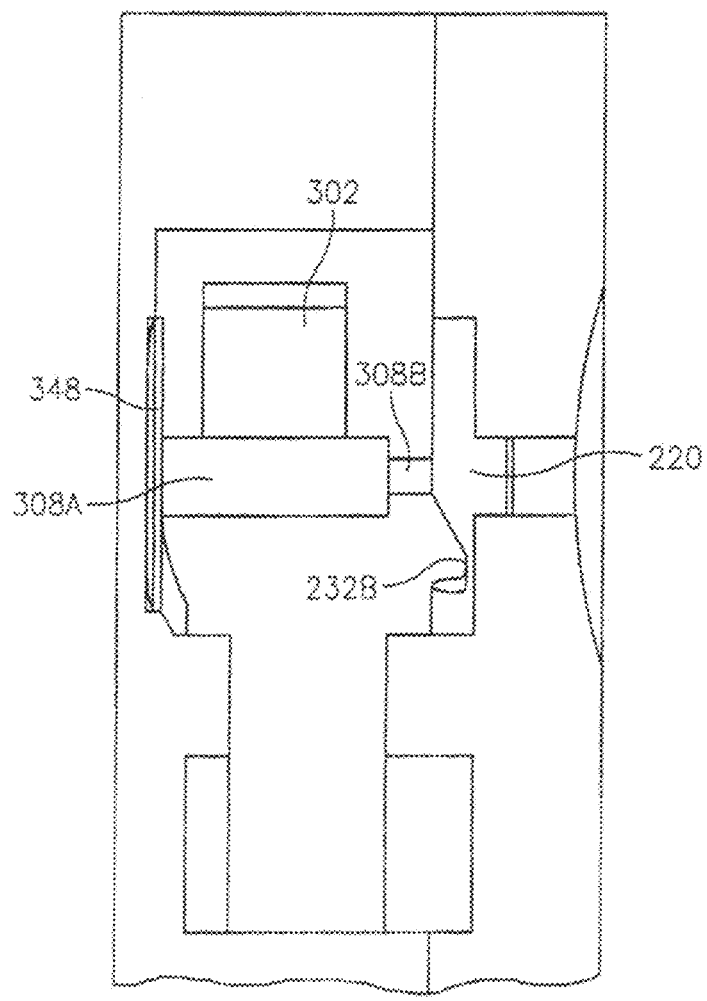
FIG. 50B is a view through section B-B of FIG. 50A showing the pawl tip pressed against the side of the needle above the notch by a compressed flat spring.
Figure 51C:
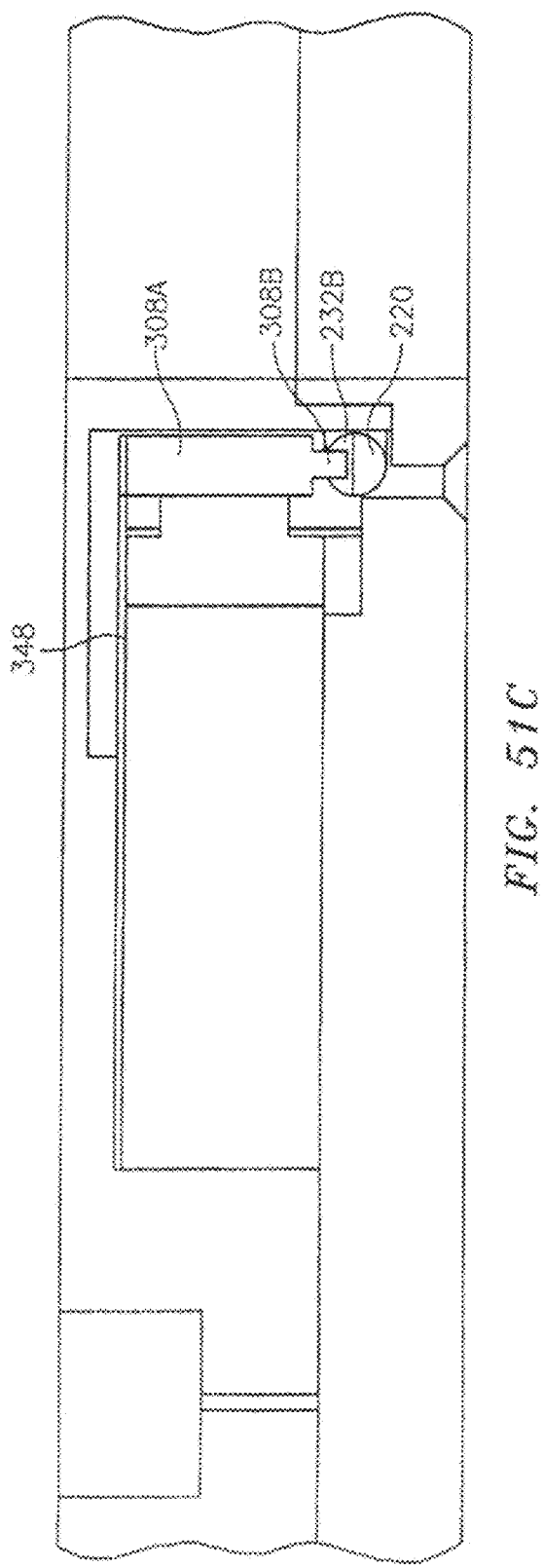
FIG. 51C is a top view through section C-C of FIG. 51A showing the flat spring in a non-deflected state with the pawl tip advanced within the notch of the needle, now in position to drive the needle forward.

An additional feature to coax pawl 308 to engage the notch 232A or 232B of needle 220 is shown in FIG. 47. A flat spring 348 (shown in isolation in FIG. 49) is situated within proximal chamber 380 of the drive track side 356A of suture head assembly 356. The flat spring 348 urges the pawl 308 against the side of needle 220 to engage the pawl tip 308B with either the trailing notch 232B or leading notch 232A. The force exerted by flat spring 348 is substantially weaker than the spring force exerted by the downwardly flexed tendon 302, allowing the distal end of tendon 302 and the pawl 308 to move into position at the proximal end of engagement track 334, compressing flat spring 348 if necessary. Thus it is possible for pawl 308 to engage the notch 232A or 232B of needle 220 even if the pawl 308 and notch 232A or 232B are not exactly adjacent to one another. FIG. 50A is a cross-sectional view of suture head assembly 356 showing pawl 308 positioned immediately proximal to trailing notch 232B of needle 220. FIG. 50B is a view of FIG. 50A through section B-B. Pawl tip 308B is pressed against the side of needle 220 immediately proximal to notch 232B by compressed flat spring 348. FIG. 50C is a view of FIG. 50A through section C-C. Flat spring 348 deflected by pawl 308, maintaining pressure of pawl tip 308B against the side of needle 220. FIG. 51A is a cross-sectional view of suture head assembly 356 showing pawl 308 positioned within trailing notch 232B of needle 220. FIG. 51B is a view of FIG. 51A through section B-B. At this point, pawl tip 308B is engaged with notch 232B of needle 220, spring 348 is in a relaxed position, and pawl 308 is aligned with the side wall of engagement track 334, allowing it to proceed distally to drive the needle 220 within its needle track 332. FIG. 51C is a view of FIG. 51A through section C-C. Flat spring 348 is now in a relaxed position, and pawl tip 308B is situated within notch 232B of needle 220. Once the pawl 308 moves distally within engagement track 334, the confines of the track wall itself keep the pawl tip 308B engaged with notches 232B or 232A.

Figure 53:
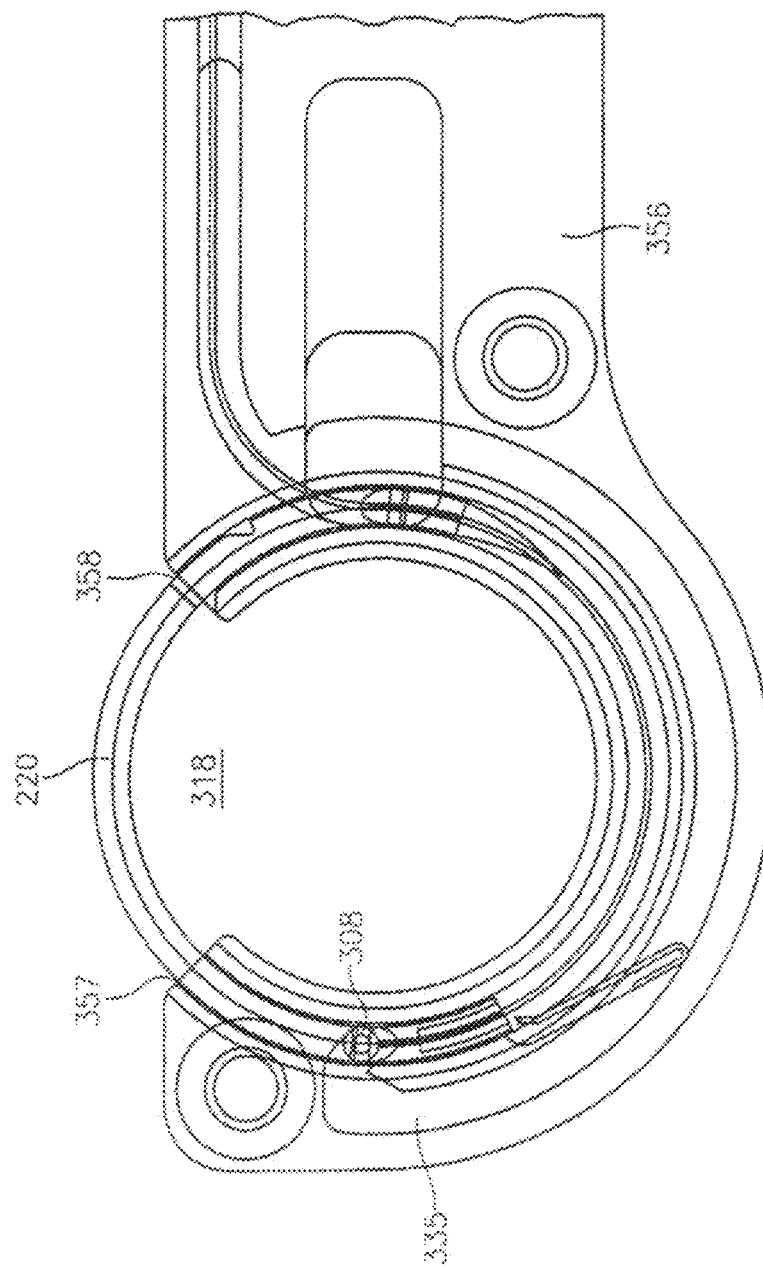
FIG. 53 is a sectional side view of the second embodiment of the suture head assembly, showing the needle at the end of the push stroke of the first suturing cycle, the pawl having pushed the needle through the aperture, and ready to disengage from the trailing notch.
Figure 54:
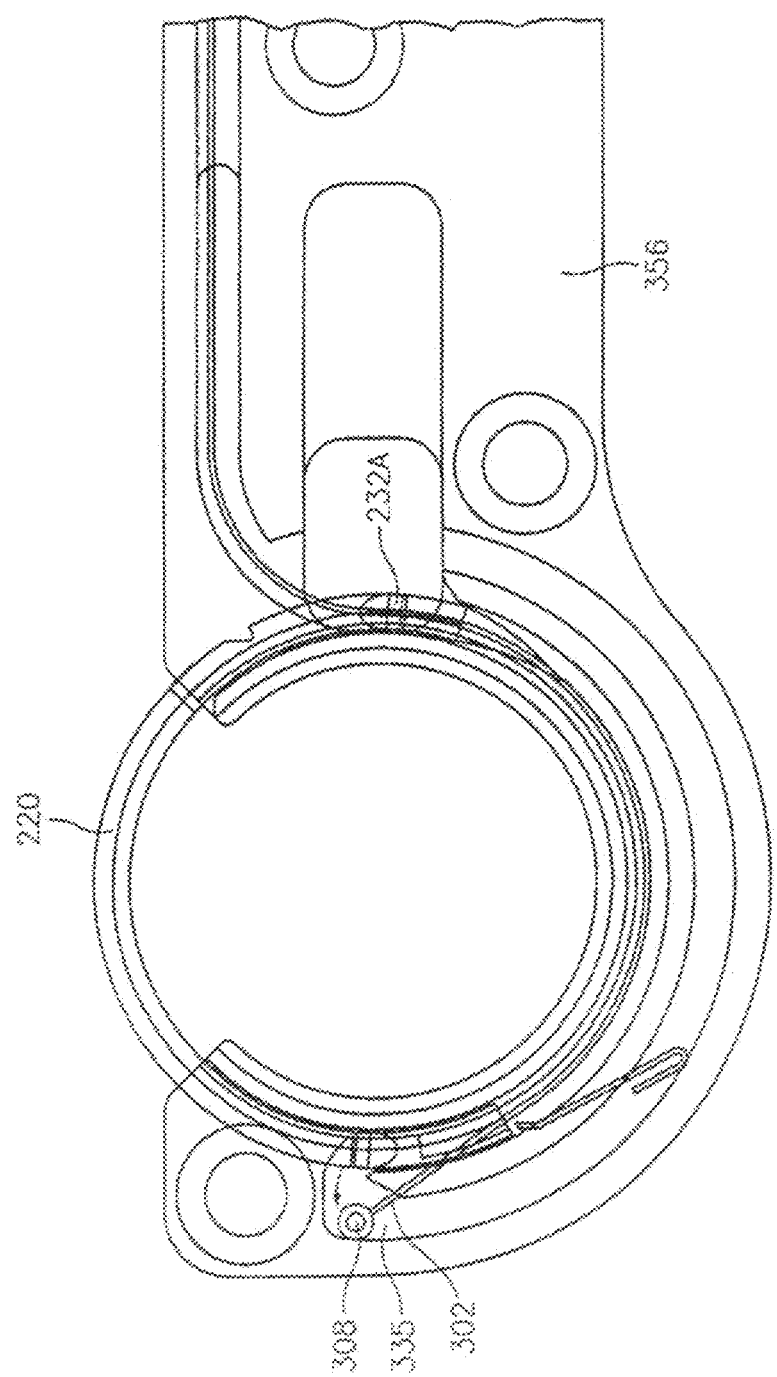
FIG. 54 is a sectional side view of the second embodiment of the suture head assembly, showing the pawl being released from the trailing notch into the distal end of the disengagement track.
Figure 55:
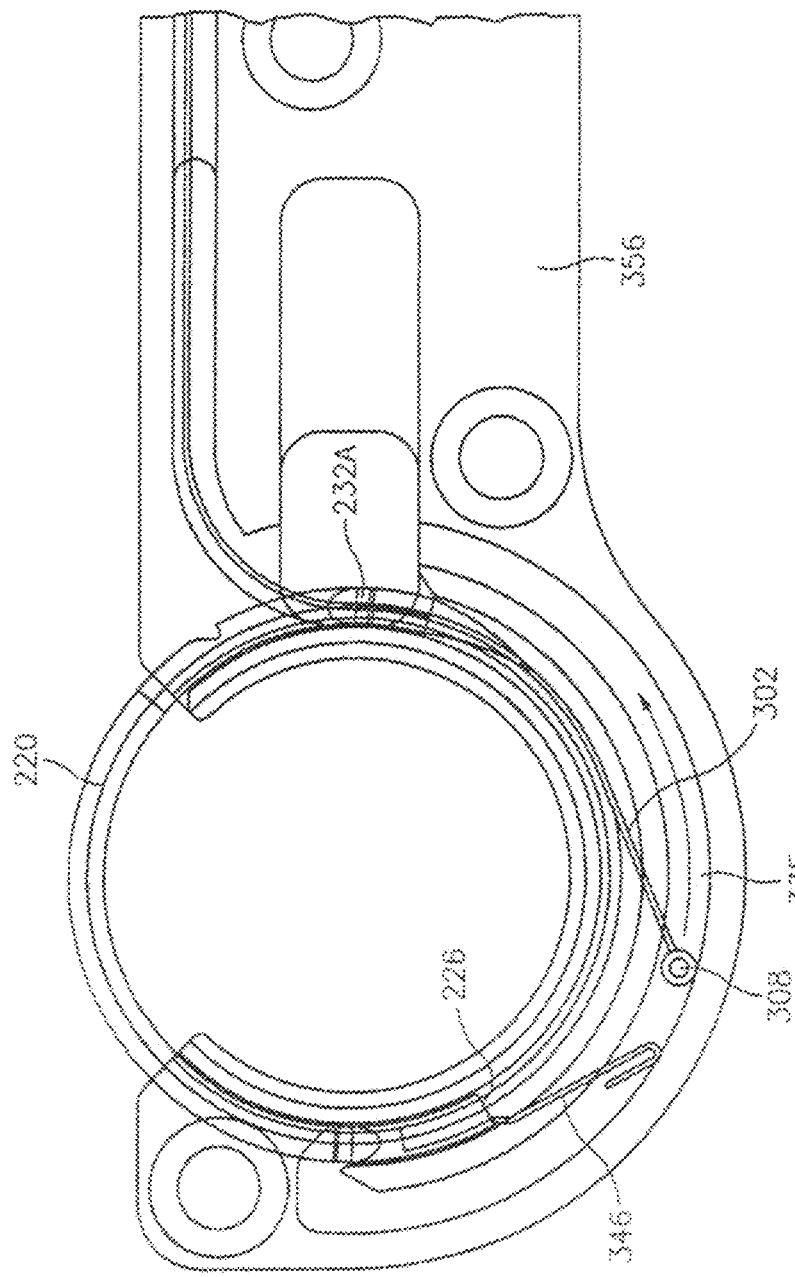
FIG. 55 is a sectional side view of the second embodiment of the suture head assembly, showing the pawl being pulled by the tendon to the proximal end of the track in the pull stroke of the first suturing cycle.
Figure 56:
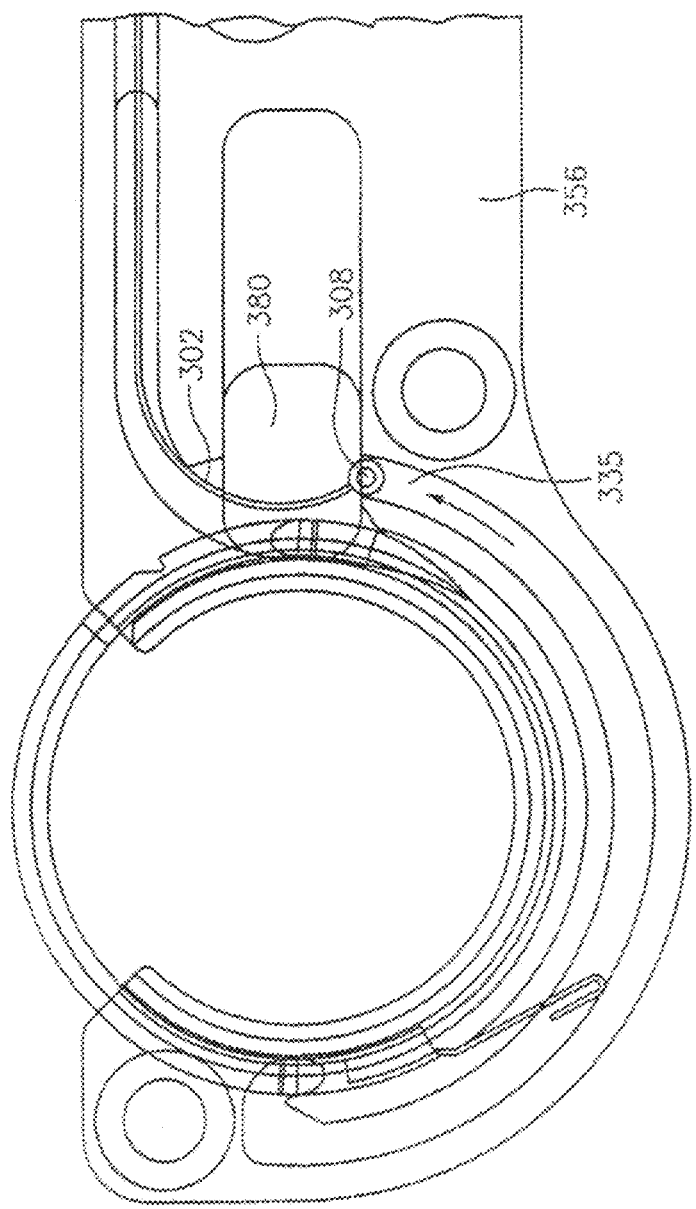
FIG. 56 is a sectional side view of the second embodiment of the suture head assembly, showing the pawl approaching the proximal chamber where the proximal ends of the engagement and disengagement tracks merge. The distal end of the tendon has been deflected away from the leading notch of the needle.
Figure 57:
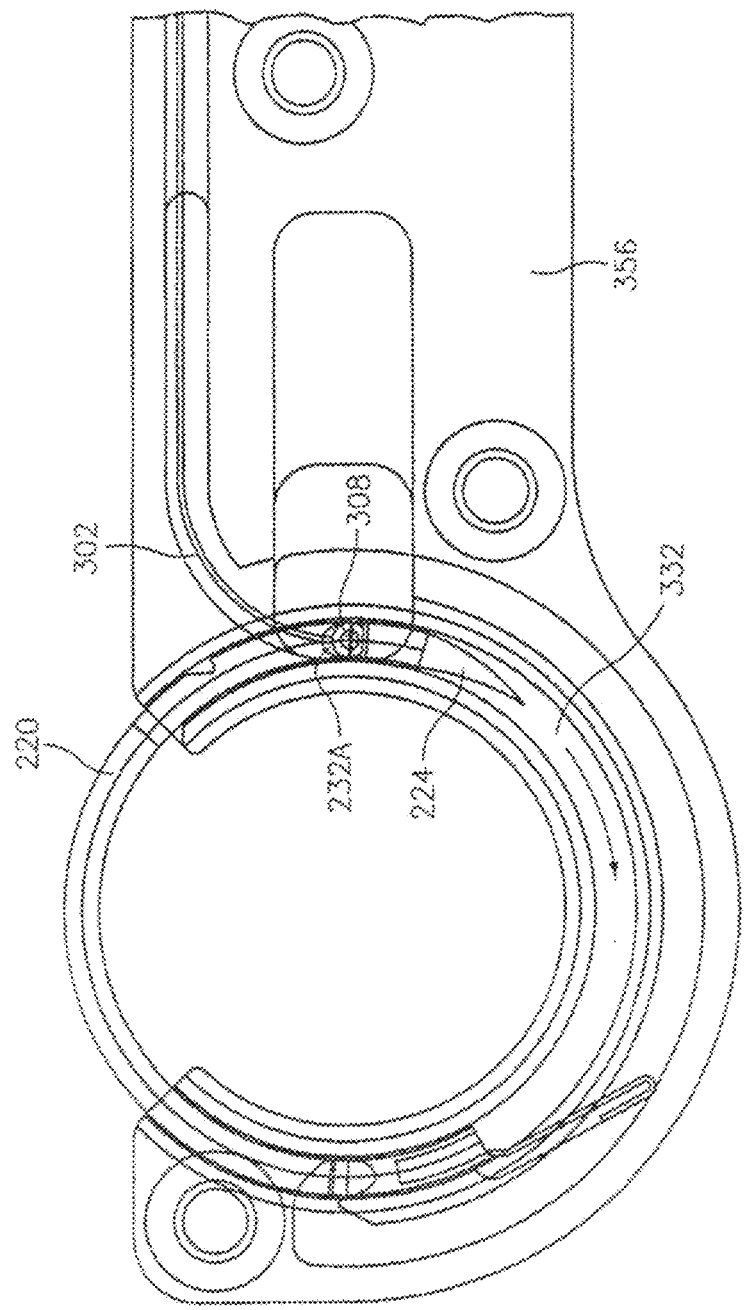
FIG. 57 is a sectional side view of the second embodiment of the suture head assembly, showing the pawl being released into the leading notch of the needle by spring force from the distal tendon that had been deflected as shown in FIG. 56.

FIGS. 52-59 are sectional views through the length of suture head assembly 356 showing the progression of a complete four stroke movement (two push-pull cycles) that causes needle 220 to undergo a 360 degree rotation within its track 332, penetrating the target tissue in the first stroke of the first cycle. In FIG. 52, the pawl 308 is situated at the proximal end of engagement track 334, and is engaged with notch 232B of needle 220. Anti-rotate spring 346 is engaged with the anti-rotate notch 234 on the outer circumference of needle 220, preventing it from moving in a reverse direction. In FIG. 53, the tendon 302 has been pushed distally in a first stroke, and has driven pawl 308 to the distal end of engagement track 334. When the ends of pawl guides 336A and 336B have been cleared, the distal end of tendon 302 and pawl 308 snap by spring force into the distal end of disengagement track 335. In this embodiment, movement of needle 220 by pawl 308 in this stroke has caused the pointed end of needle 220 to exit the second opening 357 of suture head assembly 356, traverse the aperture 318, penetrated the target tissue, and re-entered the first opening 358 of suture head assembly 356. In FIG. 54, the pawl 308 and the distal end of tendon 302 have dropped into the distal end of the disengagement track 335 by spring force of the upwardly deflected tendon 302. The pull stroke in the first suturing cycle is shown in FIG. 55. The pawl 308 is being pulled by tendon 302, which is being retracted proximally by the surgeon via the handle 60 or 160. Backward migration of the needle 220 is prevented by the engagement of anti-rotate spring 346 against the hub or blunt end 226 of needle 220. This helps to keep the leading notch 232A of needle 220 aligned with the proximal chamber 380, where the pawl 308 can engage it. In FIG. 56, the pawl 308 has reached the end of the pull stroke at the proximal end of disengagement track 335. At this point the tendon 302 is significantly deflected downward, generating a spring force to drive pawl 308 upward into the proximal end of engagement track 334, after it has cleared the pawl body guide 336A and 336B. In FIG.

Figure 58:
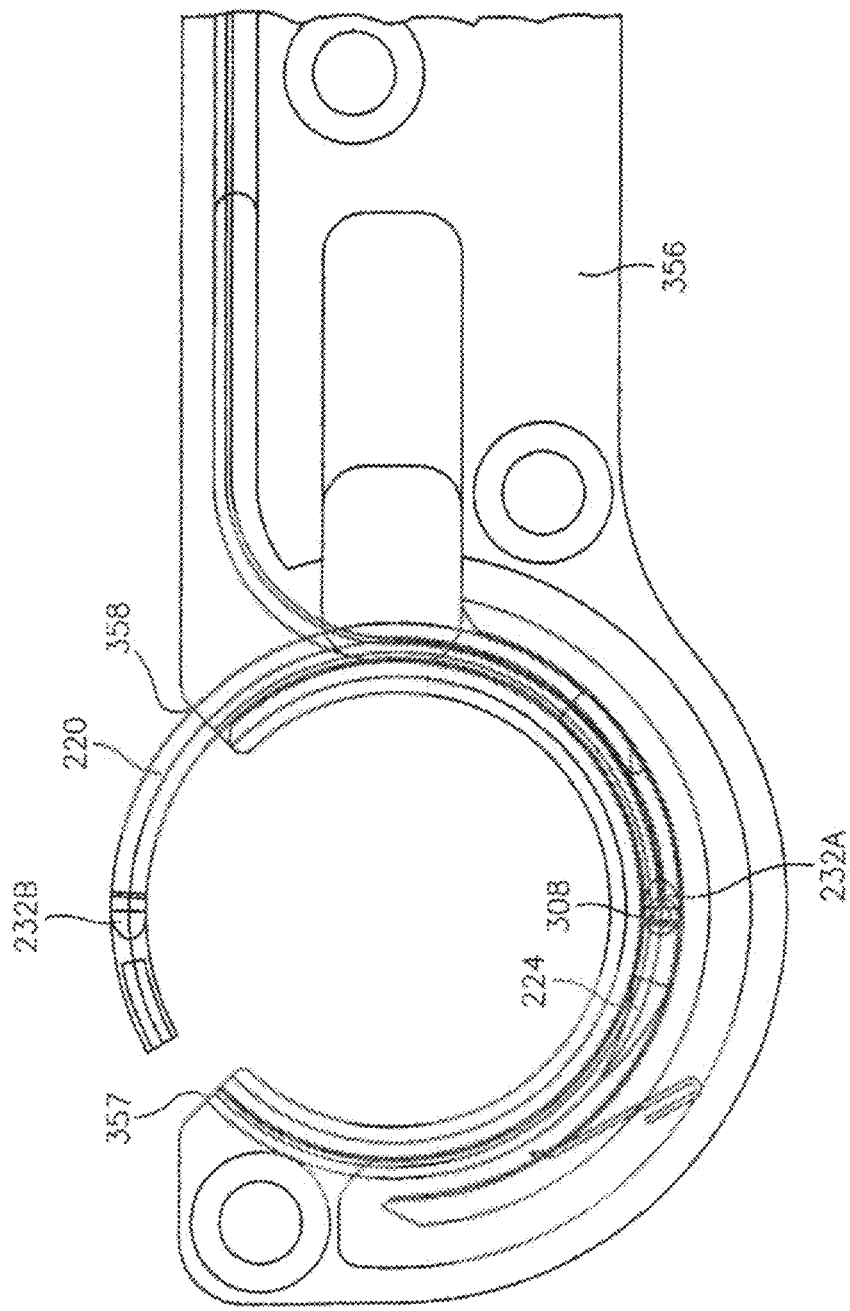
FIG. 58 is a sectional side view of the second embodiment of the suture head assembly, showing the push stroke of the second suturing cycle, in which the pointed end of the needle is being advanced to the 'home' position by the pawl.
Figure 59:
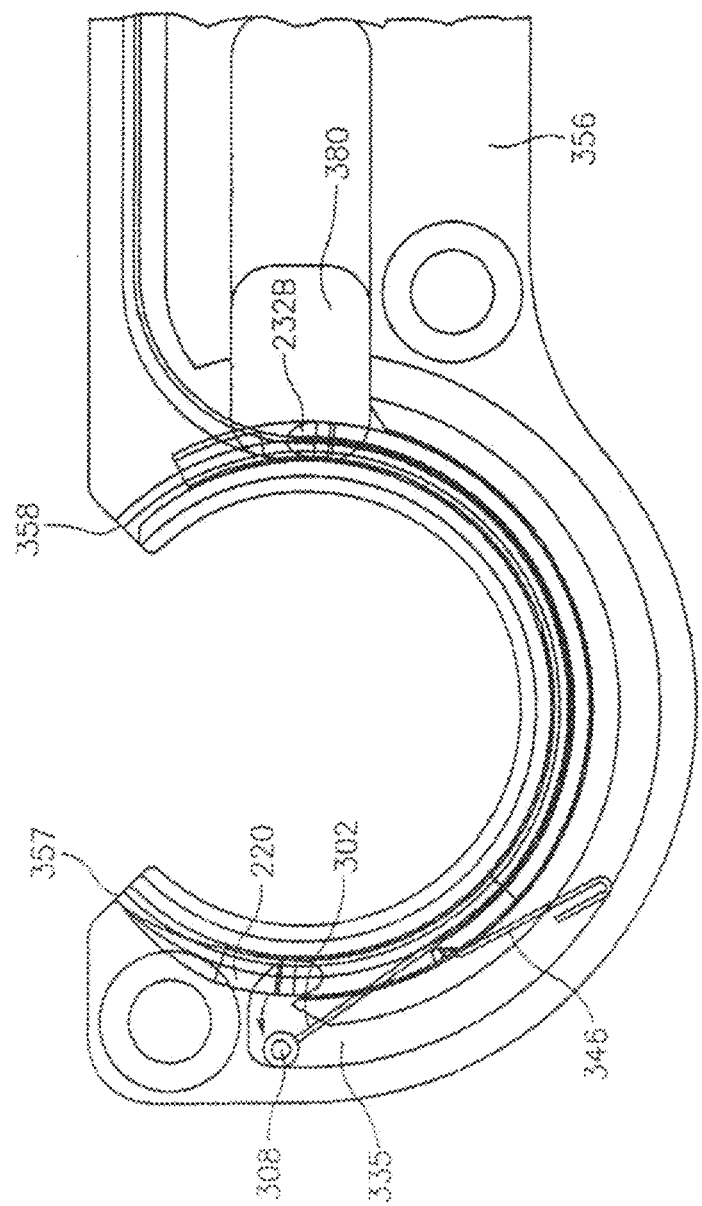
FIG. 59 is a sectional side view of the second embodiment of the suture head assembly, showing the push stroke of the second suturing cycle having been completed, the pawl being urged into the distal end of the disengagement track by the spring force of the distal tendon, and the trailing notch in proper alignment with the proximal chamber.
Figure 60:
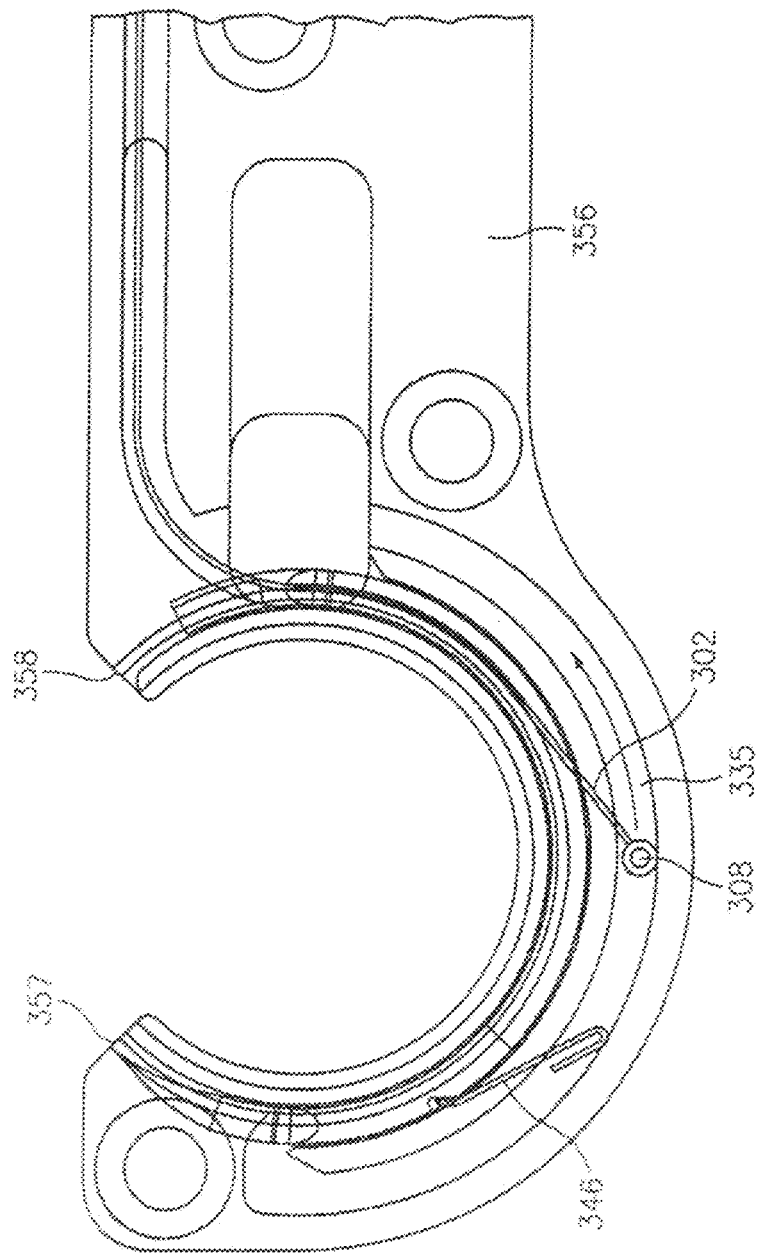
FIG. 60 is a sectional side view of the second embodiment of the suture head assembly, showing the pull stroke of the second suturing cycle, bringing the pawl back to the proximal end of the disengagement track to be positioned to re-initiate the suturing cycle. Backward rotation of the needle is prevented in this stroke by the anti-rotate spring engaging the anti-rotate notch of the needle.

57, the pawl 308 has been driven by spring force into engagement with the leading notch 232A of needle 220. The push stroke of the second suturing cycle involves pushing the tendon 302 distally, driving the pawl 308 and pointed end 224 of needle 220 toward the distal end of needle track 332 (visually indistinguishable from engagement track 334 in this view). This is shown in FIG. 58, where the pointed end 224 of needle 220 has advanced half-way through needle track 332. In FIG. 59, the push stroke of the second suturing cycle has been completed, with the pawl having dropped into the distal end of disengagement track 335 by spring force from the upward deflection of tendon 302. The needle 220 has returned to its home position. Backward movement of the needle 220 is prevented by anti-rotate spring 346 engagement with the anti-rotate notch 234 of needle 220. The trailing notch 232B of needle 220 is in position to be engaged by pawl 308 at the proximal end of engagement track 334. As shown in FIG. 60, the pull stroke of the second suturing cycle is a retraction of tendon 302 proximally, pulling the pawl 308 proximally within disengagement track 335 and bringing it into position in the proximal chamber 380 to re-engage the trailing notch 232B of needle 220. Backward migration of needle 220 is prevented by anti-rotation spring 346 engaging the anti-rotation notch 234 of needle 220. The suturing cycle is ready to resume if desired at this point.

Those skilled in the art will recognize that the movement of the distal end 302B of tendon 302 and pawl 308 into and out of notches 232A and 232B can be effected by springs situated within the suture head assembly 356 at the beginning of disengagement track 335 and at the end of engagement track 334. Externally applied spring force, or even the placement of ramps in the engagement and disengagement tracks can cause the pawl 308 to be re-directed into the proximal end of engagement track 334, and into the distal end of disengagement track 335.

It will also be apparent to those skilled in the art that the direction of travel of needle 220 can be reversed by having the home position for the trailing notch situated in the distal end of needle track 332. In this case, the pawl and tendon are situated at the distal end of engagement track 334 at the start of the first stroke of the first suturing cycle. The first (pull) stroke of the cycle would cause the pointed end of needle 220 to exit the first opening 358, pass through the target tissue, and re-enter the suture head assembly at the second opening 357. Structured in this way, the disengagement track 335 would be equipped with a spring or ramp to press the pawl 308 into the notch 232A or 232B at the distal end of the track, and with a spring or ramp to disengage the pawl 308 from the notch 232A or 232B at the proximal end of the track. Alternatively, the disengagement track 335 can be constructed so that it lies within the inner circumference of the engagement track 334 and needle track 332. Under this circumstance, the spring-like property of tendon 302 will naturally drive the pawl 308 into notch 232A or 232B at the distal end, and out of notch 232A and 232B at the proximal end.

In an embodiment, the entire suturing device 150 can be designed as a single unit which may be either reusable or disposed after a single use. In one embodiment, the entire suturing device 150 can be designed from a number of separable parts where each unit may be either reusable or disposed after a single use.

The suturing device 150 is configured to provide a "pistol like" grip for the user that includes an elongated barrel 154 and a handle 160 that extends from the proximal end of the elongated barrel 154. The elongated barrel 154 has either a linear or non-linear configuration, including but not limited to, straight, curved and angled configurations. A suture head assembly 156 is removably attached to the distal end of the elongated barrel 154. The suture head assembly 156 contains a portion of the drive mechanism 170 of the device 150. The working end of the suture head assembly 156 has a needle holder assembly 188 to which a suturing needle 220 may reside. A latch 210 forms a cover over the needle 220.

An arcuate suturing needle 220 having a sharp, pointed end 224 is slidably mounted in a circular track 192 of the needle holder assembly 188. The blunt end of the needle 226 is connected to the suturing material or thread 246. The needle 220 normally resides in a "home" position in the track 192 such that the gap in the arcuate suturing needle 222 is in alignment with an aperture 218 in the needle holder assembly 188. The sharp, pointed end of the needle 224 is situated on one side and entirely within the confines of the needle holder aperture 218; the pointed end of the needle 224 is, therefore, shielded by the needle holder assembly 188. The blunt end of the suturing needle 226 that is attached to the suturing material or thread 246 is located at the opposite side of the aperture 218. The sharp, pointed end of the needle 224 is, therefore, wholly contained within the needle holder assembly 188 and does not protrude beyond the housing of the needle holder assembly 188. Thus, the sharp pointed end of the needle 224 is not exposed to the user.

In accordance with the presently disclosed embodiments, the needle 220 may be releasably engaged by the needle driver 198 that is rotatably mounted within the suture head assembly 156 so that the needle 220 can be rotated from the home position by about 360 degrees about the central vertical axis of the needle holder assembly 188. Such a rotary action of the needle 220 causes the sharp point 224 to advance across the needle holder assembly 188 so as to span the aperture 218. Thus, when the device 150 is positioned such that the incised tissue segments to be sutured are situated at the needle holder assembly aperture 218, the needle 220 penetrates the tissue segments and spans the incision between them. A continued rotary movement of the needle 220 causes the needle 220 to return to the home position, and thereby causes the suturing material or thread 246 attached to the needle 220 to be pulled into and through the tissue in an inward direction on one side of the tissue incision, and upwards and out through the tissue on the opposite side of the incision. Thus, the suture material or thread 246 follows the curved path of the needle 220 to bind the tissues together with a stitch of material or thread 246 across the incision in a manner similar to manual suturing, wherein the needle 220 is "pushed" from the blunt end 226 and then "pulled" from the pointed end 224 by the pawl 198. Preferably, an anchoring mechanism is provided at the trailing terminal end of the suturing material or thread 246 to prevent the material 246 from being pulled completely through and out of the tissue segments. For example, the anchoring mechanism can be a pre-tied or a welded loop, a knot wherein the suture material or thread 246 is simply tied, or a double-stranded, looped suture is that attached to the suturing needle 220. The rotary movement of the needle 220 within the needle holder assembly 188 is accomplished by a pawl 198 that may be operated by the user by holding the suturing device 150 with one hand in a pistol-like grip around the handle 160, and using at least one finger of that hand to activate.

In accordance with further aspects of the invention, for purposes of illustration and not limitation, FIGS. 61-71 depict a further embodiment of a suturing head 500 for a suturing instrument.

Figure 61:
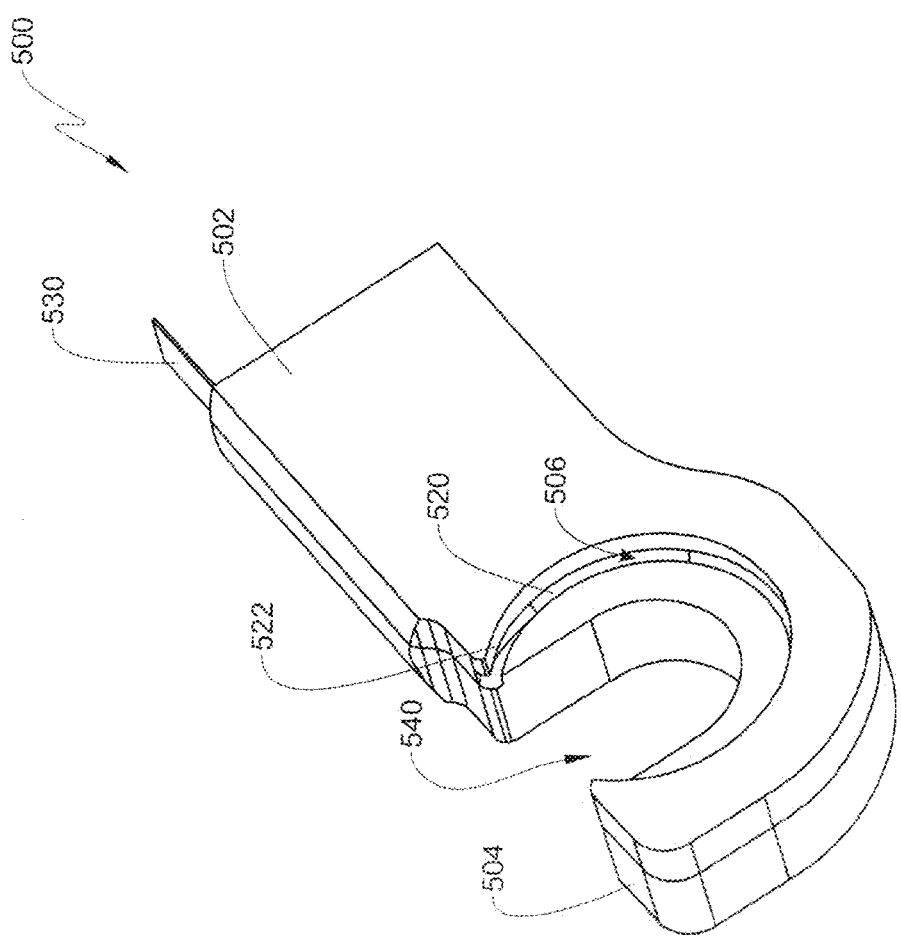
FIGS. 61-71B describe a further embodiment of a device made in accordance with the invention.
Figure 62:
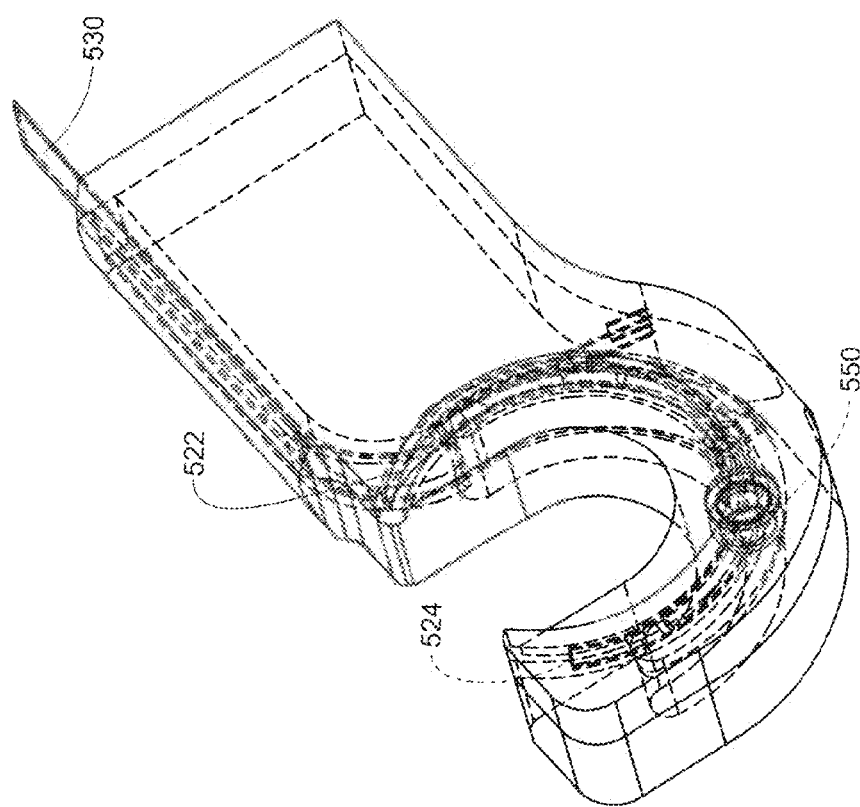
Figure 63:
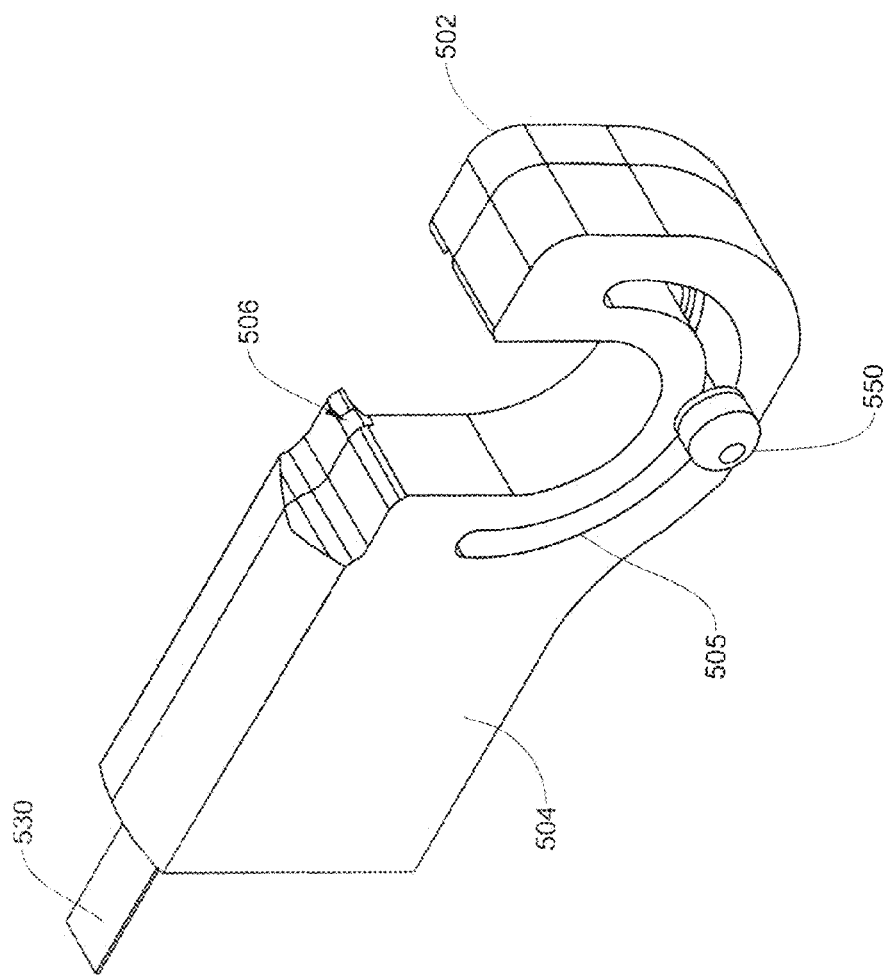
Figure 64:
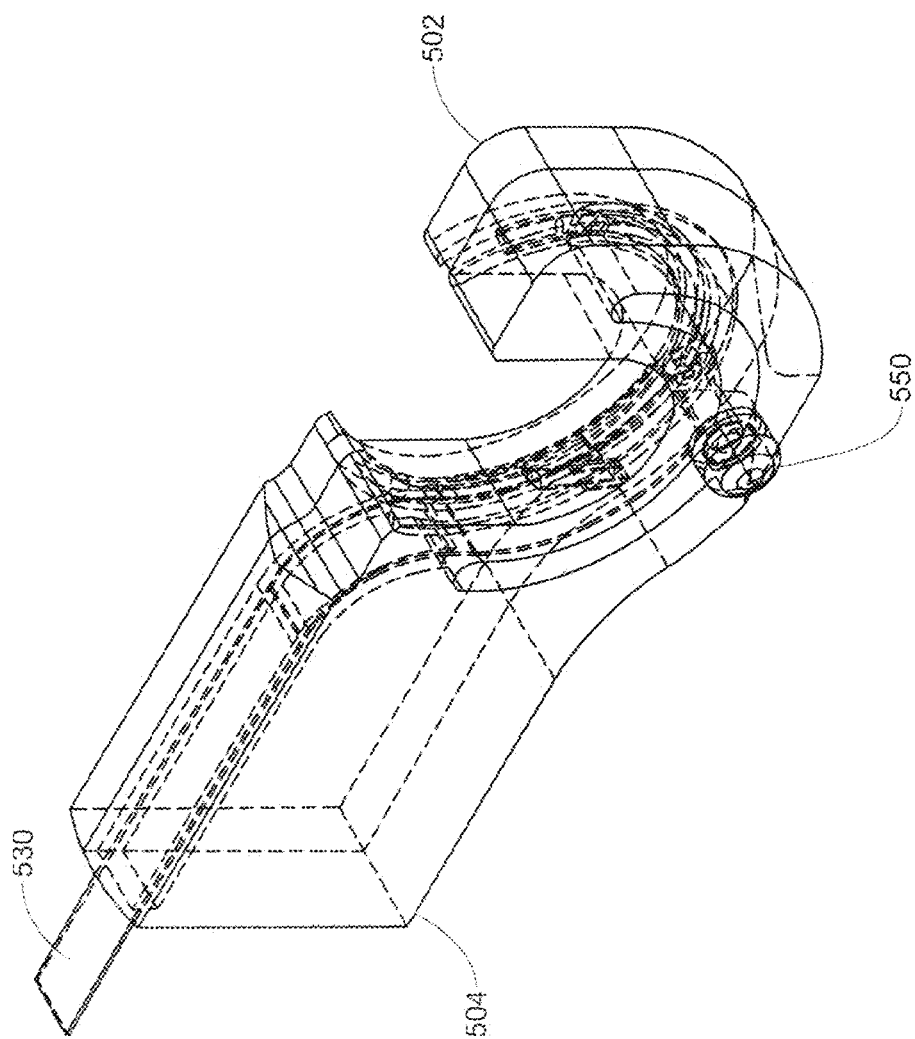

FIGS. 61-62 illustrate perspective views of this embodiment, both in plain view and showing hidden features, respectively. As illustrated, suturing head 500 is comprised of two main housing components, 502 and 504. Housing component 502 defines a portion of a needle track 506 that is complete when components 502, 504 are assembled. This embodiment is similar to that of FIG. 39, but with certain differences. Significantly, in contrast to the embodiment of FIG. 39, this embodiment operates by moving needle 520 through needle track 506 during a pull stroke of filament 530, rather than during a push stroke. Distal end 534 of filament 530 is attached to an engagement mechanism 550 that selectively engages notches formed in the needle 520 in a manner similar to other embodiments described herein. As depicted in FIG. 63, engagement mechanism rides in an arcuate track 505 formed in housing component 504 that is generally concentric with the needle track 506. Suturing head 500 includes a tissue capture gap 540, similar to the embodiment of FIG. 39.

Figure 65:
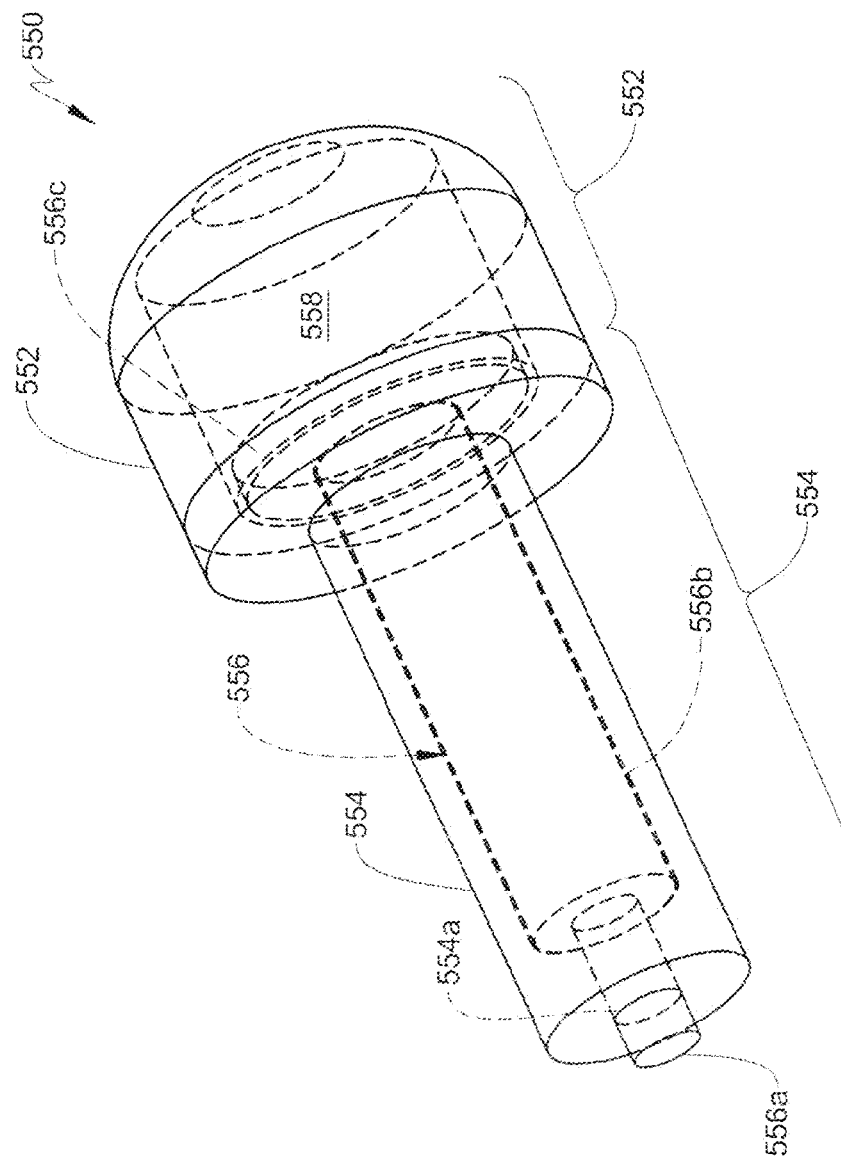

FIG. 65 depicts the engagement mechanism that rides in track 505. As depicted, engagement mechanism 550 includes four main components: cap 552, sleeve 554, piston 556 and a chamber 558 housing a compression spring 559 (spring 559 is depicted in FIG. 67(B)). In operation, sleeve 554 is affixed to distal end 534 of filament 530, piston 556 is received within sleeve 554. Next spring 559 is inserted into cap 552, which in turn is attached to sleeve 554. Reduced diameter portion 556*a* of piston 556 is urged through bore 554*a* of sleeve 554. Portion 556*a* of piston 556 mates with notches 526, 528 in needle 520. The operation of suturing head 500 through a complete cycle will now be described.

Figure 66:
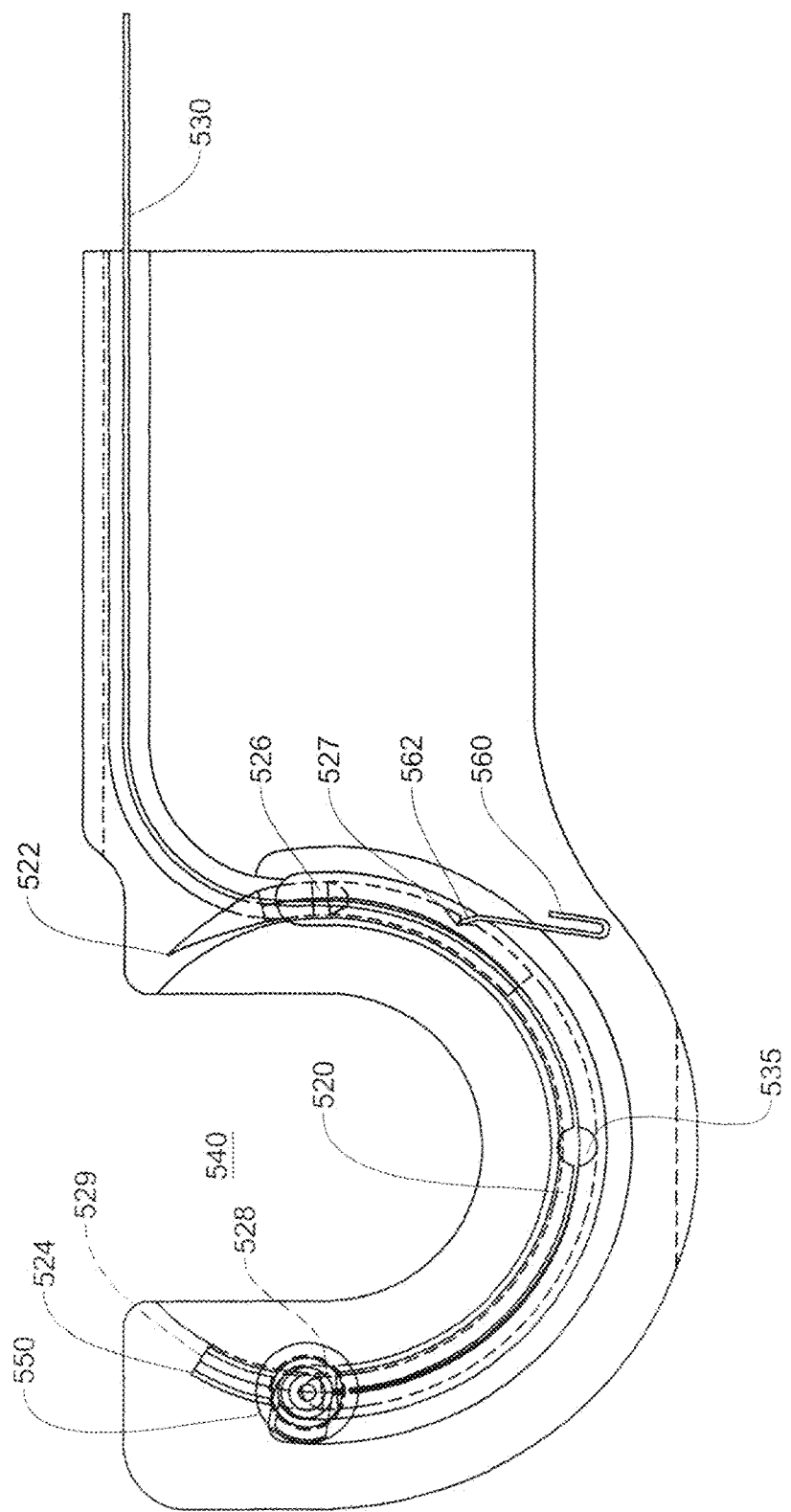

As depicted in FIG. 66, needle 520 having a first pointed end 522 and a second end 524 is in the home position prior to a rotation cycle, and engagement mechanism 550 is engaged with notch 528 in needle 520. As depicted, needle includes a hollow 529 in second end 524 of needle 520 for receiving a suture (not shown). Filament 530 further includes an enlarged portion 535 for riding against needle track 506 to reduce friction and ease operation of the suturing head. As further depicted, tip 562 of pawl 560 is biased to engage with antirotate notch 527 formed into the outer circumferential surface of needle 527.

Figure 67A:
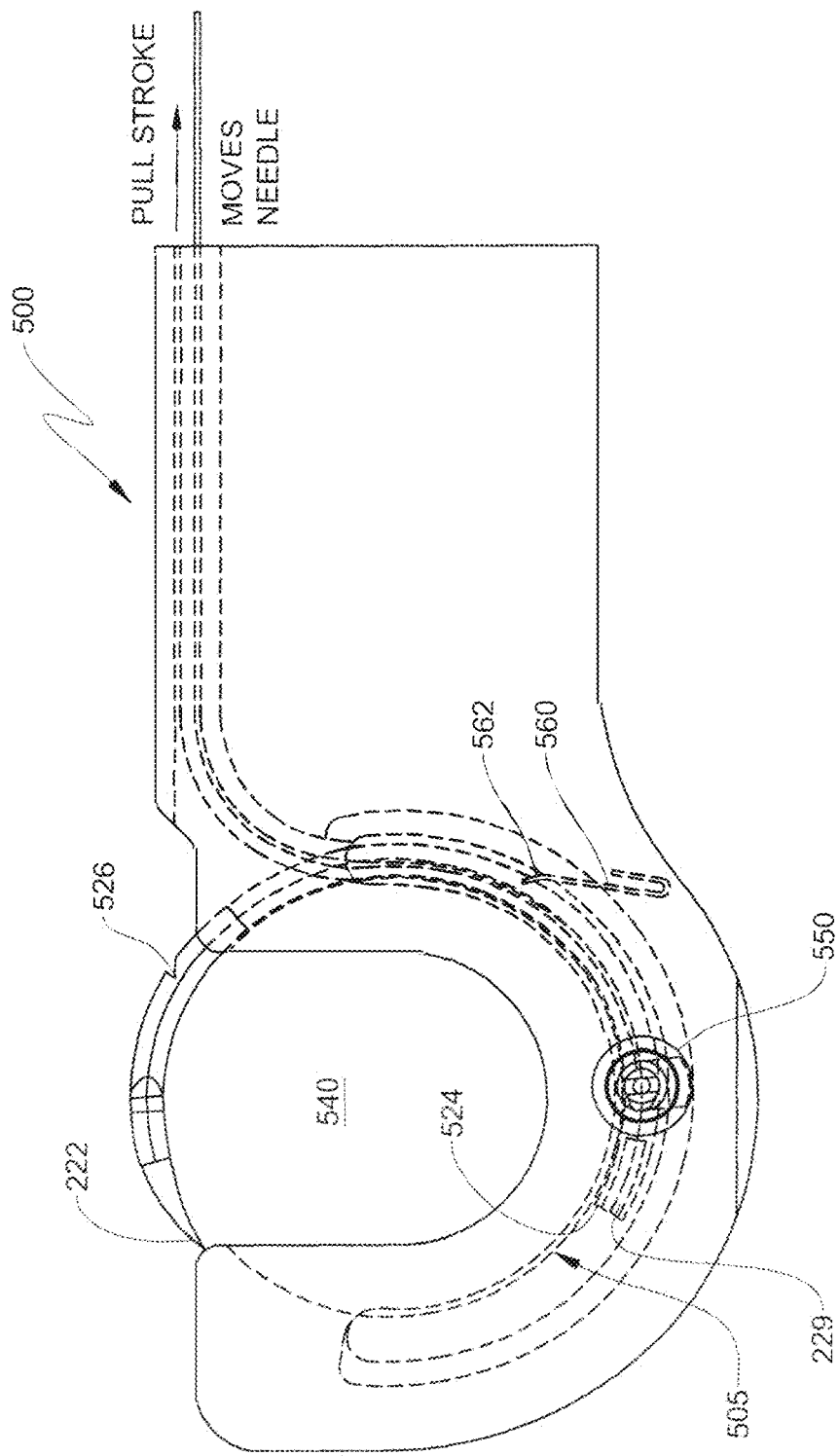
Figure 68:
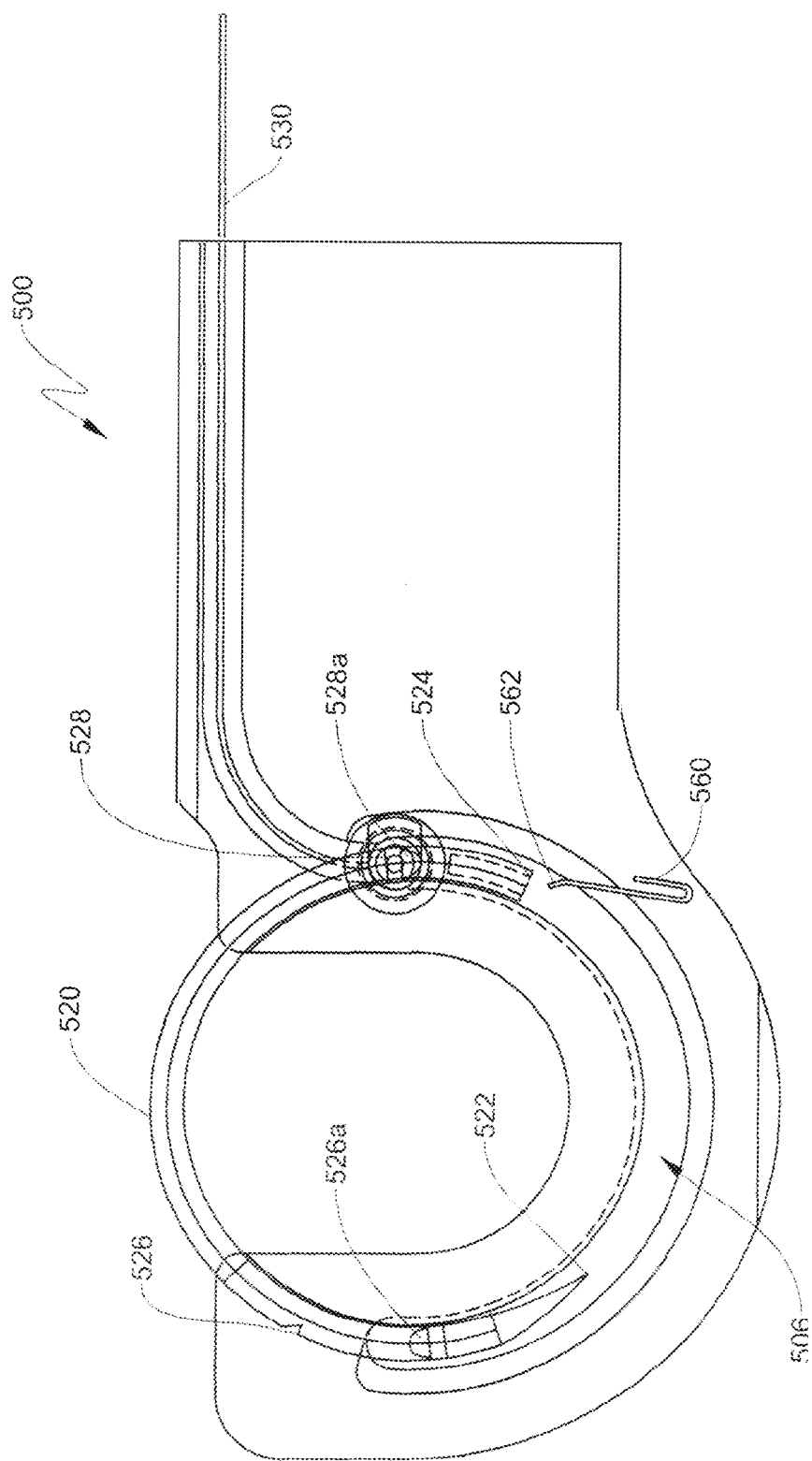
Figure 69:
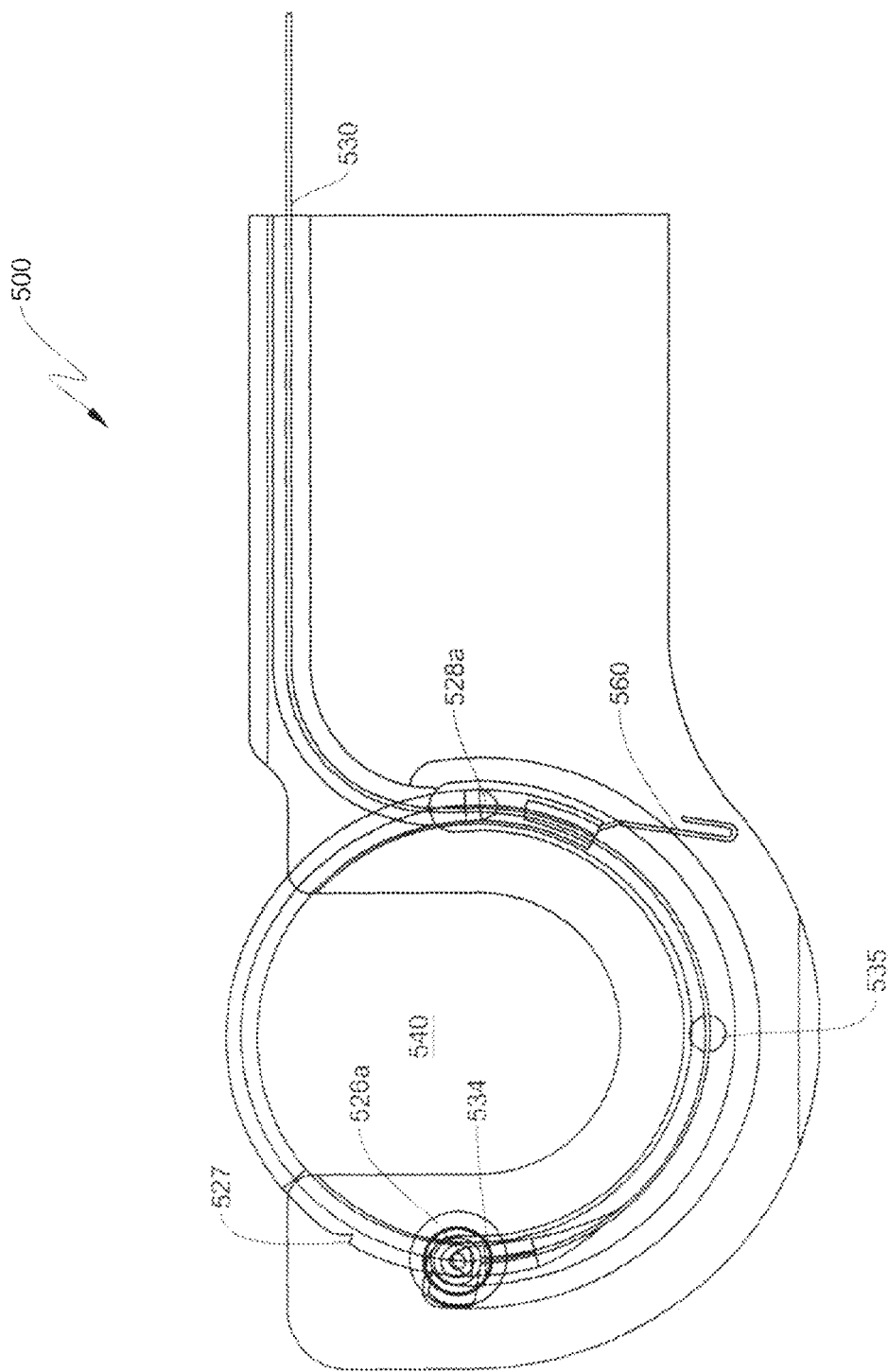

As depicted in FIG. 67(A), filament 530 is pulled proximally through the suturing instrument, causing engagement mechanism 550 to urge against notch 528 in needle, resulting in needle 520 being drawn through track 506, across gap 540, and back into track 506. Tip 562 of pawl 560 slides out of antirotate notch 527 of needle 520 and drags along the needle 520 as needle 520 moves through needle track 506. As can be seen in side cross-sectional view FIG. 67(B), end 556*a* of piston 556 is urged against notch 528 of needle 520 by spring 559. FIG. 68 depicts needle 520 after having been moved through a 180 degree rotation. As can be seen in FIG. 68, second end 524 of needle has moved past tip 562 of pawl 560, and tip 562 of pawl snaps into the needle track 506 to prevent the needle 520 from reversing direction. At this point, filament 530 is once again advanced distally, causing tip 556*a* of piston 556 to urge against the distal inclined surface 528*a* of notch 528. Inclined surface 528*a* acts as a ramp to push piston 556 into chamber 558 against the force of spring 559 until surface 556*a* rides up out of notch 528, and over the outer surface of needle 520 through track 505 until it passes over needle 520 and pops back out. As engagement mechanism 550 continues to be guided by arcuate notch 505, it encounters first end 522 of needle 520. The pointed end 522 of needle 520 once again acts as a ramp, compressing spring 559 as surface 556*a* rides up and over the needle 520 until surface 556*a* reaches notch 526. Upon reaching the notch 526, the piston snaps down into the notch. At this position, engagement mechanism is as depicted in FIG. 69.

Figure 70A:
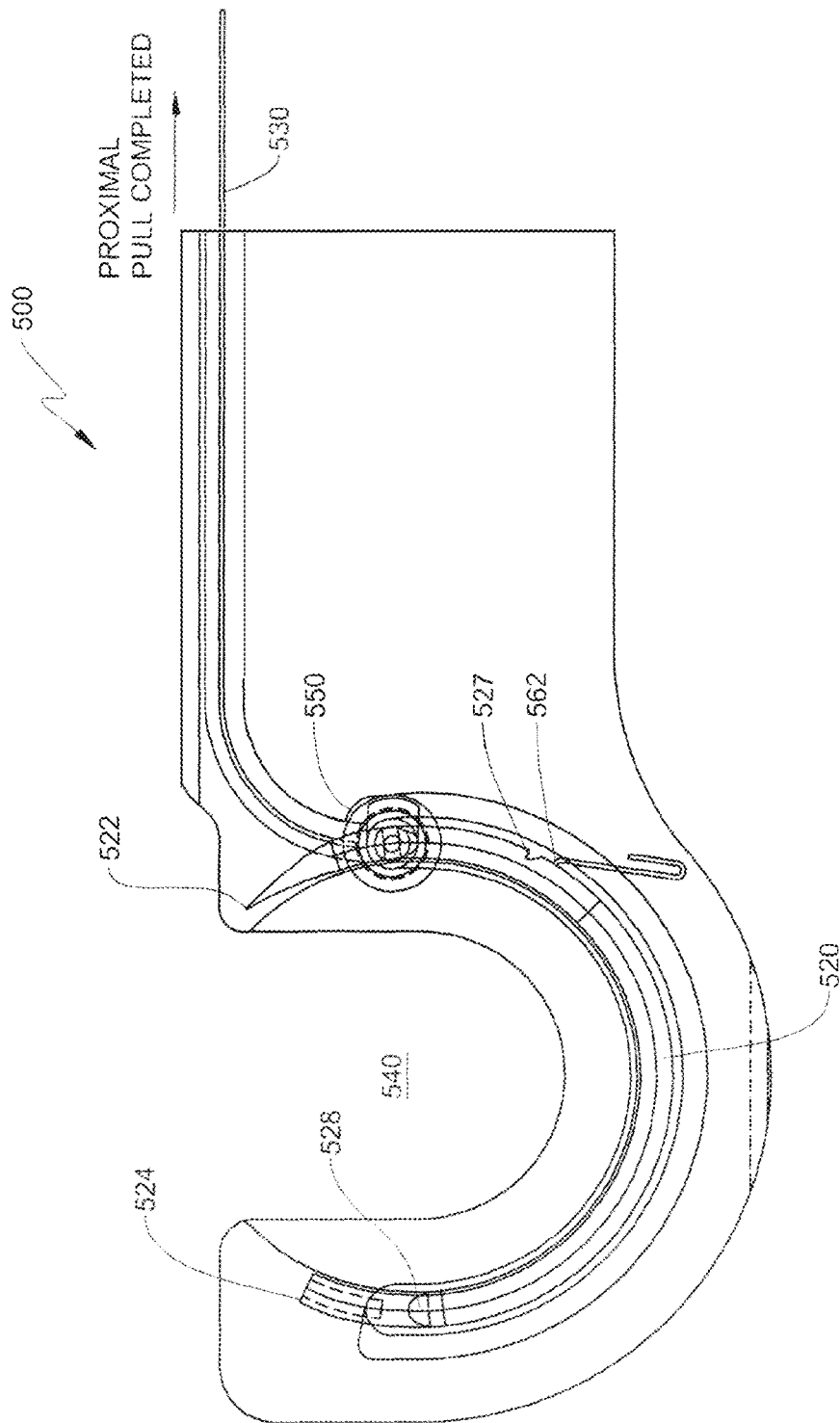
Figure 71A:
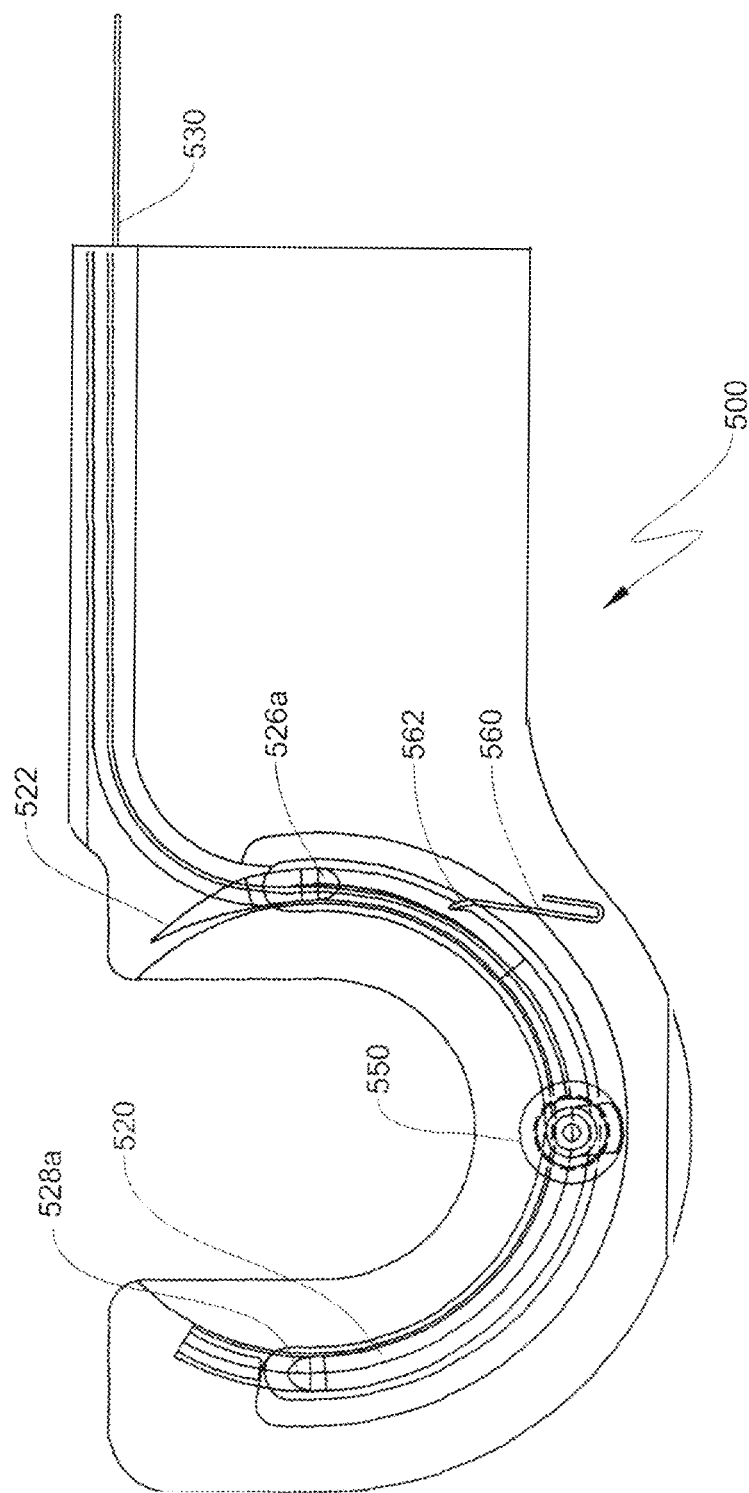
Figure 71B:
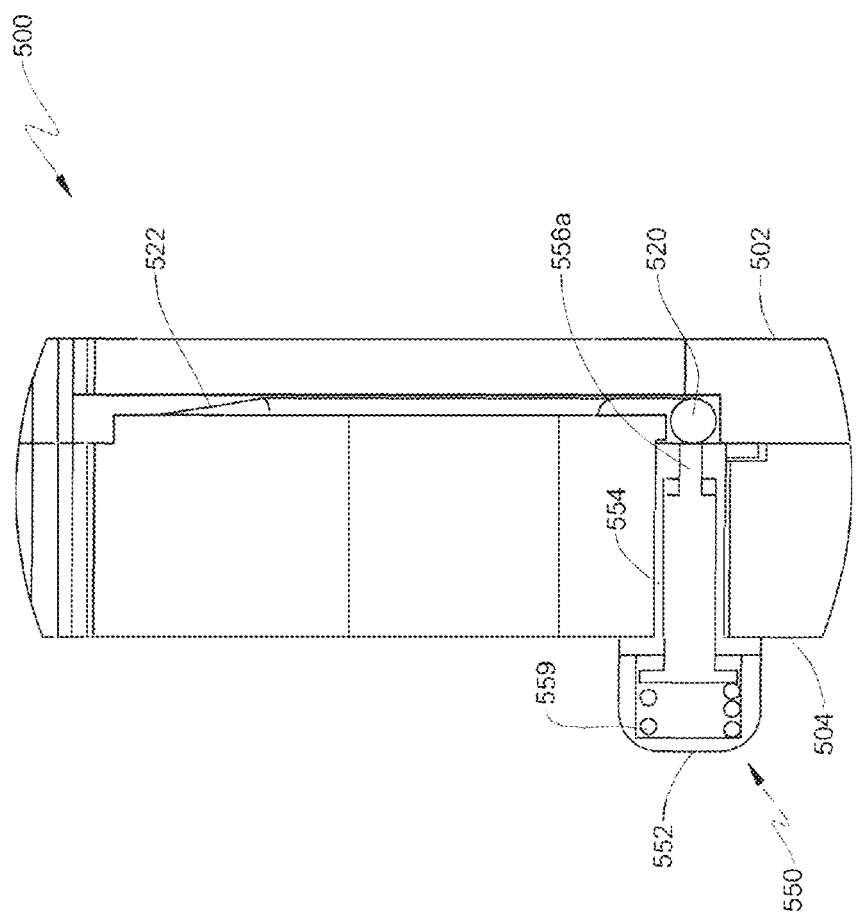

Next, filament 530 is once again pulled proximally through device causing the needle 520 to move through another 180 degree rotation, returning the needle 520 to the home position as depicted in FIGS. 70(A)-70(B). While antirotate notch 527 can move past tip 562 of pawl 560, when filament 530 is moved distally once again to pick up the needle at notch 528, needle 520 will move backward slightly until notch 527 engages with pawl tip 562. At that point, surface 556*a* of engagement mechanism 550 rides up inclined surface 526*a* and travels over the outer lateral surface of the needle 520 until the piston snaps into notch 528, preparing the suturing head 500 for another cycle as depicted in FIGS. 71(A)-71(B).

Suturing head 520 can be constructed using any desired techniques and any desired materials as described herein, for example, with reference to suturing head 356. Preferably, suturing head 500 is made from a polymeric material to permit manufacture of a low-cost, disposable device. Suturing head 500 can be mounted on a flexible shaft as depicted in FIG. 39(B).

In accordance with still further aspects of the invention, for purposes of further illustration and not limitation, FIGS. 72-85 depict further variations of the device generally depicted at FIGS. 1-38.

Figure 72:
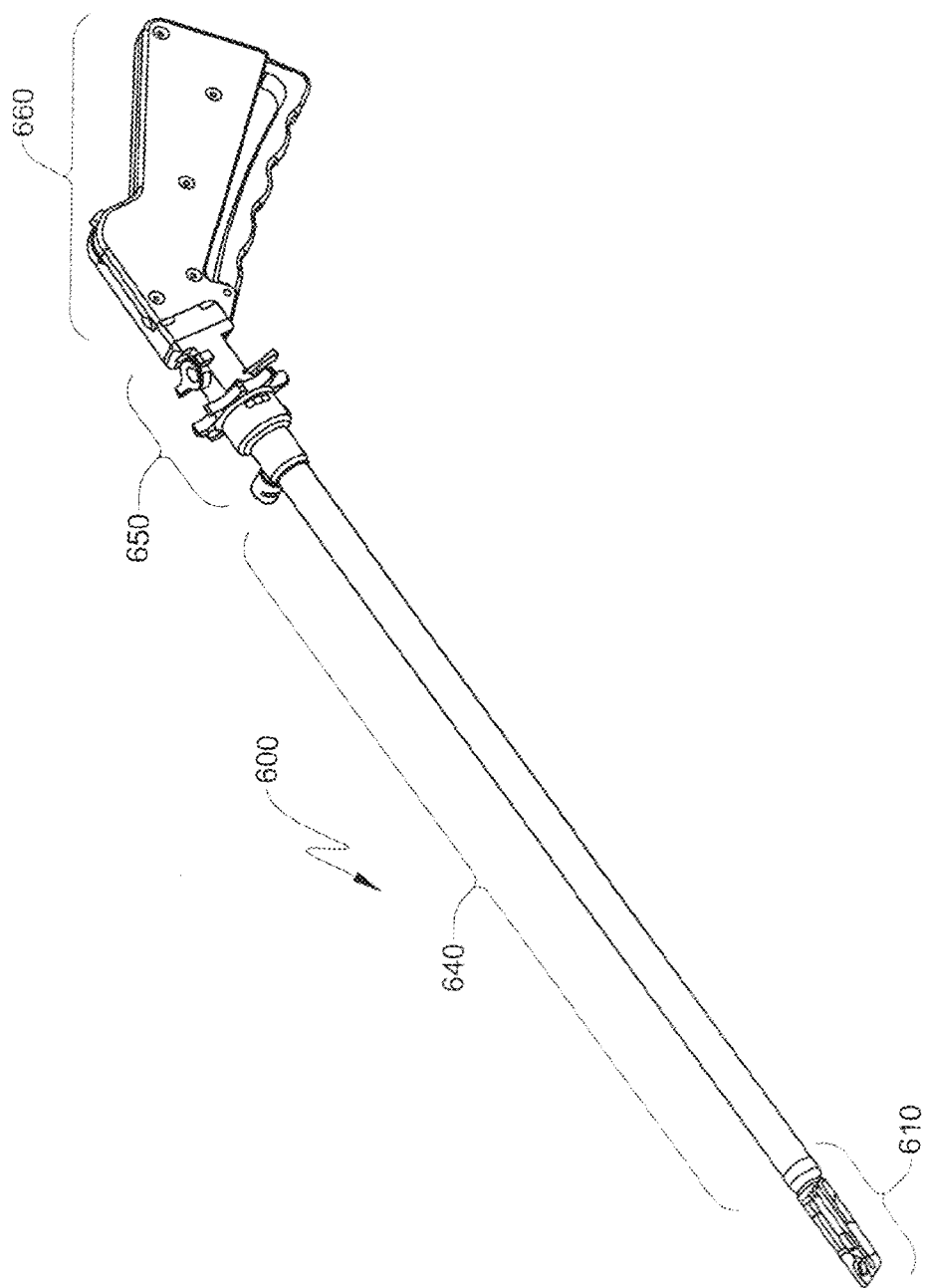
FIGS. 72-85 describe still a further embodiment of a device made in accordance with the invention.

As depicted in FIG. 72, device 600 is provided with a handle 660 that has been found to be particularly user-friendly and comfortable. Device 600 also includes a suturing head 610, an elongate tubular body 640, and a roticulation region 650.

Figure 73:
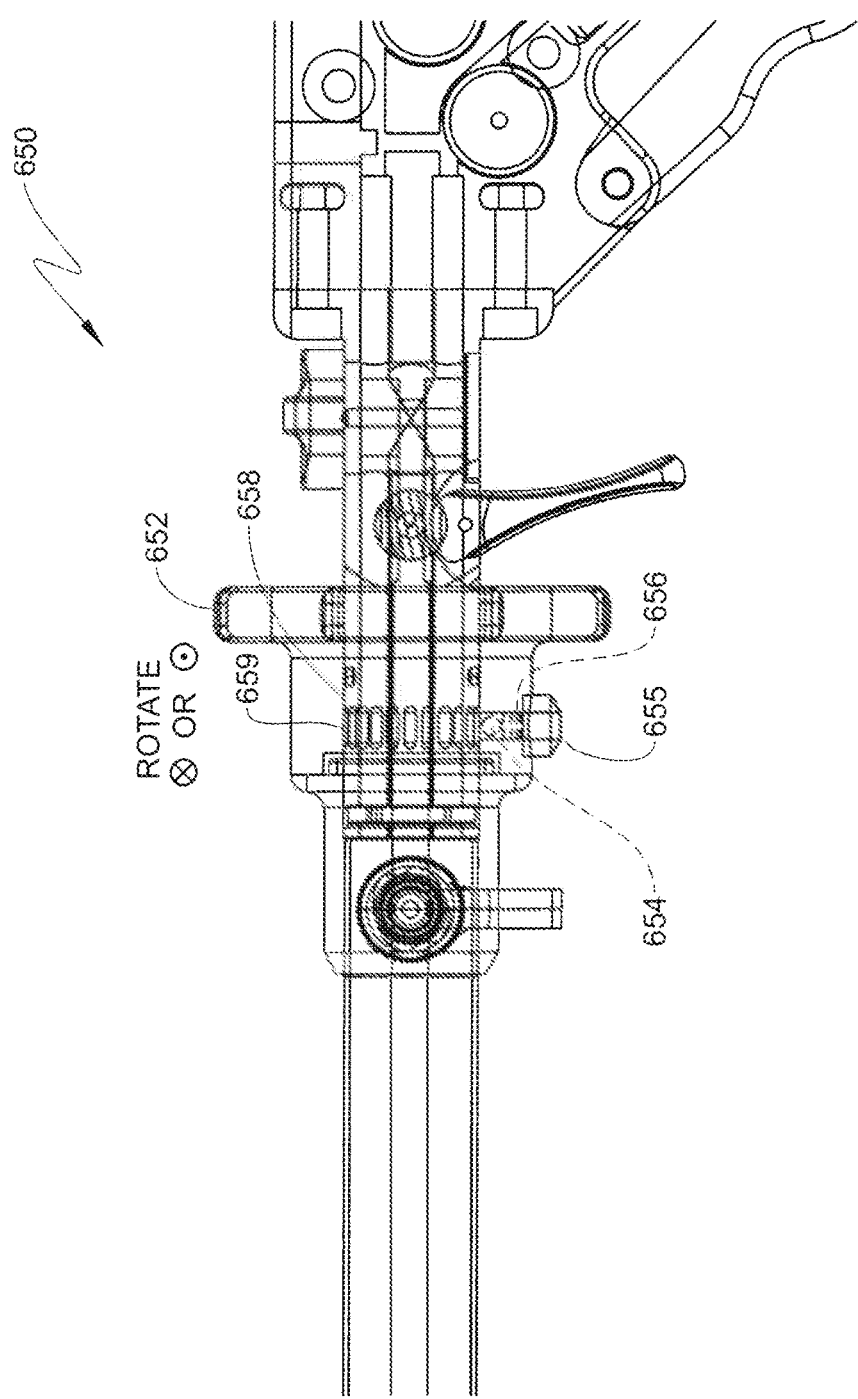

The roticulation region 650 is illustrated in FIG. 73. Roticulation section includes a hub 652 that is attached to tubular body 640. Hub 652 is rotatably mounted on a cylindrical bearing surface 658, having a plurality of elongate detents 659 surrounding the bearing surface 658. A detent ball 654 is contained within a detent housing 655, wherein a spring 656 urges detent ball 656 into a detent 659, preventing the hub from rotating freely, but also permitting hub to be rotated ("roticulated") about the axis of device 600, thereby permitting roticulation of the suturing head 610.

Figure 74:
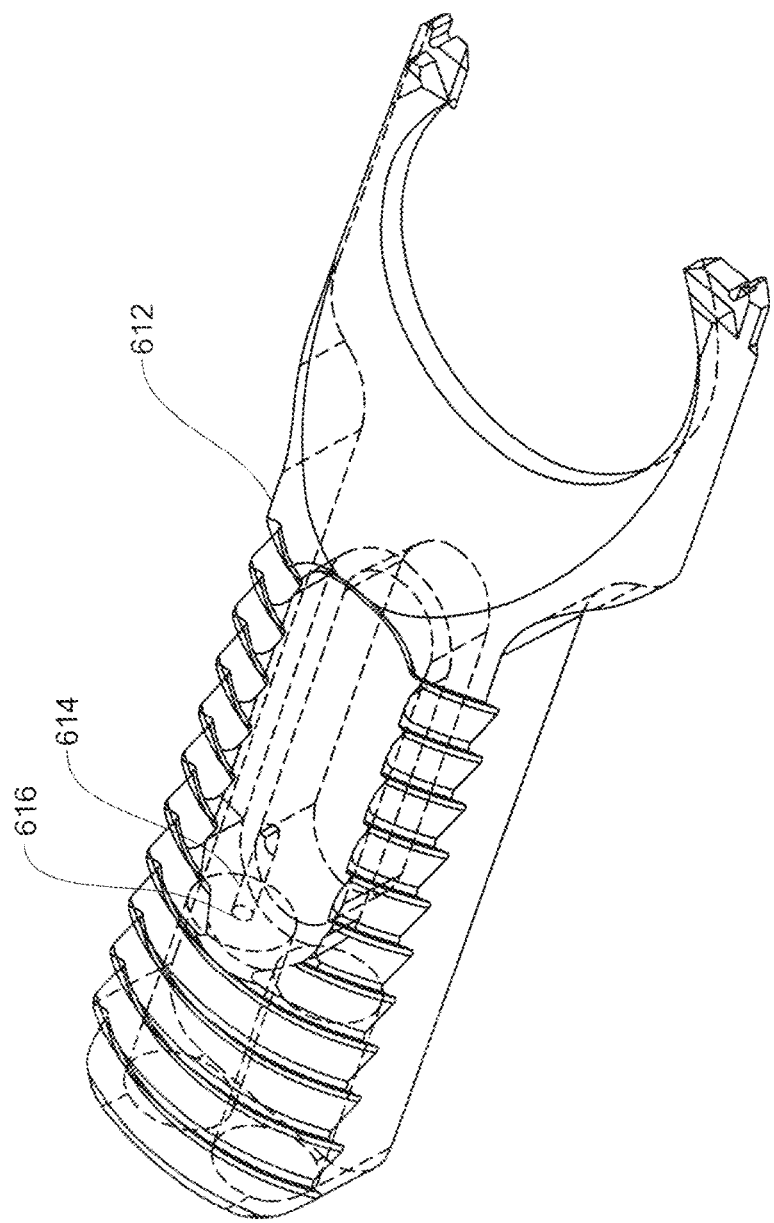
Figure 75:
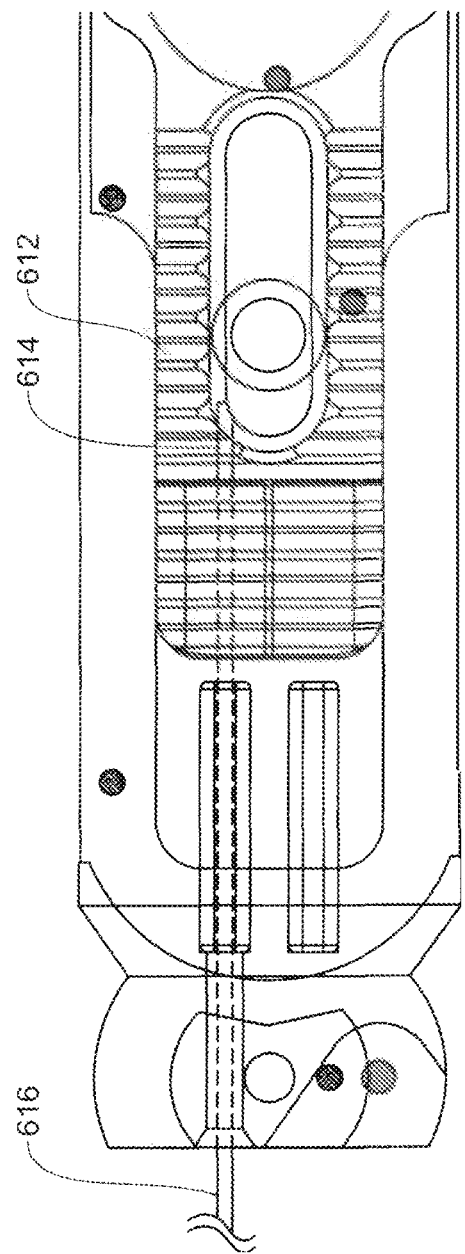
Figure 76:
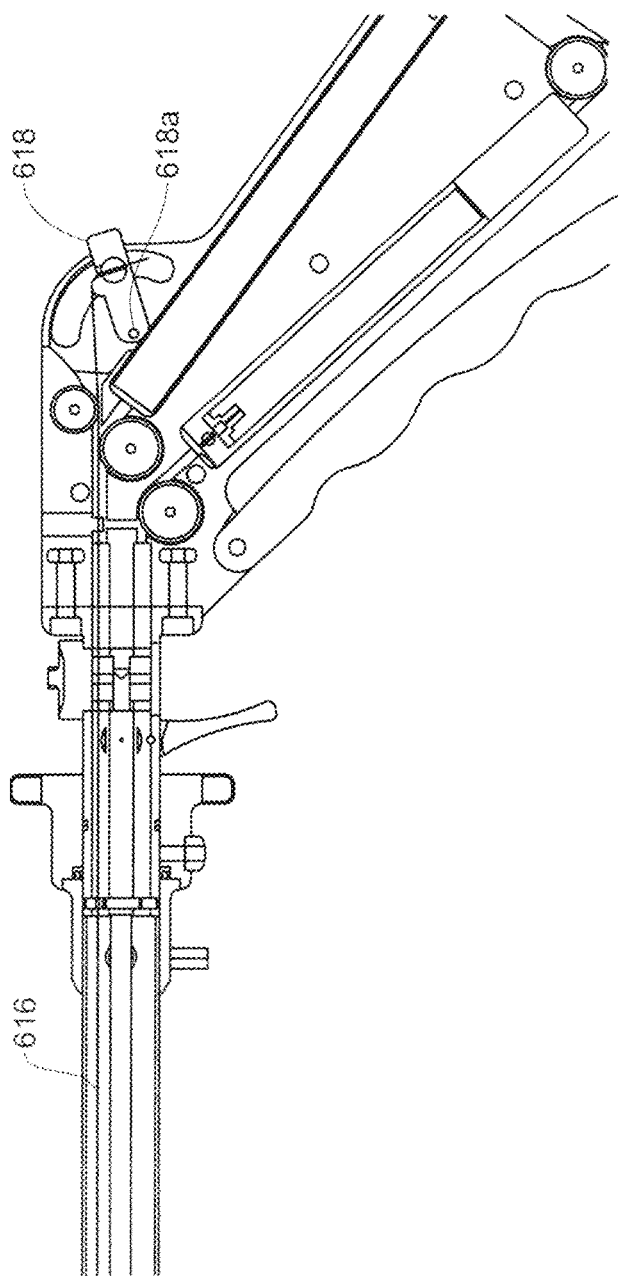
Figure 77:
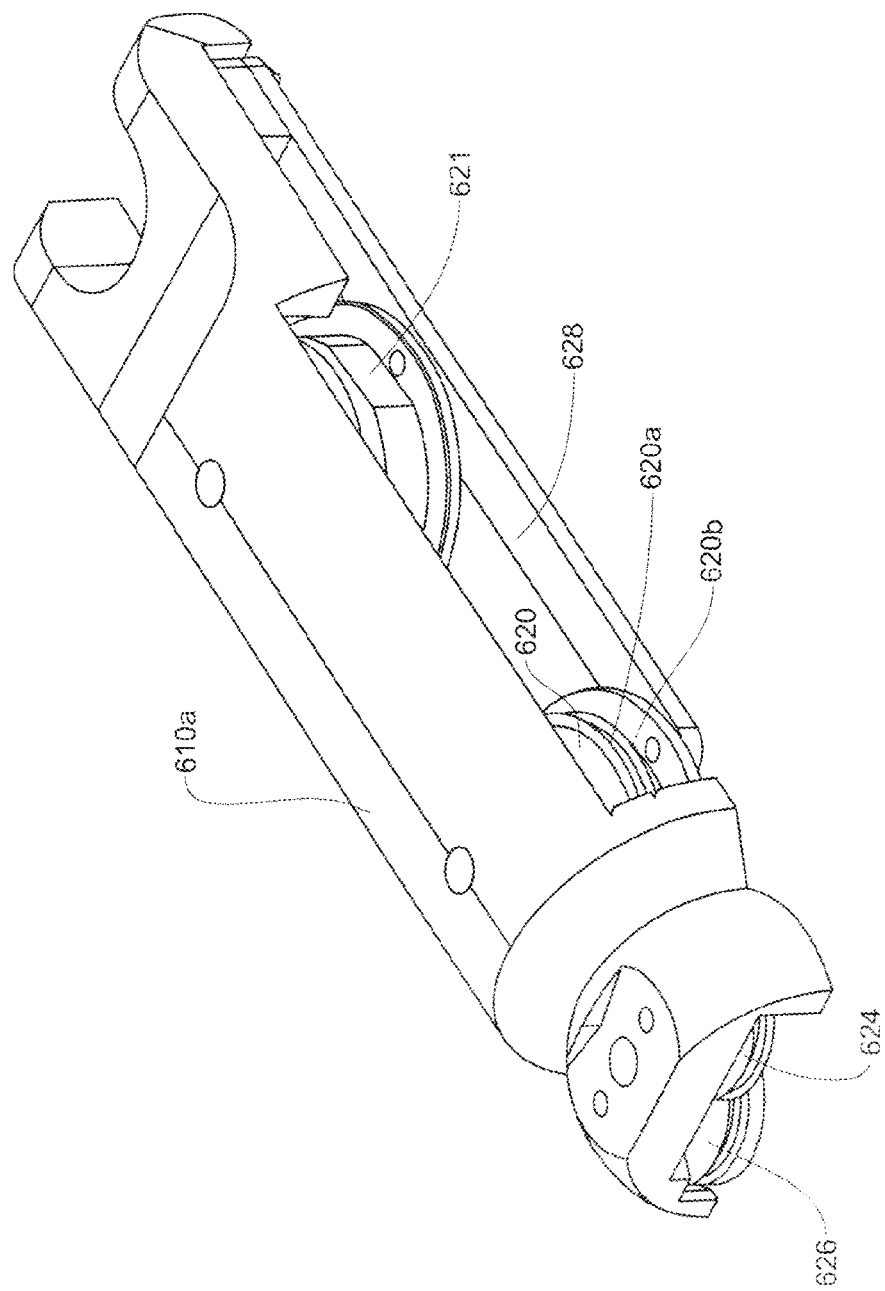
Figure 78:
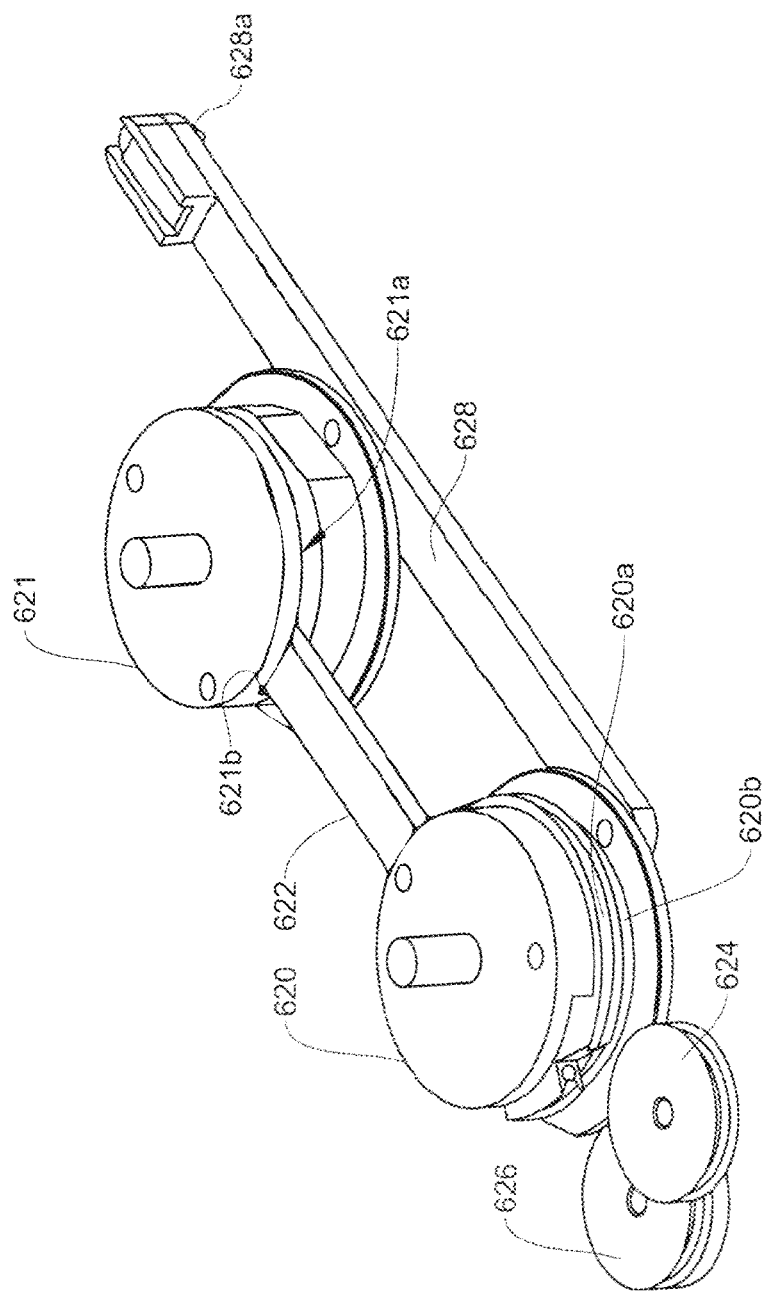
Figure 79:
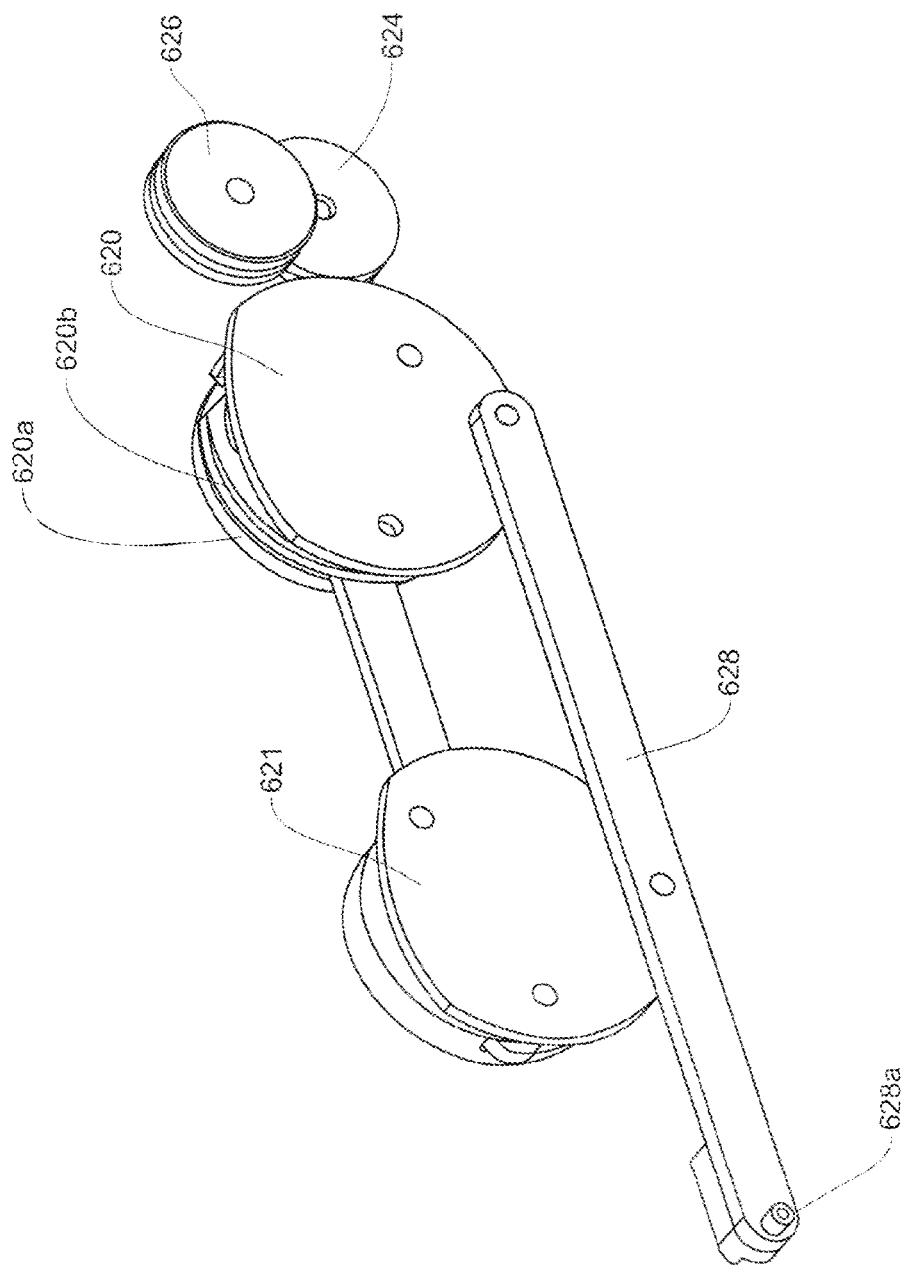
Figure 80:
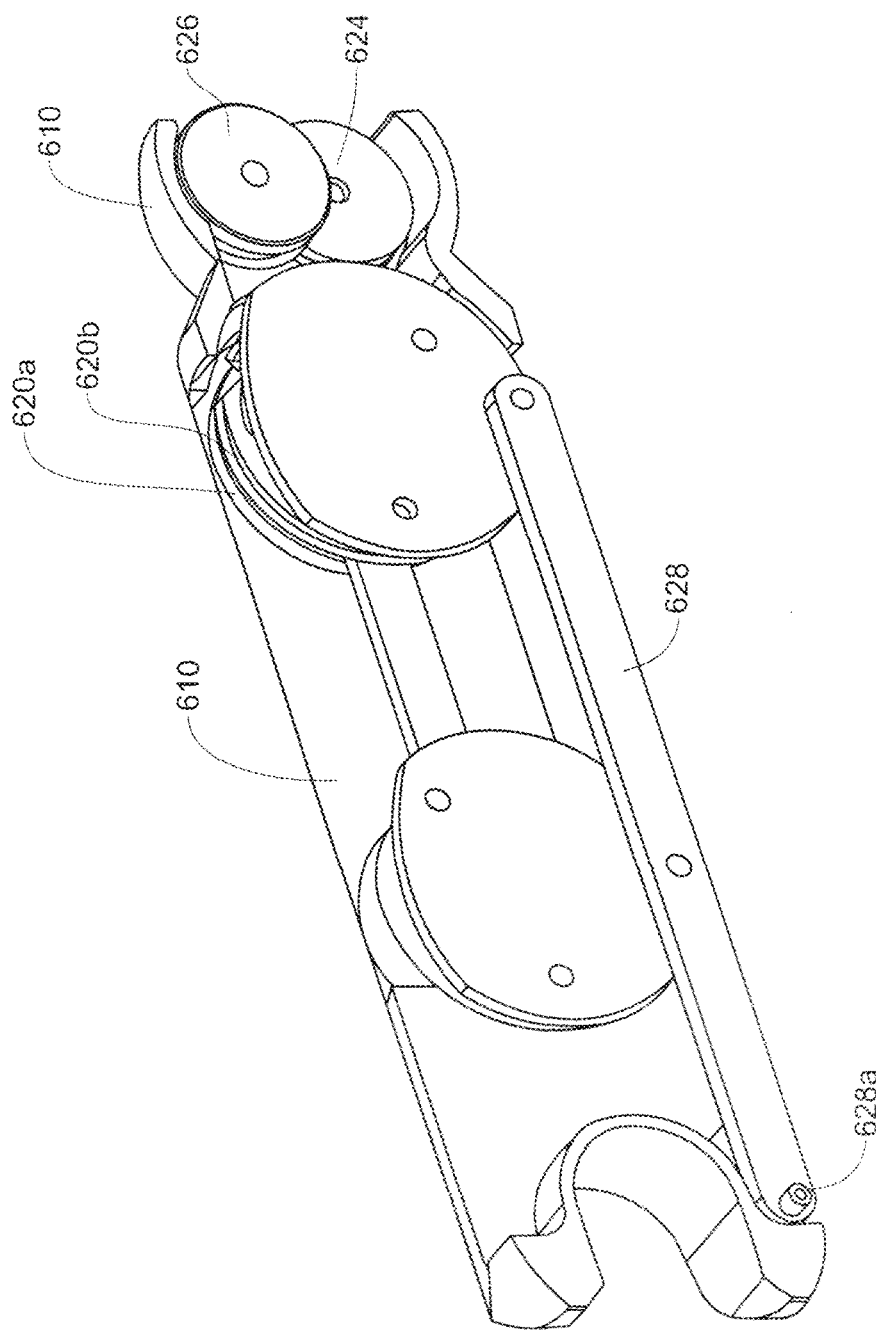
Figure 81:
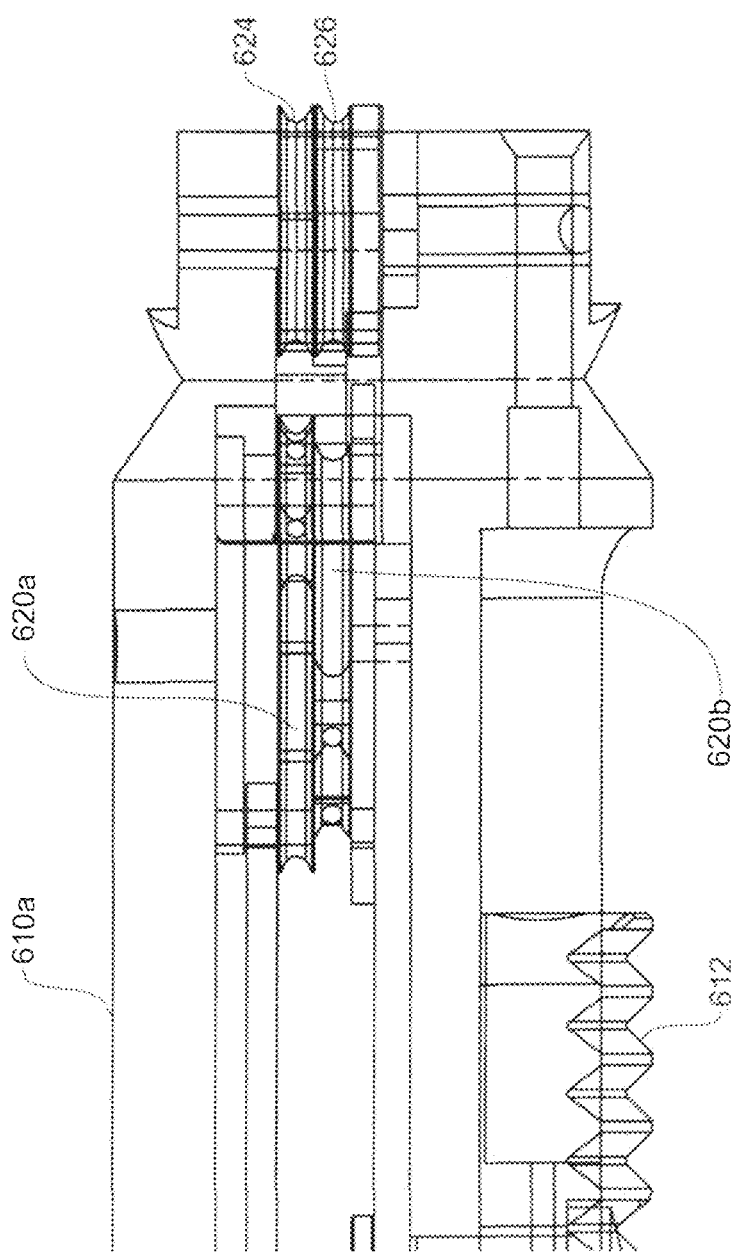
Figure 82:
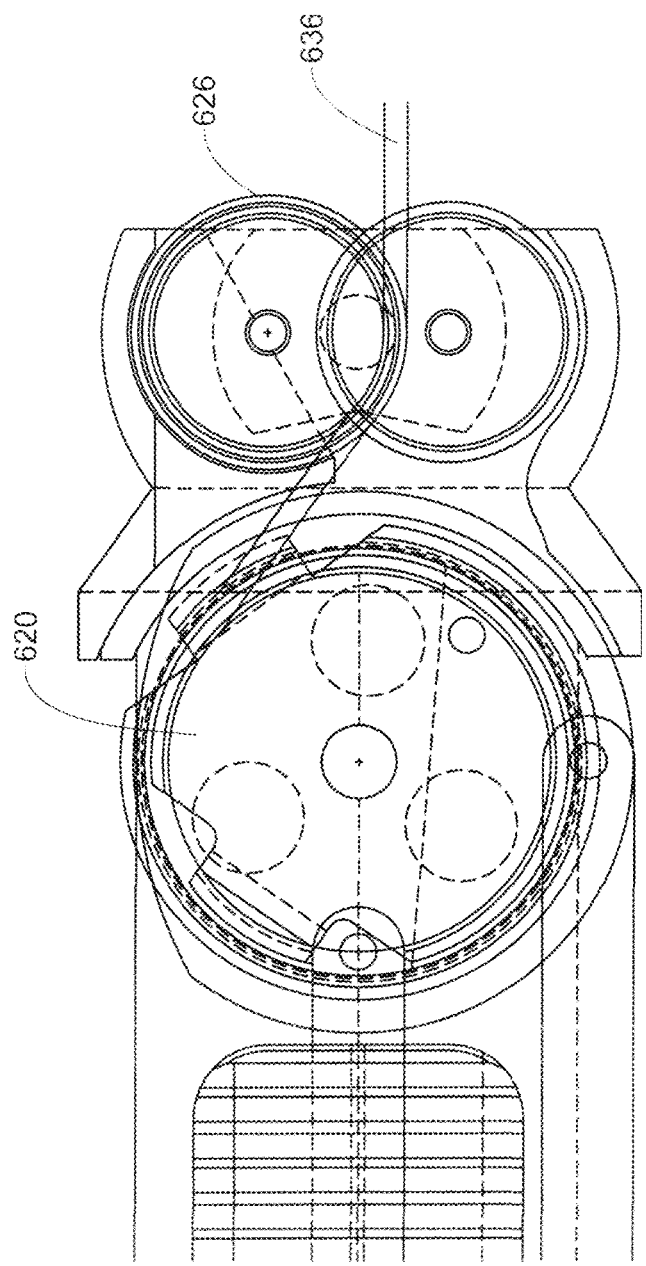
Figure 83:
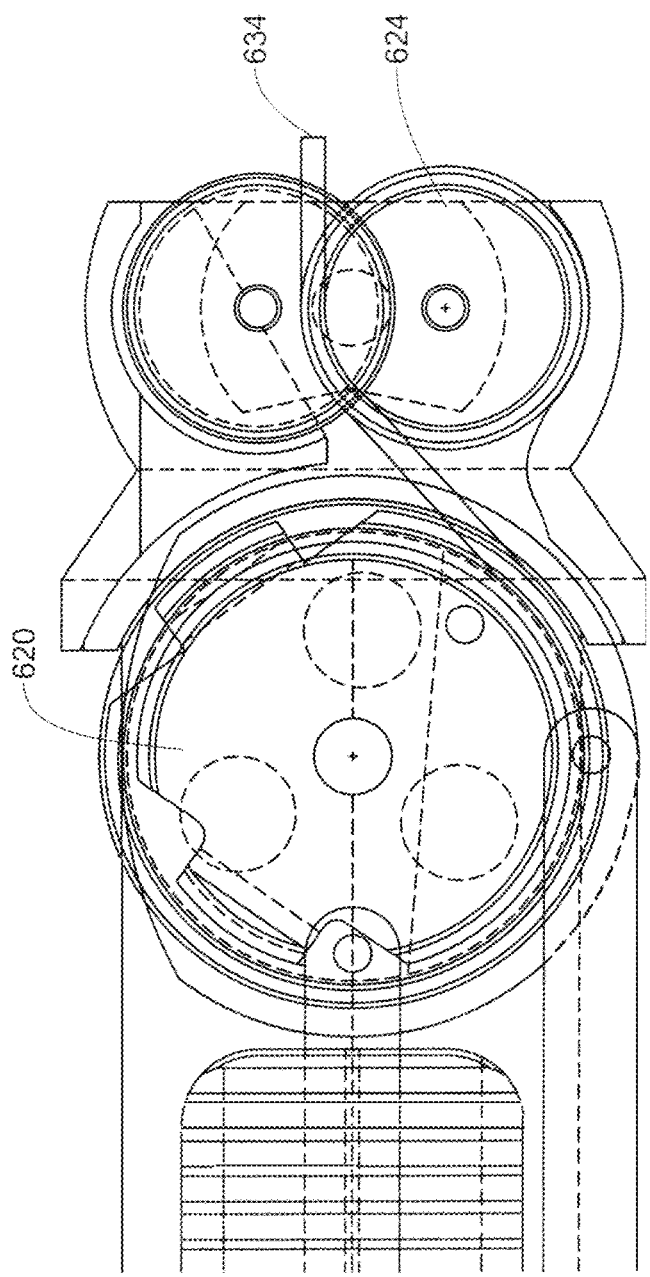

As with the suturing head depicted, for example, in FIGS. 30-31, a latch 612 is also provided in the embodiment of FIG. 72 to cover the suturing needle. Specifically, as depicted in FIGS. 74-76, latch 612 is provided, and is preferably biased (e.g., by a spring) to the closed position. While latch 612 can be retracted proximally by pushing on the latch 612 itself, during a procedure latch 612 may not be easily accessible. Thus, if the device 600 should jam, to avoid the difficulty in moving the latch backward to permit the needle to fall out of device, a pull wire 616 is provided that is attached at its distal end to the latch 612 (inside of a bore 614), and at its proximal end to a release trigger 618 that pivots about a point 618*a*. Thus, if it is desired to retract the latch 612 to permit the needle to fall out in the event of a jam, it can be released, the device 600 can be withdrawn, and the needle can be removed with forceps. The device 600 can then be reused with a new needle.

Figure 84:
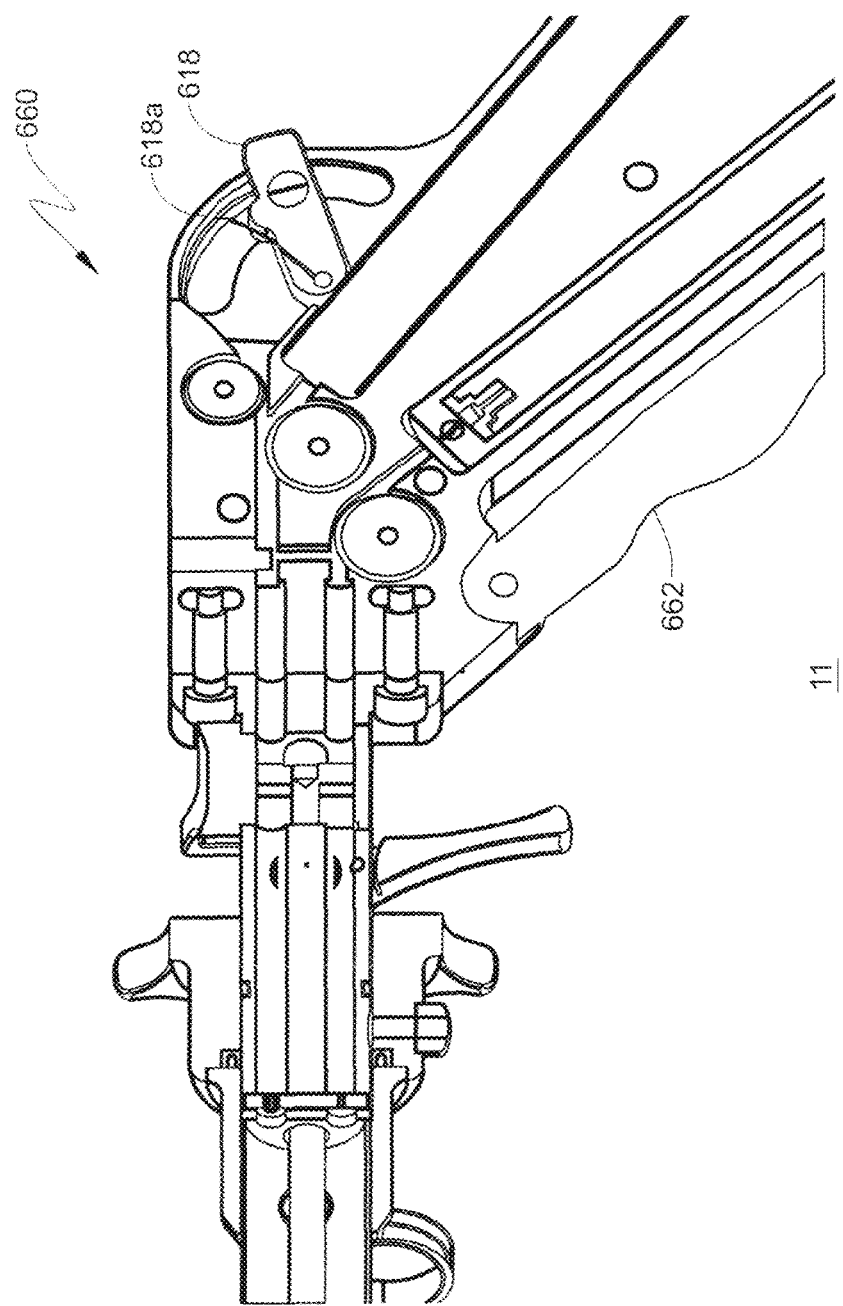
Figure 85:
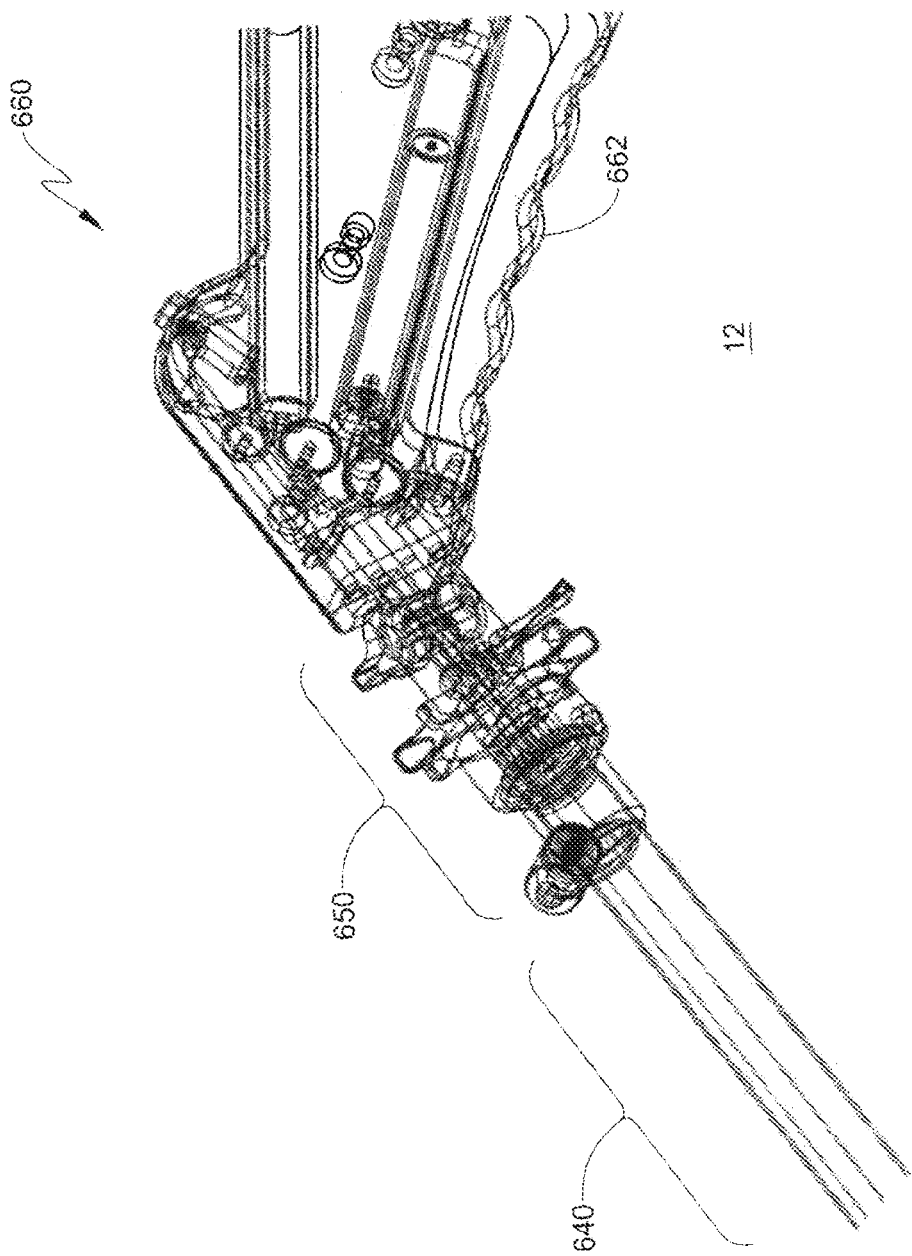

FIGS. 77-83 depict an alternative drive mechanism for the suturing head 610. Specifically, all components of the drive mechanism are fitted to one side of the suturing head 610a, rather than being anchored to both sides of the suturing head 610. This is very advantageous in assembly. Specifically, all drive components (pulleys and the like) are attached to side 610a of the suturing head. This prevents any inconvenience in needing to align the pulleys and other drive components with two opposing housing sections, and facilitates assembly generally as this design permits the drive components to be stacked and attached to a single member. As will be noted, the drive components bear some similarity to those depicted in FIGS. 34-35. A drive cable 634 is routed around a drive idler 624, and into the drive pulley 620a. Drive pulley 620a, in turn, drives an idler pulley 621 by way of an actuator arm 628 when advancing the suturing needle. A link or strut 622 is provided that acts as a stop for rotation of pulley 621 by engaging a bearing surface 621b in groove 621a. A needle engagement mechanism/needle assembly extension 628a is provided for driving the suturing needle (not depicted). In addition, a return cable 636 is routed around a return idler 626, and into the return pulley 620b, which is concentric with the drive pulley 620a. Return pulley 620b, in turn, drives idler pulley 621 by way of actuator arm 628 in a direction opposite from the drive pulley 620a, causing engagement mechanism 628a to return to the home position to repeat the half cycle. FIGS. 84-85 depict cross sectional and three dimensional wireframe views of the handle portion 660 of device 600, respectively, depicting, for example, actuator handle 662 as well as the arrangement of interior passages through which drive and return cables are routed. The return cable 636 is preferably spring-loaded so as to cause the needle engagement mechanism 628a to return to its home position.

The suturing devices of the presently disclosed embodiments can be used for laparoscopic procedures, including but not limited to laparoscopic colostomy, colectomy, adrenalectomy, splenectomy, repair of paraesophageal hernia, inguinal hernia repair, ventral hernia repair, Nissen fundoplication, liver lobectomy, gastrectomy, small bowel resection, treatment of small bowel obstruction, distal pancreatectomy, nephrectomy and gastric bypass. Those skilled in the art will recognize that the presently disclosed embodiments can be used in other laparoscopic procedures.

In using the device 150 of the presently disclosed embodiments, the abdomen is insufflated with gas to create a working space for the user. Any gas known to those skilled in the art including, but not limited to, nitrogen or carbon dioxide, can be used. Access portals are established using trocars in locations to suit the particular surgical procedure. A variety of surgical instruments may then be inserted into the body through these access ports/cannulas. The user then introduces the distal end portion of suturing device 150 into a cannula, and then laterally articulates the suture head assembly 156 using the articulation lever 166 located just distal to the top of the handle 160. The suture head assembly 156 is then positioned relative to the tissue/vessel to be sutured together, and the user locks the suture head assembly 156 in place using the locking lever 164. The user then, through manipulation of the suturing device 150, positions a plurality of separated tissue segments into the opening defined at the distal end portion of the suture head assembly 156 and within the aperture 218 of the needle holder assembly 188. The user, using only one hand, may manipulate the device 150 while actuating the handle 160 to close an incision with a continuous suture whose stitches may be individually tensioned precisely and uniformly along the length of the suture similar to suturing done by hand in the conventional way. The user may employ a single suture which would extend the entire length of the incision or multiple sutures. Thus, by placement of the device 150 with the needle holder assembly aperture 218 spanning the incised tissue segments and actuating the handle 160, the suturing device 150 enables the user to lay down a running stitch or interrupted stitch to close the tissue incision in a time efficient manner. Those skilled in the art will recognize that any conventional procedure for conducting laparoscopic surgery can be used with the device 150.

The minimalized structural design of the suture head assembly 156 enables the user to have a clear, unobstructed view of the suturing needle 220 during advancement through the tissue segments during the course of a suturing operation, thereby enabling precise placement of the suturing device 150 to provide uniform sutures and precluding the risk of tearing tissue by placement too close to the edge of the incision. The suturing device 150 is then advanced a short distance along the incision and the aforementioned operation is repeated to produce another stitch comprising the suturing material or thread 246.

The user may continue to manipulate the suturing device 150, alternately advancing and actuating rotation of the needle 220 about an axis that is generally parallel to the direction of advancement to create a continuous suture which may extend through the entire length of the incision or a series of interrupted stitches. After each individual stitch is laid down, the stitch is tightened by exerting a pull on the suturing material or thread 246 so that the resultant suture is tensioned uniformly along the length of the incised tissue segments. Therefore, a tight closure of the segments is accomplished and bleeding and tearing of tissue are minimized. Once the appropriate amount of suture material or thread 246 has been placed, the user can use a needle grasper to tighten and knot the formed stitches.

The suturing device 150 may be configured in different ways with respect to length and angle of the suture head assembly 156. The size of the needle 220, the needle holder assembly 188, the needle holder aperture 218 and the aperture position may also be varied for use in open surgery to perform procedures such as closing of the fascia, skin closure, soft tissue attachment, anastomosis, fixation of mesh, grafts and other artificial materials. Moreover, devices made in accordance with the teachings herein can be used in combination with needle loader devices described, for example, in U.S. patent application Ser. No. 12/175,442, filed Jul. 17, 2008.

All patents, patent applications, and published references cited herein are hereby incorporated by reference in their entirety. It will be appreciated that one or more of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the present disclosure.

What is claimed is:

1. A suturing device having a proximal end and a distal end comprising:
   a) an arced suturing needle having a pointed leading end and a trailing end;
   b) a suturing head disposed proximate the distal end of the device, the suturing head being configured to support the arced suturing needle therein, the arced suturing needle having a curved body, the curved body covering an arc greater than about 180°, wherein the arced suturing needle is disposed in and adapted and configured to be advanced along an arcuate path about an axis of rotation substantially perpendicular to a longitudinal axis defined by the suturing device;

c) a reciprocating needle drive configured to advance the needle along a first direction led by the leading end of the needle, wherein reciprocating components of the reciprocating needle drive that are disposed within the suturing head are mounted to the same housing section to facilitate assembly of the suturing head, wherein the reciprocating components of the reciprocating needle drive include at least once reciprocating idler wheel rotatably coupled to the housing section and at least one drive bar pivotally coupled to the reciprocating idler wheel at an outer periphery of the reciprocating idler wheel.

2. The suturing device of claim 1, wherein the side of the housing section on which the reciprocating components of the reciprocating needle drive are disposed is located on an interior portion of the suturing head.

3. The suturing device of claim 1, wherein the reciprocating components of the reciprocating needle drive that are disposed within the suturing head are mounted to one face of said housing section.

4. The suturing device of claim 3, wherein the reciprocating components of the reciprocating needle drive that are mounted to said one face of said housing section are covered by a second housing section to protect said reciprocating components.

5. The suturing device of claim 1, wherein said reciprocating components of the reciprocating needle drive that are mounted to said one face of said housing section further include at least one needle driver pivotally connected to said drive bar.

6. The suturing device of claim 5, wherein said needle driver includes a drive pawl for releasably engaging a drive notch formed into an engagement surface of the arced suturing needle that faces inwardly toward the axis of rotation of the arced suturing needle.

7. The suturing device of claim 6, wherein said drive pawl is urged into contact with said arced suturing needle under spring force.

8. The suturing device of claim 6, wherein said drive pawl rides in a carrier track defined at least in part by a C-brace disposed radially inwardly with respect to the arced suturing needle.

9. The suturing device of claim 8, wherein the needle is advanced along a needle track that is disposed radially outwardly with respect to the C-brace.

10. The suturing device of claim 9, wherein the drive pawl is the only portion of the reciprocating drive in the suturing head that extends into the needle track.

11. The suturing device of claim 5, wherein said needle driver includes a spring.

12. The suturing device of claim 11, further comprising a removable cartridge disposed in the suturing head, the removable cartridge including a cartridge housing, wherein a needle track is formed into the removable cartridge.

13. The suturing device of claim 12, wherein the suturing head includes a coupling for releasably holding the removable cartridge.

14. The suturing device of claim 12, wherein the removable cartridge is disposed at a distal end of the suturing head.

15. The suturing device of claim 1, wherein the reciprocating needle drive advances the needle through a 360° rotation about the axis of rotation in two 180° drive strokes.

16. The suturing device of claim 1, wherein the suturing head is configured to be introduced through a cannula.

17. The suturing device of claim 1, wherein the reciprocating needle advancement drive is motorized.

18. The suturing device of claim 1, wherein at least a portion of the suturing head is modular and replaceable.

* * * * *